(12) United States Patent
Sang et al.

(10) Patent No.: US 7,585,955 B2
(45) Date of Patent: *Sep. 8, 2009

(54) PROTEIN SEPARATION FROM A PROTEIN MIXTURE

(75) Inventors: Qing-Xiang (Amy) Sang, Tallahassee, FL (US); Ziad Joseph Sahab, Tallahassee, FL (US)

(73) Assignee: Florida State University Research Foundation, Inc, Tallahassee, FL (US)

( * ) Notice: Subject to any disclaimer, the term of this patent is extended or adjusted under 35 U.S.C. 154(b) by 146 days.

This patent is subject to a terminal disclaimer.

(21) Appl. No.: 11/366,124

(22) Filed: Mar. 2, 2006

(65) Prior Publication Data

US 2007/0055055 A1    Mar. 8, 2007

Related U.S. Application Data

(60) Provisional application No. 60/658,104, filed on Mar. 3, 2005.

(51) Int. Cl.
  *A23J 1/00*    (2006.01)
(52) U.S. Cl. .................. 530/412; 530/416; 530/418
(58) Field of Classification Search ............. 530/412, 530/416, 418
  See application file for complete search history.

(56) References Cited

U.S. PATENT DOCUMENTS

| | | | | |
|---|---|---|---|---|
| 4,145,406 | A | * | 3/1979 | Schick et al. ............ 436/541 |
| 4,228,154 | A | | 10/1980 | Fisher et al. |
| 5,250,662 | A | | 10/1993 | Chang |
| 5,626,764 | A | * | 5/1997 | Burns et al. ............ 210/661 |
| 5,888,966 | A | | 3/1999 | Larsen et al. |
| 6,489,447 | B1 | | 12/2002 | Basey et al. |

OTHER PUBLICATIONS

Ziad J Sahab and Qing-Xiang A Sang, Albumin elimination from human plasma, Abstract, Division of Analytical Chemistry, Aug. 28-Sep. 1, 2005, ANYL 150, Washington, DC.
Ben Herbert, Pier Giorgio Righetti, A Turning point in proteome analysis: Sample prefractionation via multicompartment electrolyzers with isoelectric membranes, Electrophoresis, 3639-3648, 21, Wiley-VCH Veriag GmbH, 69451 Weinheim, 2000.
Radhakrishna S. Tirumalai, King C. Chan, Darue A. Prieto, Haleem J. Issaq, Thomas P. Conrads, and Timothy D. Veenstrat, Characterization of the Low Molecular Weight Human Serum Proteome, pp. 1096-1103, Molecular & Cellular Proteomics 2.10, Aug. 13, 2003.
Stanford Moore and William H. Stein, Chromatography of Amino Acids on Sulfonated Polystyrene Resins, Journal of Biological Chemistry, Oct. 1951;192(2) pp. 663-681.
2-D Electrophoresis for Proteomics, A Methods and Product Manual, Bio-Rad Laboratories, Inc., Bulletin 2651 US/EG Rev C.
Ziad J Sahab, Yewseok Suh, and Qing-Xiang A Sang, Pre-fractionation of proteins from crude biological samples prior to 2-D gel electrophoresis, Abstract, Division of Analytical Chemistry, Aug. 28-Sep. 1, 2005, ANYL 151, Washington, DC.
Lian Shan and David J. Anderson, Gradient Chromatofocusing. Versatile pH Gradient Separation of Proteins in Ion-Exchange HPLC: Characterization Studies, Analytical Chemistry, American Chemical Society, vol. 74, No. 21, Nov. 1, 2002, pp. 5641-5649.
Ziad J. Sahab, Yewseok Suh, and Qing-Xiang Amy Sang, Isoelectric Point-Based Prefractionation of Proteins from Crude Biological Samples Prior to Two-Dimensional Gel Electrophoresis, Journal of Proteome Research, American Chemical Society, 2005, 4, pp. 2266-2272.

* cited by examiner

*Primary Examiner*—Tekchand Saidha
(74) *Attorney, Agent, or Firm*—Bryan Cave LLP

(57) ABSTRACT

A process for separating a protein from a sample containing a mixture of proteins is disclosed. The process comprises forming an aqueous combination comprising the sample and an ion exchange material at a pH which is less than the pI of a first fraction of the proteins in the aqueous dispersion but greater than the pI of a second fraction of the proteins in the aqueous dispersion. The aqueous dispersion may then be intensely mixed, causing a fraction of the proteins in the combination to bind to the ion exchange material, and, optionally, centrifuged, causing the combination to stratify into a concentrated solids fraction and a supernatant, the supernatant containing the fraction of the proteins that did not bind to the ion exchange material. This process, including the steps of intense mixing and centrifugation, requires no expensive, specialized instrumentation, can be quickly performed, and is carried out in non-denaturing conditions, allowing for the separated proteins to be further studied.

5 Claims, 35 Drawing Sheets

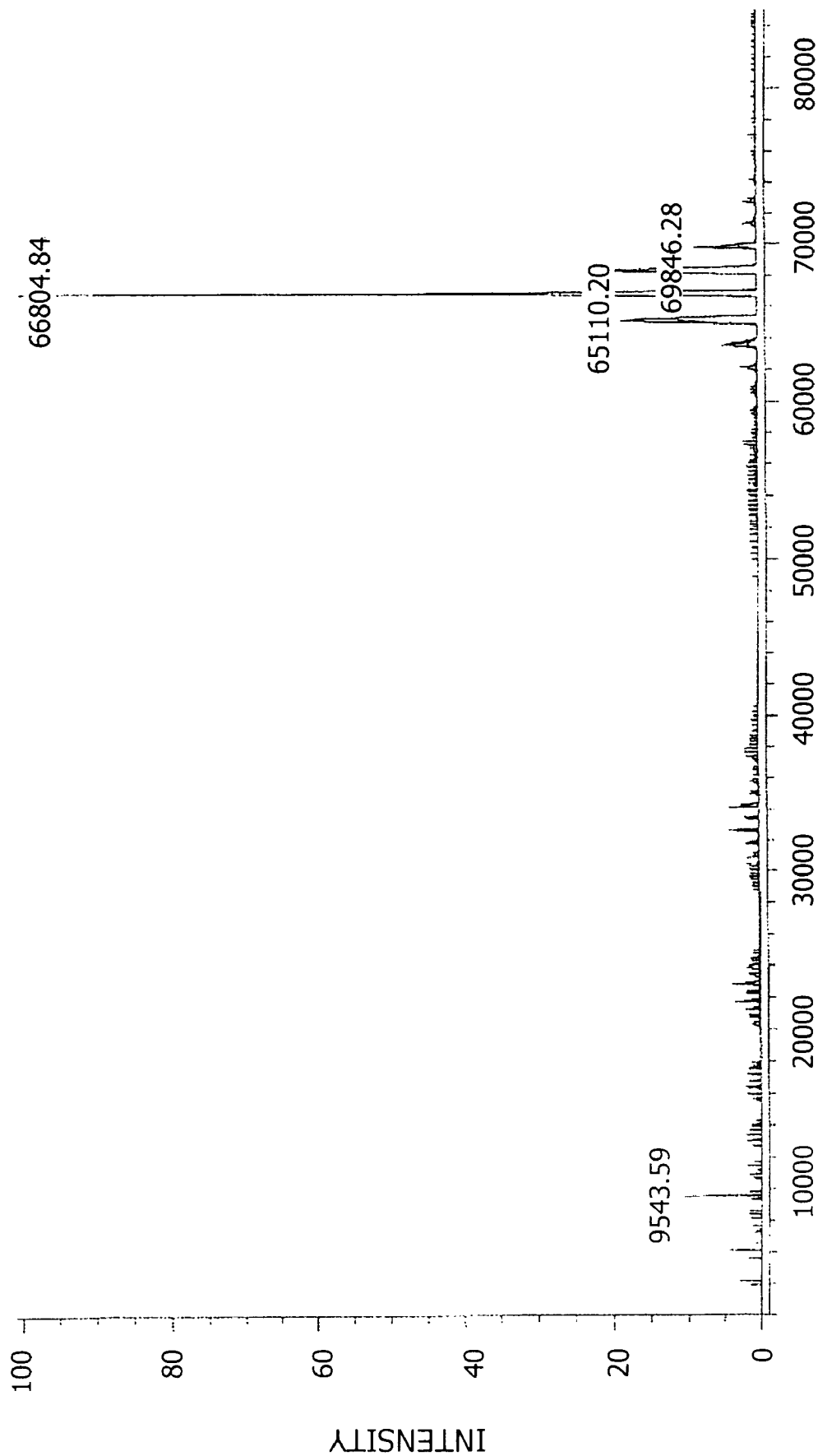

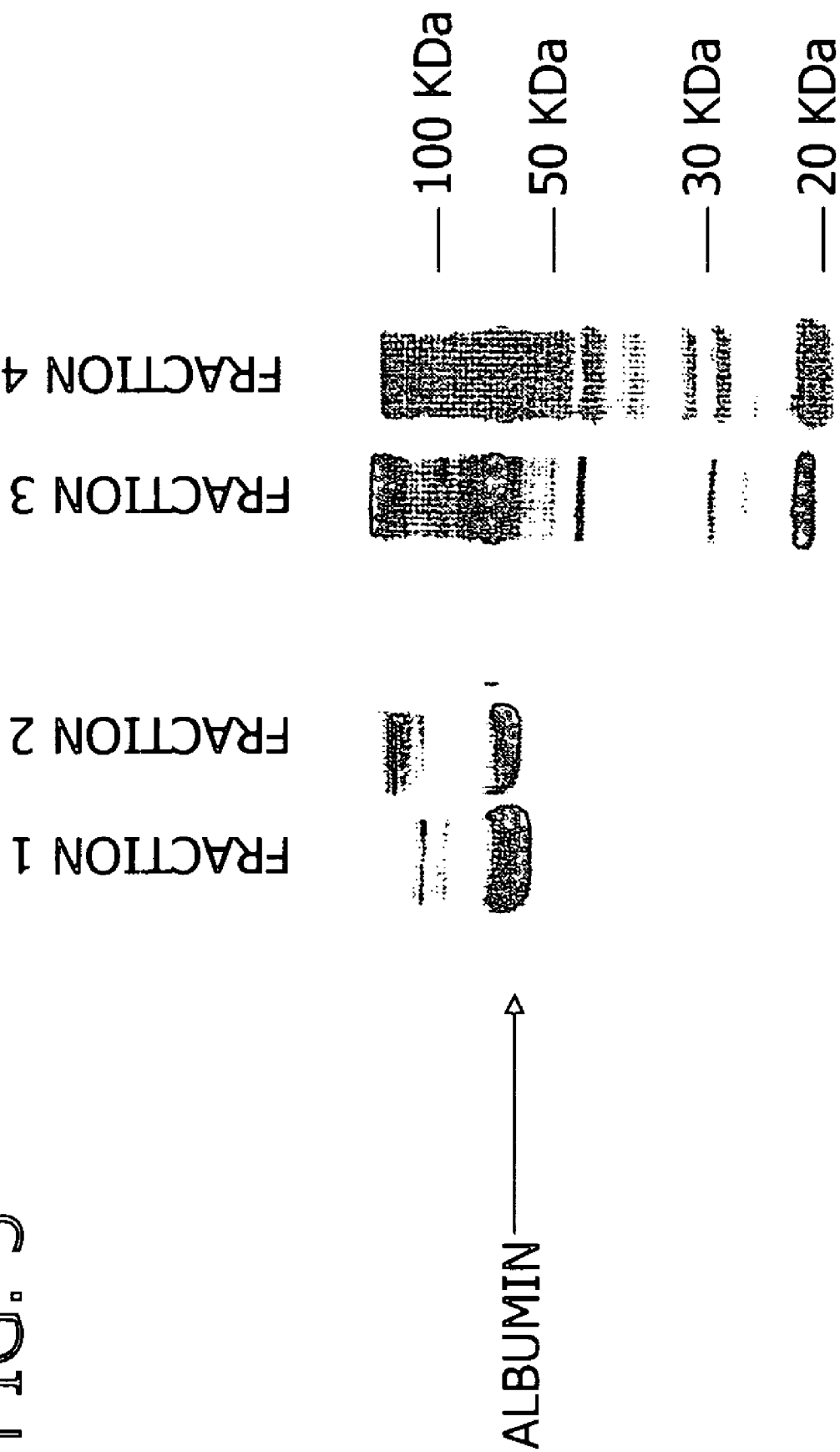

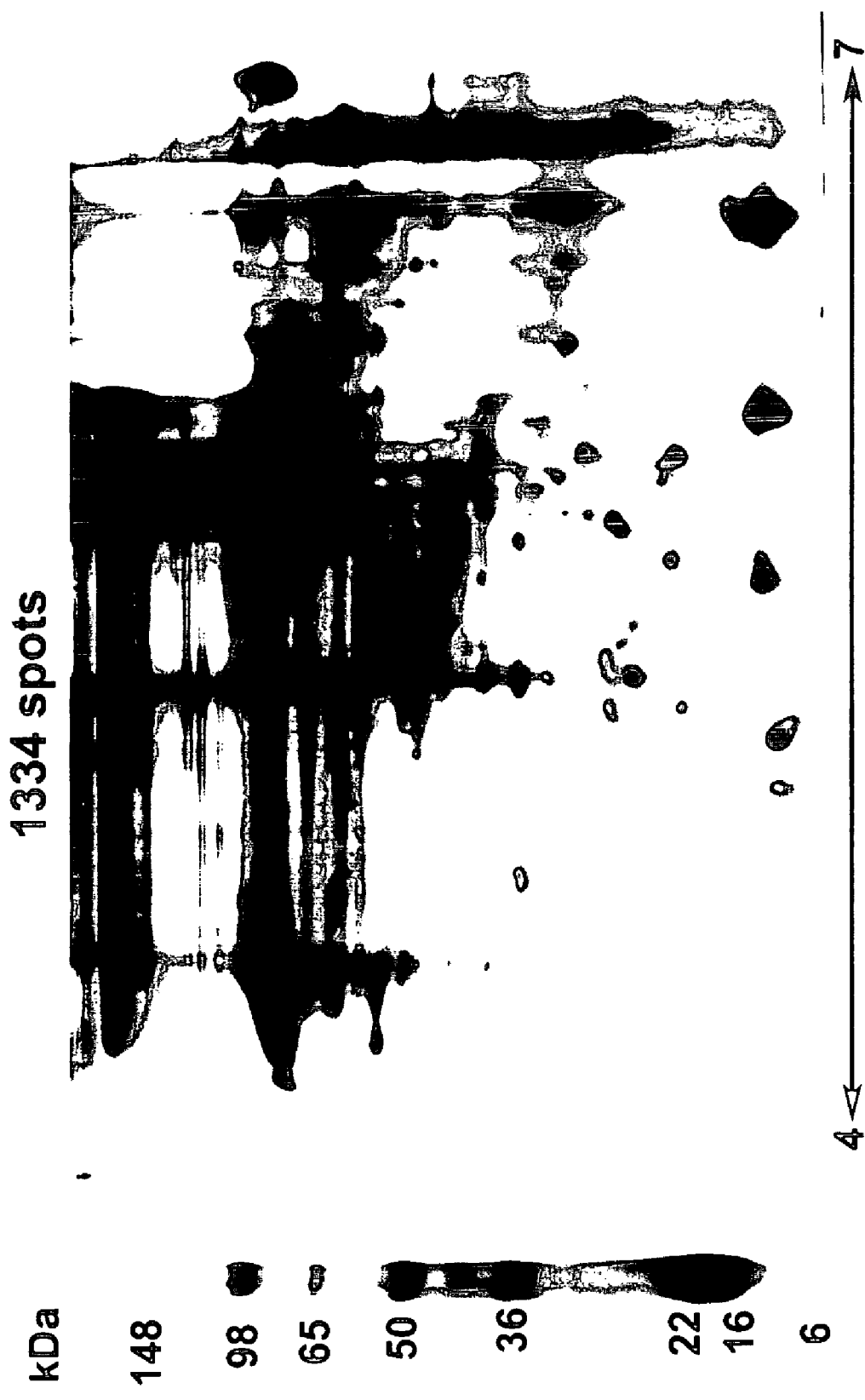

PROTEIN SEPARATION FROM A PROTEIN MIXTURE

REFERENCE TO RELATED APPLICATION

This is a non-provisional application claiming priority under 35 U.S.C. § 119 to provisional application No. 60/658,104, Filed Mar. 3, 2005, the entire disclosure of which is hereby incorporated by reference.

FIELD OF THE INVENTION

The present invention generally relates to the separation of a protein from a sample containing a mixture of proteins. More specifically, the present invention relates to the separation of one or more proteins from an aqueous sample containing a mixture of proteins in a process in which the aqueous sample is intensely mixed with an ion exchange material wherein the aqueous sample is at a pH which is greater than the pI of a first fraction of the proteins in the sample but less than the pI of a second fraction of the proteins in the sample, thereby inducing one of the fractions to bind to the ion exchange material.

BACKGROUND OF THE INVENTION

Diagnostic, research and therapeutic applications often require the purification or separation of one or more proteins from more complex mixtures, for example, mixtures derived from biological tissues, biological fluids, cell cultures and the like. Various techniques which typically exploit differences in physical properties as between proteins in the mixture, such as charge, hydrophobicity, size, shape, or affinity for a particular ligand have been proposed for protein separation.

Column chromatography is one method commonly used to separate protein mixtures. In this method, a sample containing a mixture of proteins is typically passed through a stationary bed of chromatographic resin; in general, proteins having relatively less affinity for the resin elute first, followed by proteins having relatively greater affinity for the resin. Examples include reversed-phase high-performance liquid chromatography and anion exchange column chromatography. For example, in ion exchange chromatography, positively charged proteins tend to be retained by a cation exchange column whereas proteins having a negative or neutral charge pass through the column, and negatively charged proteins tend to be retained by an anion exchange column whereas proteins having a positive or neutral charge pass through the column. Flow rates through ion exchange columns, however, tend to be relatively slow. One of the restrictions of separating proteins using anion exchange column chromatography is the inability of using high concentrations of urea in the extraction reagent or in the buffers. This high concentration of urea is required to solubilize the proteins that have a low aqueous solubility but when injected in a column chromatography will generate a high backpressure. This pre-fractionation is therefore limited to the soluble proteins.

An alternative to column chromatography is batch chromatography. In batch chromatography, a quantity of ion exchange resin is added directly to a sample to form a dispersion of the resin in the sample and the dispersion is then agitated or gently mixed. The protein-bound resin is removed from the remainder of the sample by centrifugation or filtration, leaving unbound protein in solution. See, for example, Chang, U.S. Pat. No. 5,250,662, and Larsen, et al., U.S. Pat. No. 5,888,966. Again, however, times required for the separation may be undesirably long.

Another common technique used for protein separation is electrophoresis. In electrophoresis, proteins migrate in an electric field at rates that depend on their net charge, size, and/or shape. There are several different techniques that fall under the heading of electrophoresis that are well known in the art, including gel electrophoresis (PAGE) and SDS-electrophoresis (SDS-PAGE). One such technique uses a multi-compartment electrolyzer (MCE) and isoelectric membranes to separate proteins based on charge. See Herbert, B., Righetti, P. G., Electrophoresis, 21, pp. 5641-5649 (2002). This isoelectric membrane technique, in combination with other separation techniques, allows for visualization of proteins, as a result of enhanced resolution, and to some extent, for the visualization of less abundant proteins, as a result of greater detection sensitivity. The isoelectric membrane technique, however, has significant disadvantages; it is relatively complex, requiring an electrode potential and specialized, expensive instrumentation, and is time-consuming, requiring up to twenty-four hours for completion.

Two-dimensional gel electrophoresis (2-DE) is an analytical technique that simultaneously separates thousands of proteins and allows comparative protein profiling between different crude biological samples. The existing 2-DE gel methods are incapable of detecting the majority of protein components in complex proteomes such as mammalian cells, tissues, and biological fluids. To increase the resolution of 2-DE separation, long Immobilized pH gradient (IPG) strips with narrow pH ranges have been designed. After separating the proteins by 2-DE, the resultant spots can be cut, destained, digested by trypsin, and analyzed by Matrix-Assisted Laser Desorption Ionization-Time of Flight-Mass Spectrometry (MALDI-TOF-MS). Tools like ExPASy, that scan the different protein databases available, allow for the identification of the protein based on its isoelectric point (pI), molecular mass (Mr), and the masses of the different peptides generated from the trypsin digestion of this protein. The pI and Mr can be estimated from the location of the spot on the gel. The masses of the peptide fragments are measured by MALDI-TOF-MS.

One of the main limitations that might hinder the identification of a protein separated by 2-DE is its low abundance in the sample. This limitation is a result of the finite protein loading limits on commercially available Immobilized pH Gradient (IPG) strips, where the first dimension of the separation occurs. The maximum protein load on an 11 cm IPG strip is less than 300 µg, but when an IPG strip (pH 7 to 10) is used, many proteins contained in the loading capacity, particularly those with pIs lower than 7 and higher than 10, will not be separated. Proteins outside the boundaries of the pH gradient will be electrostatically pushed to either end of the IPG strip because they remain net positively- or negatively-charged at every point of the IPG polyacrylamide gel. Since the proteins with pI values between 7 and 10 are a minority in the sample, many will be dragged by the overwhelming majority of proteins migrating to the ends of the strip. At the end of the separation, the amount of proteins profiled represents a fraction well below the original mass that was loaded.

SUMMARY OF THE INVENTION

Among the various aspects of the present invention is an improved process for the separation of one or more proteins from a sample containing a mixture of proteins. Advantageously, this process requires no specialized instrumentation, may be quickly performed, and may be carried out in non-denaturing conditions, allowing for further study of the separated proteins in their native form.

Briefly, therefore, the present invention is directed to a process for the separation of a protein from a sample containing a mixture of proteins. The process comprises combining the aqueous sample with an ion exchange material to form a first aqueous combination, the pH of the first aqueous combination being less than the pI of a first fraction of the proteins in the first aqueous combination but greater than the pI of a second fraction of the proteins in the first aqueous combination. The first aqueous combination is intensely mixed to cause protein comprised by one of said first and second fractions to bind to the ion exchange material, and the ion exchange material is then separated from the intensely mixed aqueous combination. If the protein(s) of interest (i.e., the protein(s) to be separated from the original mixture) is/are bound to the ion exchange material, the protein may then be released from the ion exchange material and, if desired, subjected to further purification. Alternatively, if the protein of interest remains in the aqueous supernatant after the ion exchange material is separated from the aqueous combination, the protein may be used, as is, or, if desired, subjected to further purification.

The present invention is further directed to a process for separating a protein from a sample containing a mixture of proteins, the process comprising: combining the aqueous sample with a cation exchange material or an anion exchange material to form a first aqueous combination, the pH of the first aqueous combination being (i) no more than 0.5 pH units greater than and no more than 5 pH units less than the pI of the protein when the ion exchange material is cation exchange material, and (ii) no more than 0.5 pH units less than and no more than 5 pH units greater than the pI of the protein when the ion exchange material is anion exchange material, mixing the first aqueous combination to cause the protein to bind to the ion exchange material; separating the mixed first aqueous combination into (i) a concentrated solids fraction containing the ion exchange material and a precipitate of the protein and (ii) an aqueous fraction, and recovering the protein from the concentrated solids fraction.

Other aspects and features of the invention will be, in part, apparent and, in part, pointed out hereinafter.

BRIEF DESCRIPTION OF THE DRAWINGS

FIG. 2 depicts the results of nonporous silica-reverse phase-HPIC-electrospray ionization-time of flight-mass spectrometry (i.e., NPS-RP-HPIC-ESI-TOF-MS), as described in Example 1. FIG. 2C is the deconvolution of the measured spectrum. The deconvolution parameters are: threshold 10% and resolution 1 Da.

FIG. 3 depicts the separation by 12% SDS polyacrylamide gels of fractions 1 to 4 from the chromatogram shown in FIG. 1, as described in Example 1. The gels of the highly concentrated fractions 1 and 2 were stained by coomassie blue. The gels for fractions 3 and 4, having a lower concentration, were silver stained.

FIG. 4C and FIG. 4D are computer enhanced to give a clearer image.

FIG. 5C and FIG. 5D are computer enhanced to give a clearer image.

FIG. 6A depicts the original 100 μg human plasma protein sample before the albumin elimination procedure. FIG. 6B depicts the combined 8 fractions collected after the 75% B and pH1 washes. FIG. 6C depicts the combined 4 fractions collected after the 90% B washes. FIG. 6D depicts the original 275 μg human plasma protein sample before the albumin elimination procedure. FIG. 6E depicts the combined 8 fractions collected after the 75% B and pH1 washes. The IPG strips used are 11 cm long, pH 4 to 7. The 10% gels used for SDS-PAGE in the second dimension of separation were silver stained. The pI range is shown at the bottom of the gels. The molecular masses (kDa) are labeled on the left of the gels.

Figure 10A:
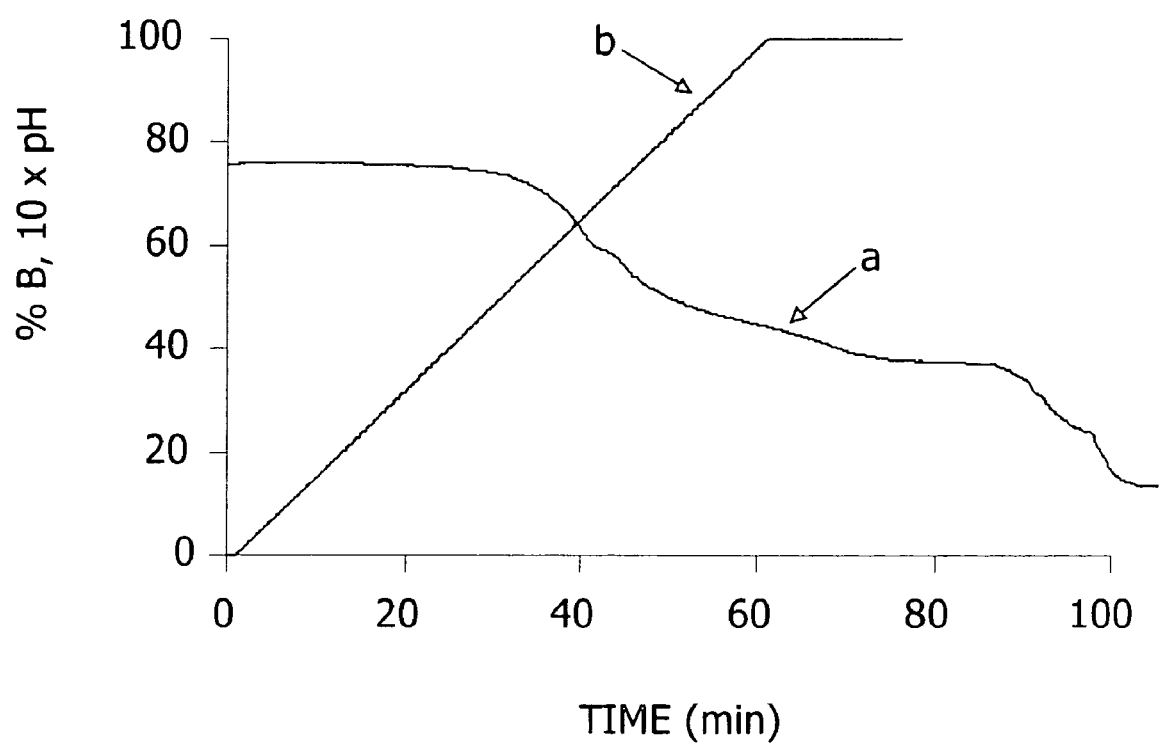
FIG. 10A depicts the pH gradient generated by titration of the anion exchange resin with buffers A and B as described in Example 3. Line (a) depicts the pH gradient of the eluted buffer and line (b) depicts the concentration of buffer B. FIG.
Figure 10B:
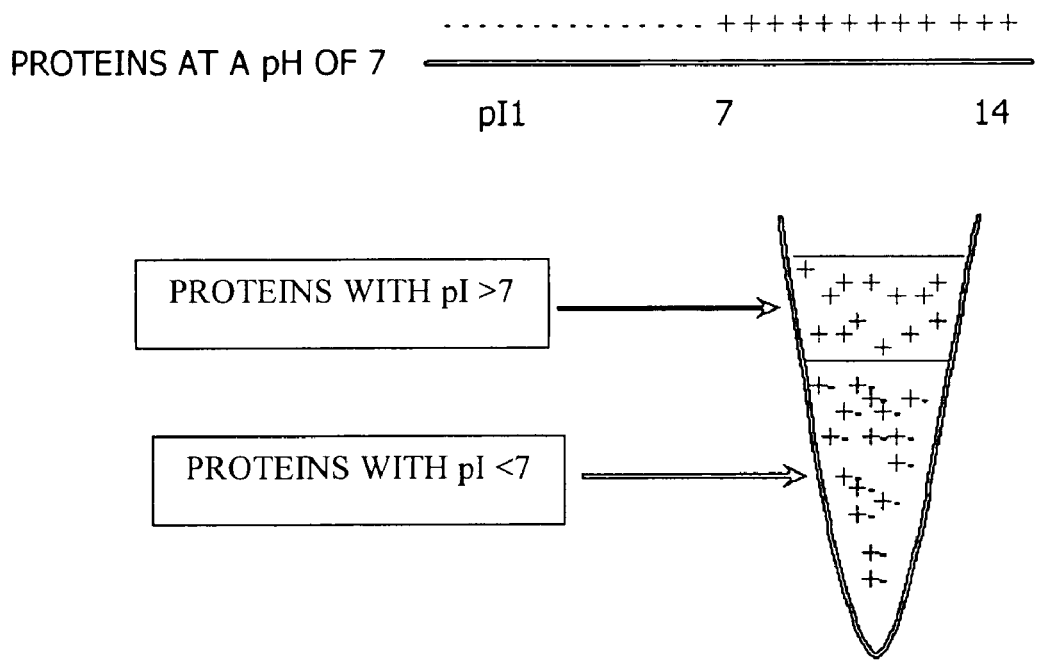
Figure 10C:
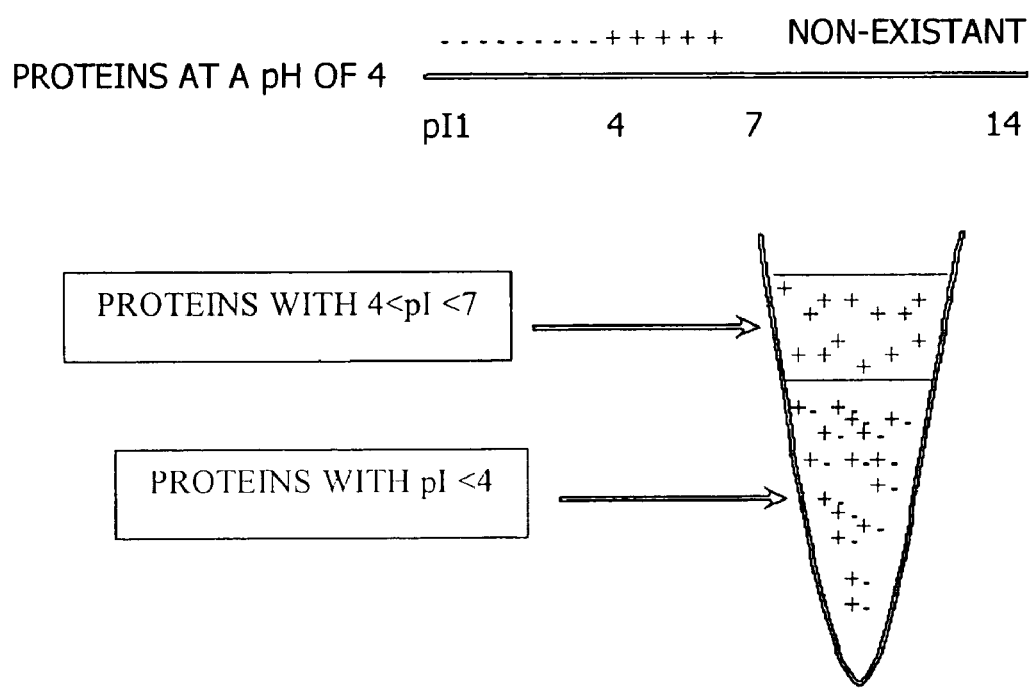

10B and FIG. 10C graphically depict the charge of proteins in solution at pH 7 and 4 during the prefractionation procedure described in Example 3.

Figure 11A:
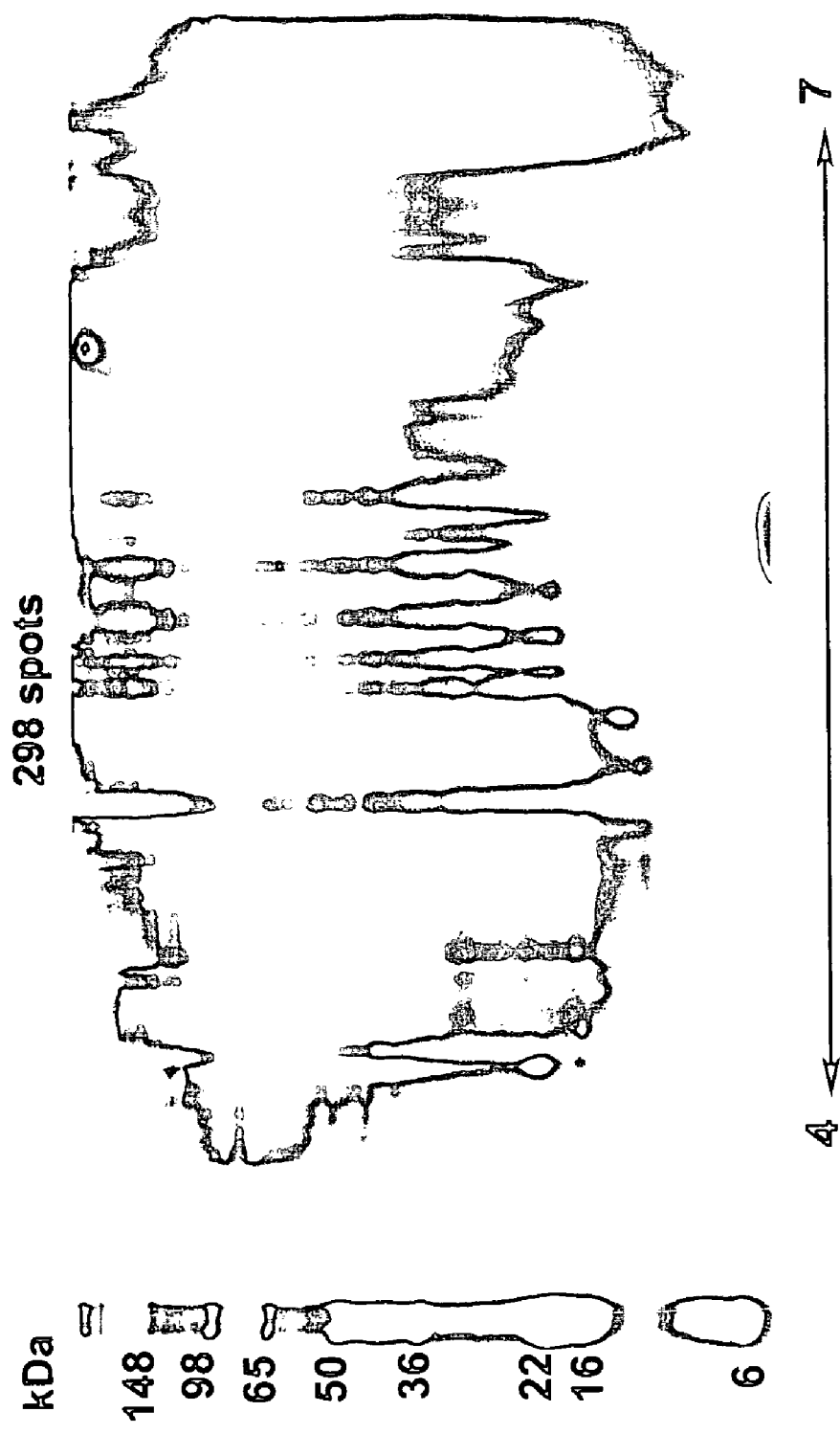
Figure 11B:
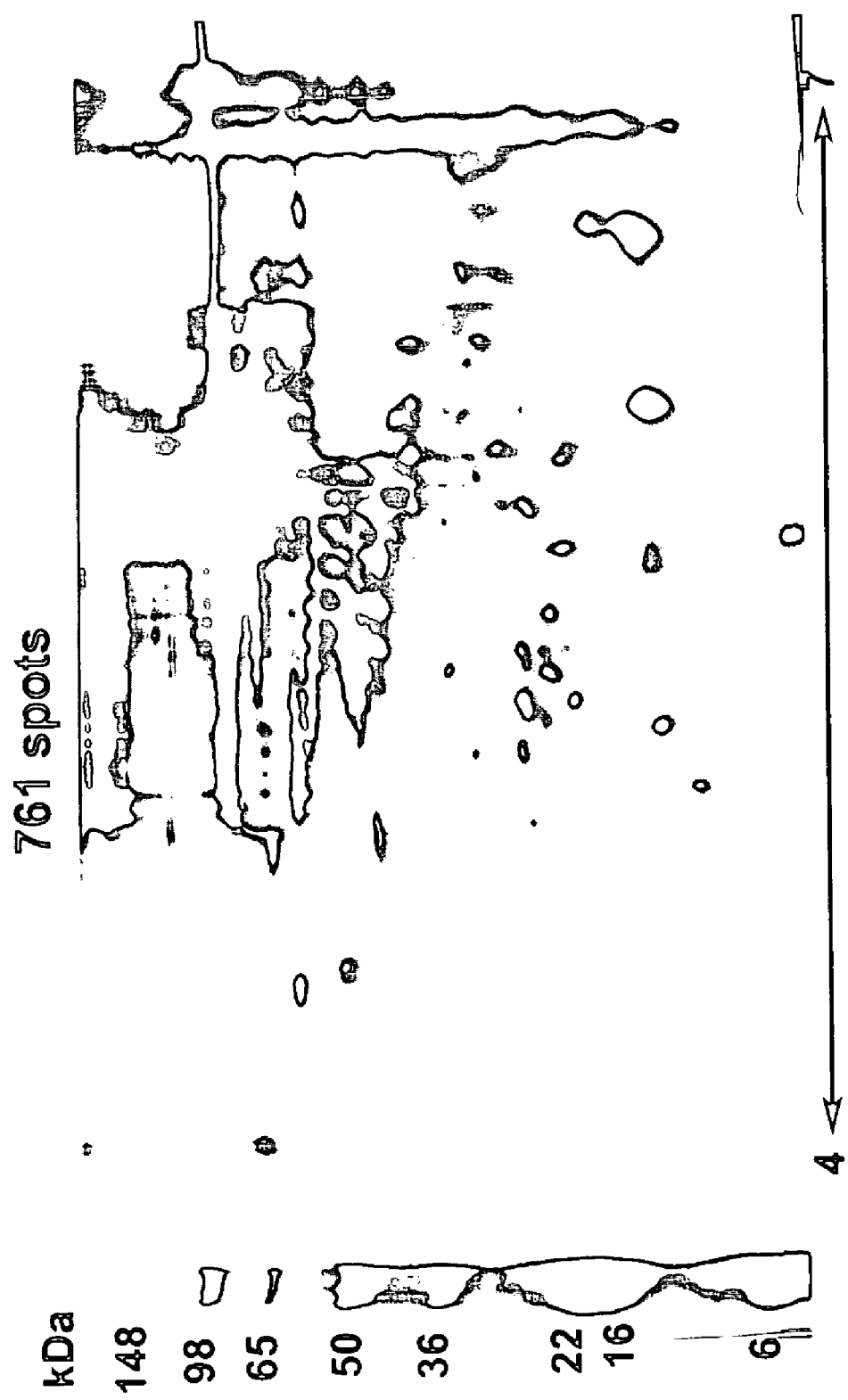

FIG. 11A-FIG. 11C depict the 2-dimensional gel electrophoresis of 250 μg whole cell lysate (FIG. 11A), 100 μg whole cell lysate (FIG. 11B), and 100 μg prefractionated cell lysate (FIG. 11C), as described in Example 3. The IPG strips used were 11 cm long, pH 4 to 7. The 10% polyacrylamide gels were silver stained.

Figure 12A:
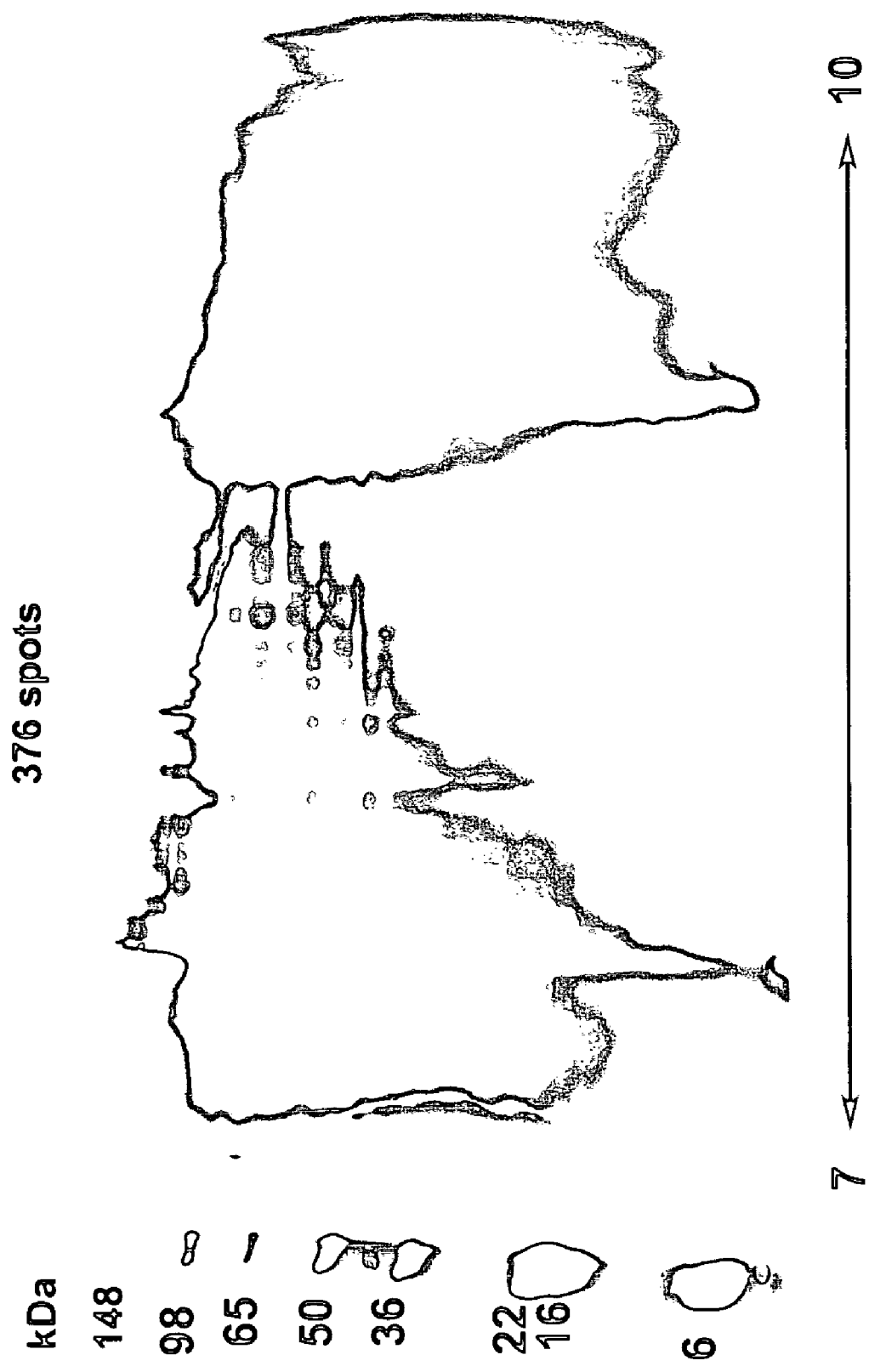
Figure 12B:
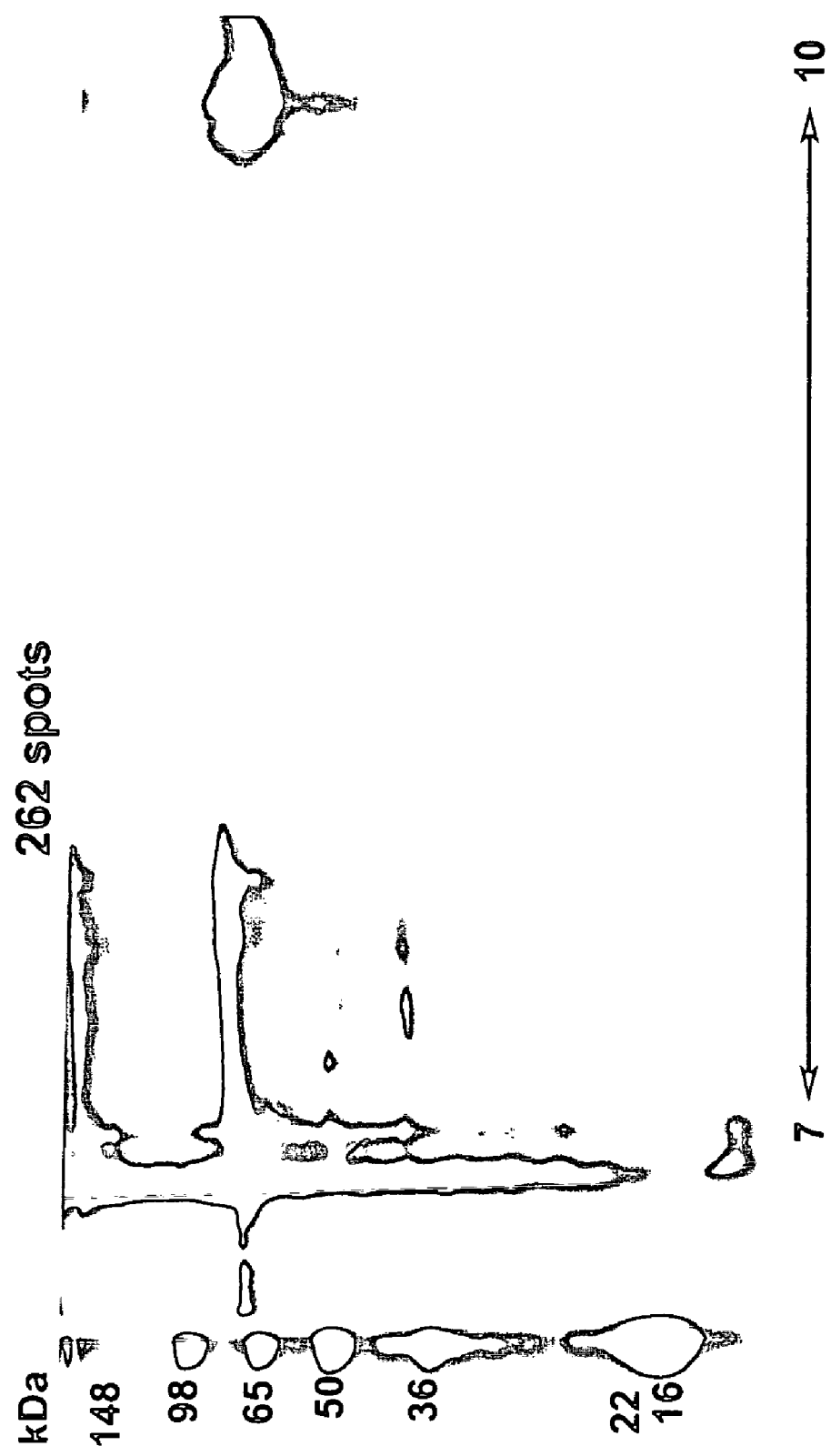
Figure 12C:
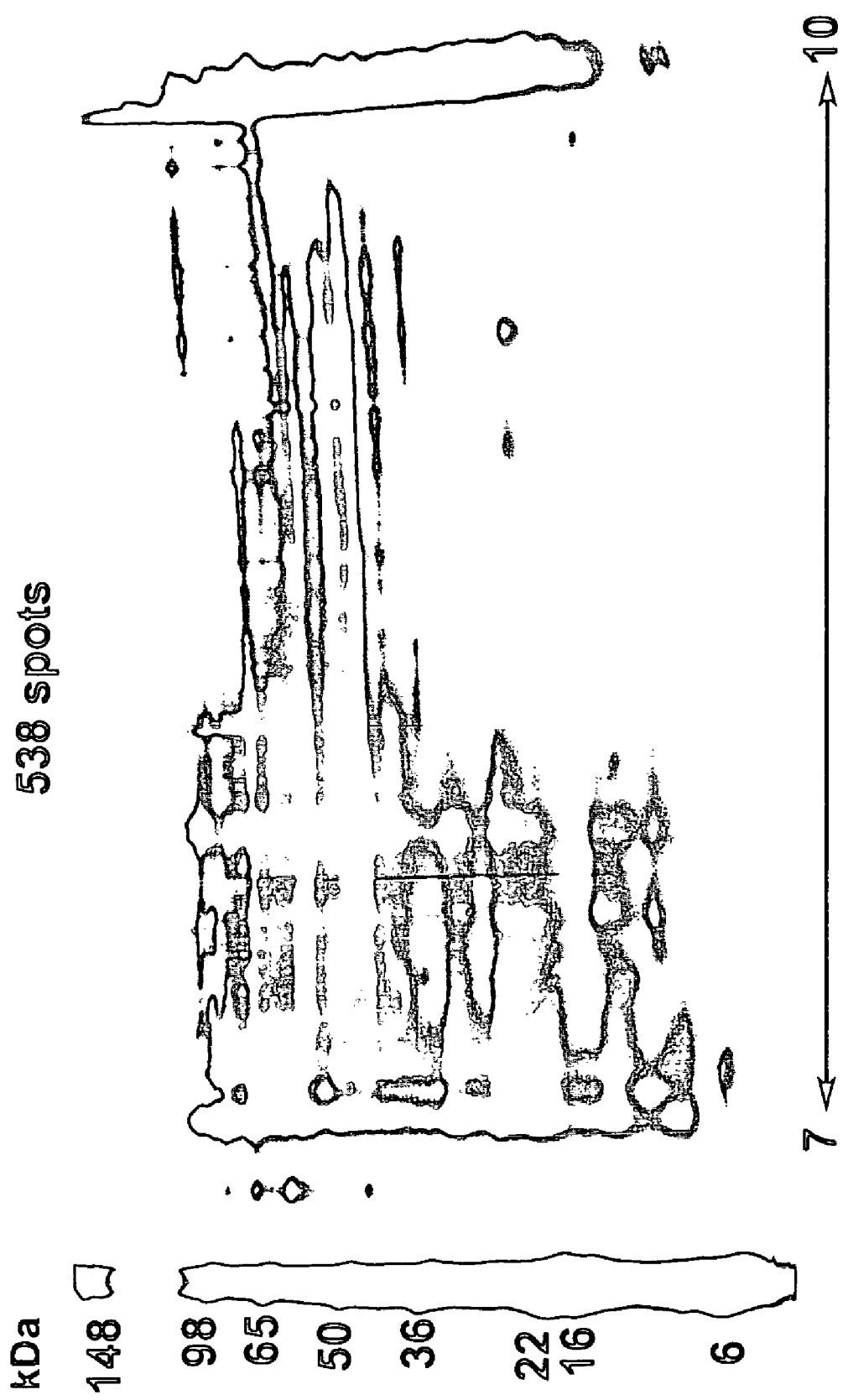

FIG. 12A-FIG. 12C depict the 2-dimensional gel electrophoresis of 250 μg whole cell lysate (FIG. 12A), 100 μg whole cell lysate (FIG. 12B), and 100 μg prefractionated cell lysate (FIG. 12C), as described in Example 3. The IPG strips used were 11 cm long, pH 7 to 10. The 10% polyacrylamide gels were silver stained.

Figure 13A:
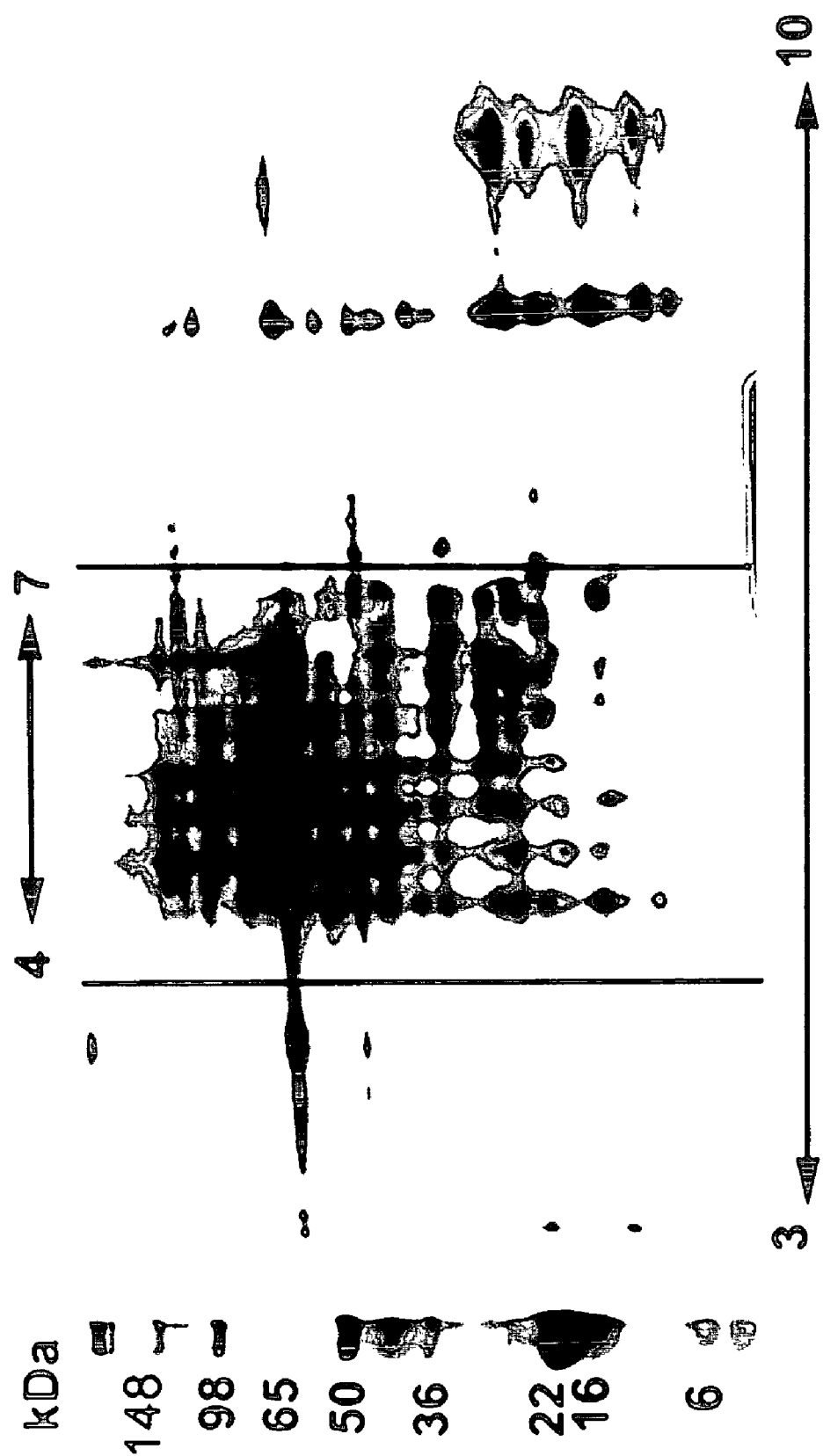
Figure 13B:
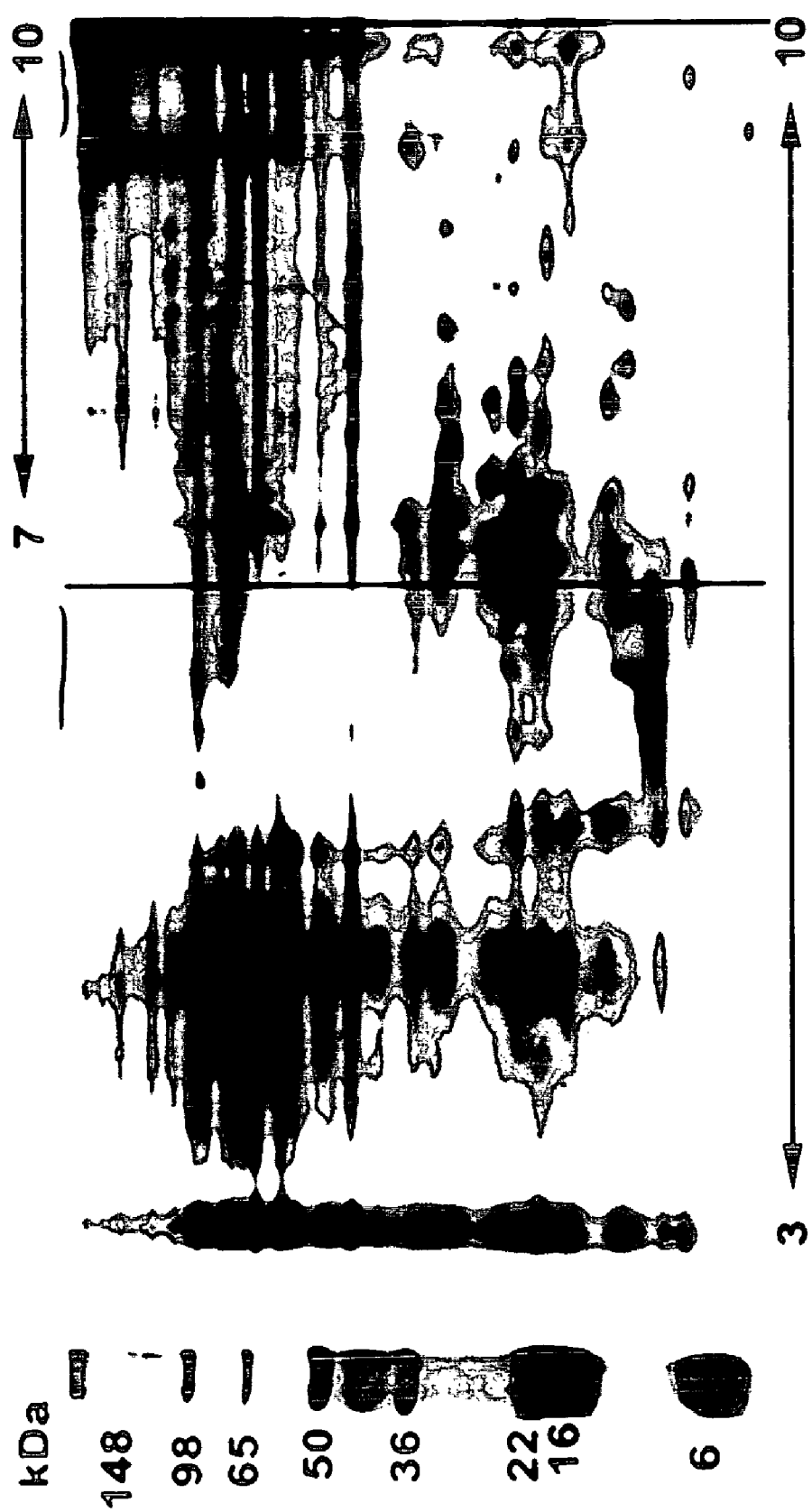

FIG. 13A and FIG. 13B depict the 2-dimensional gel electrophoresis of 100 μg cell lysate prefractionated to contain proteins with pIs between 4 and 7 (FIG. 13A), and 100 μg cell lysate prefractionated to contain proteins with pIs 7 or greater (FIG. 13B), as described in Example 3. The IPG strips used were 11 cm long, pH 3 to 10. The 10% polyacrylamide gels were silver stained.

Figure 14A:
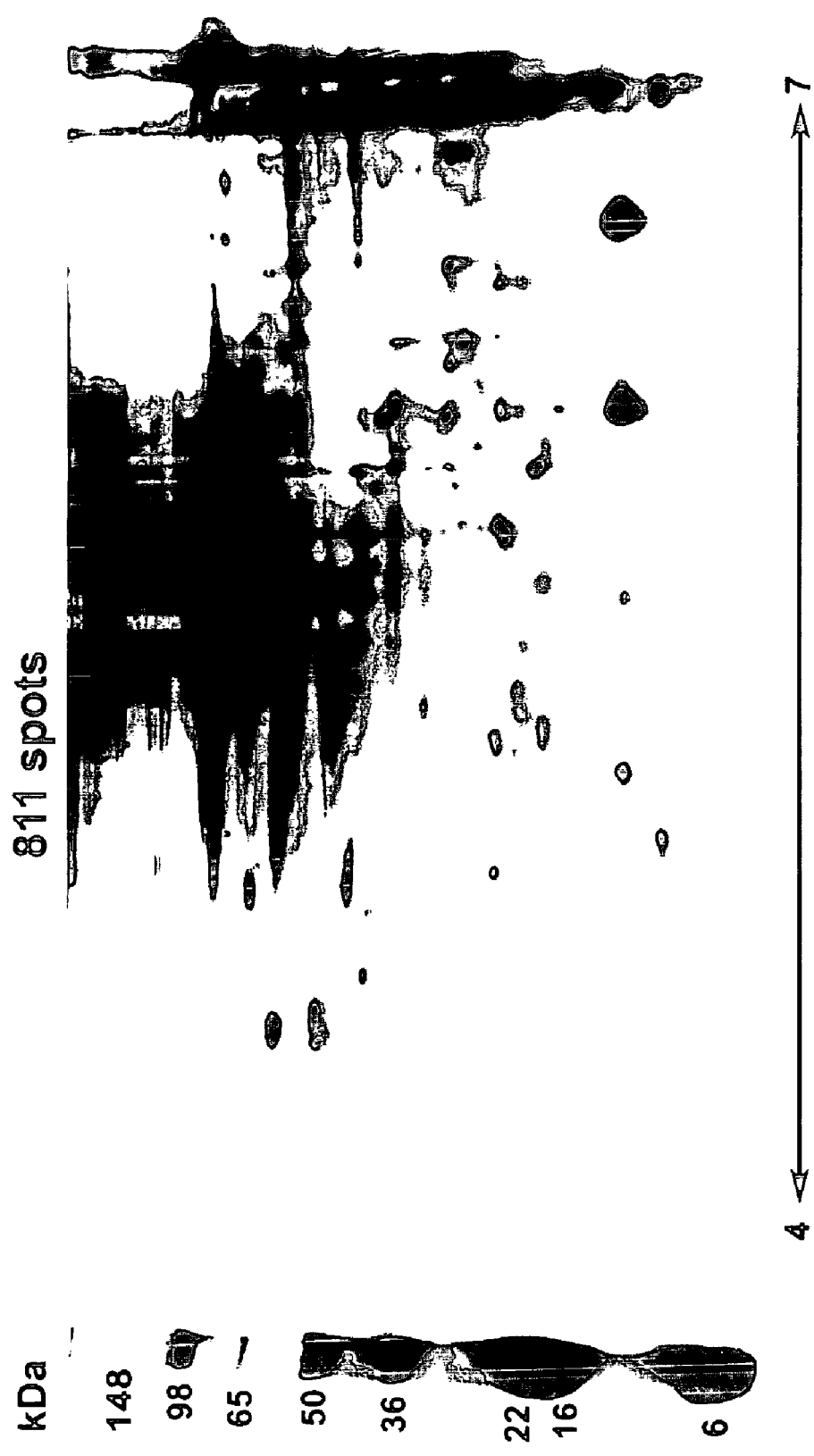
Figure 14B:
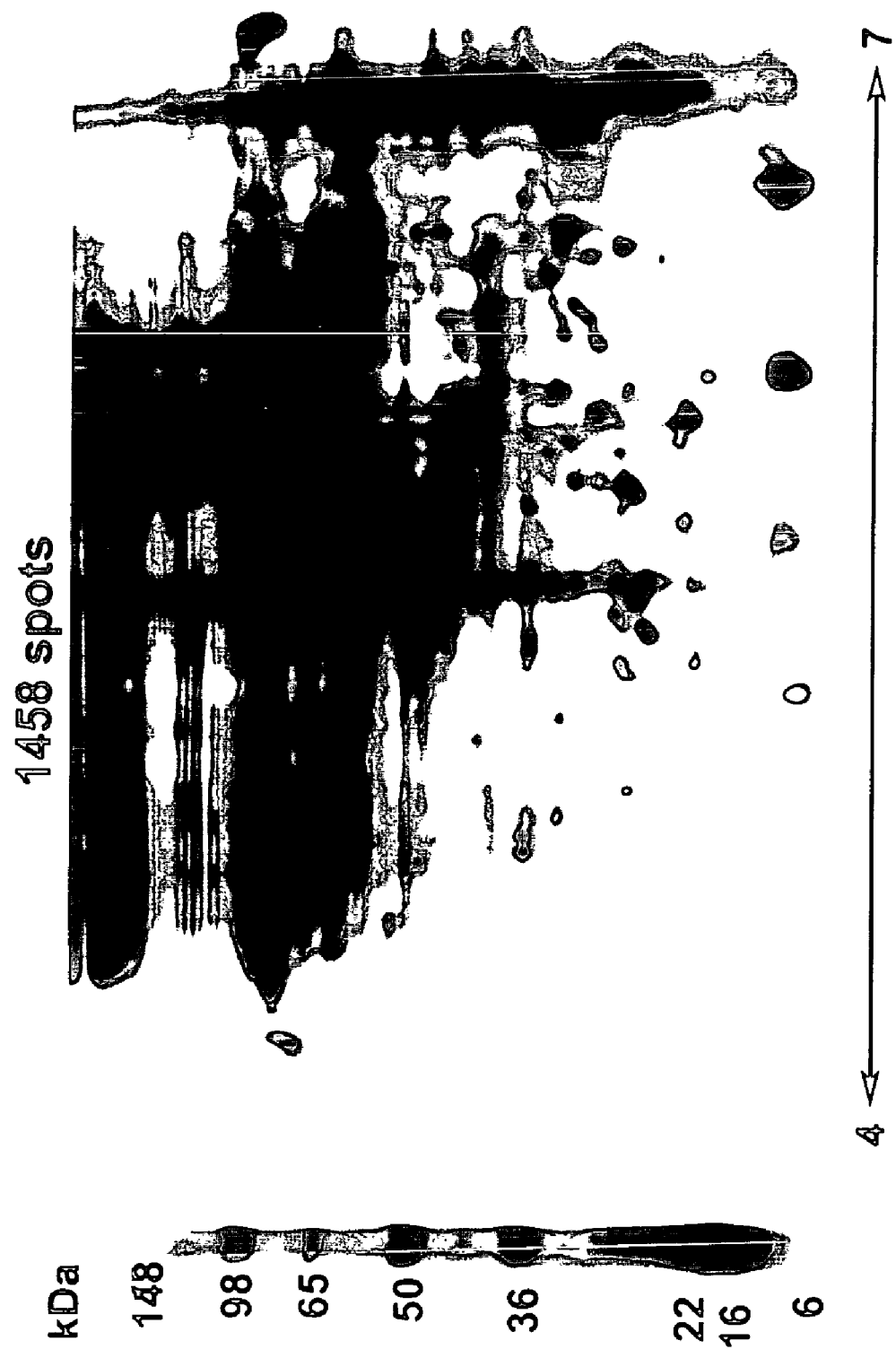

FIG. 14A and FIG. 14B depict the 2-dimensional gel electrophoresis of 100 μg whole cell lysate (from cells treated with EGCG) (FIG. 14A), and 100 μg prefractionated cell lysate (from cells treated with EGCG) (FIG. 14B), as described in Example 3. The IPG strips used were 11 cm long, pH 4 to 7. The 10% polyacrylamide gels were silver stained.

Figure 15A:
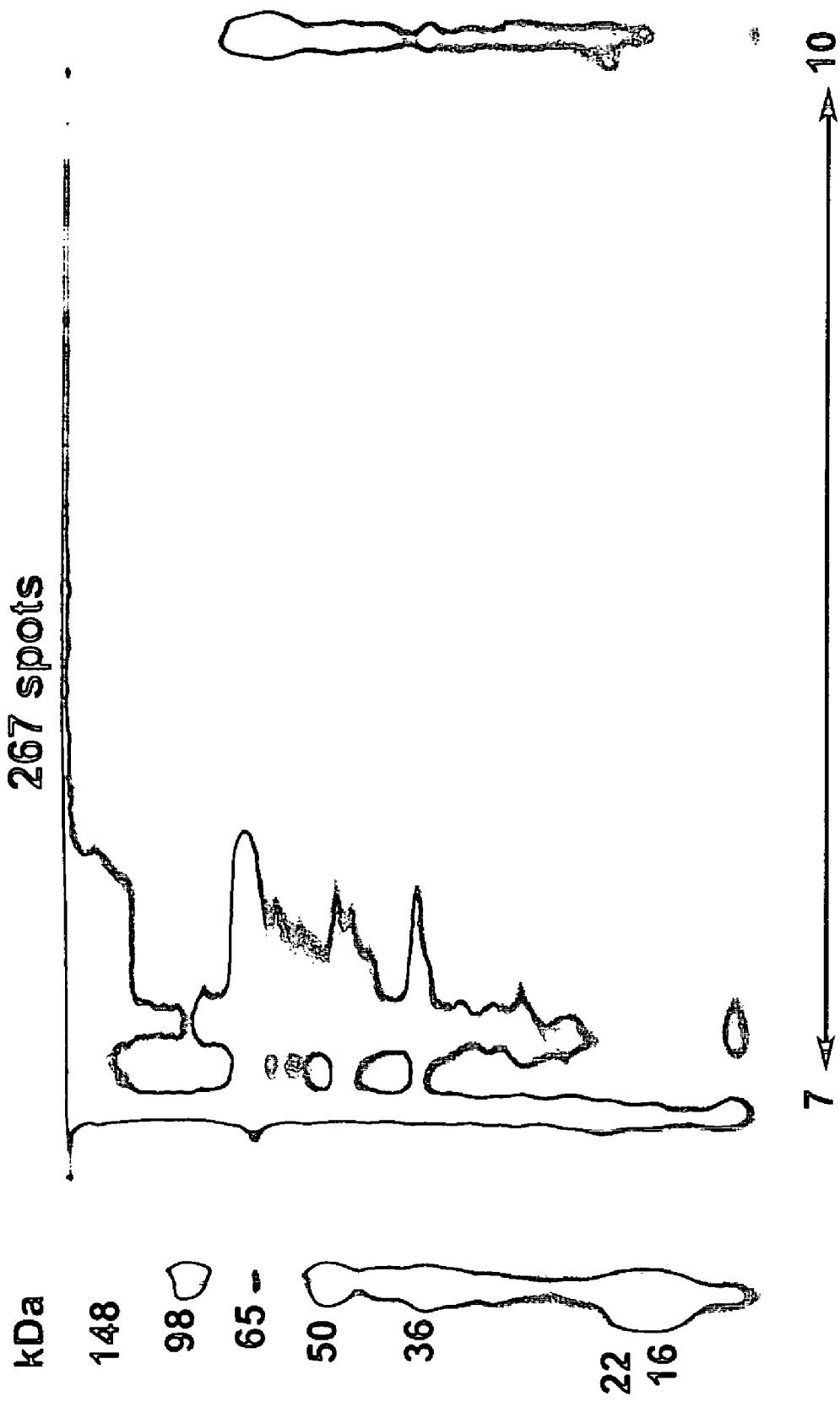
Figure 15B:
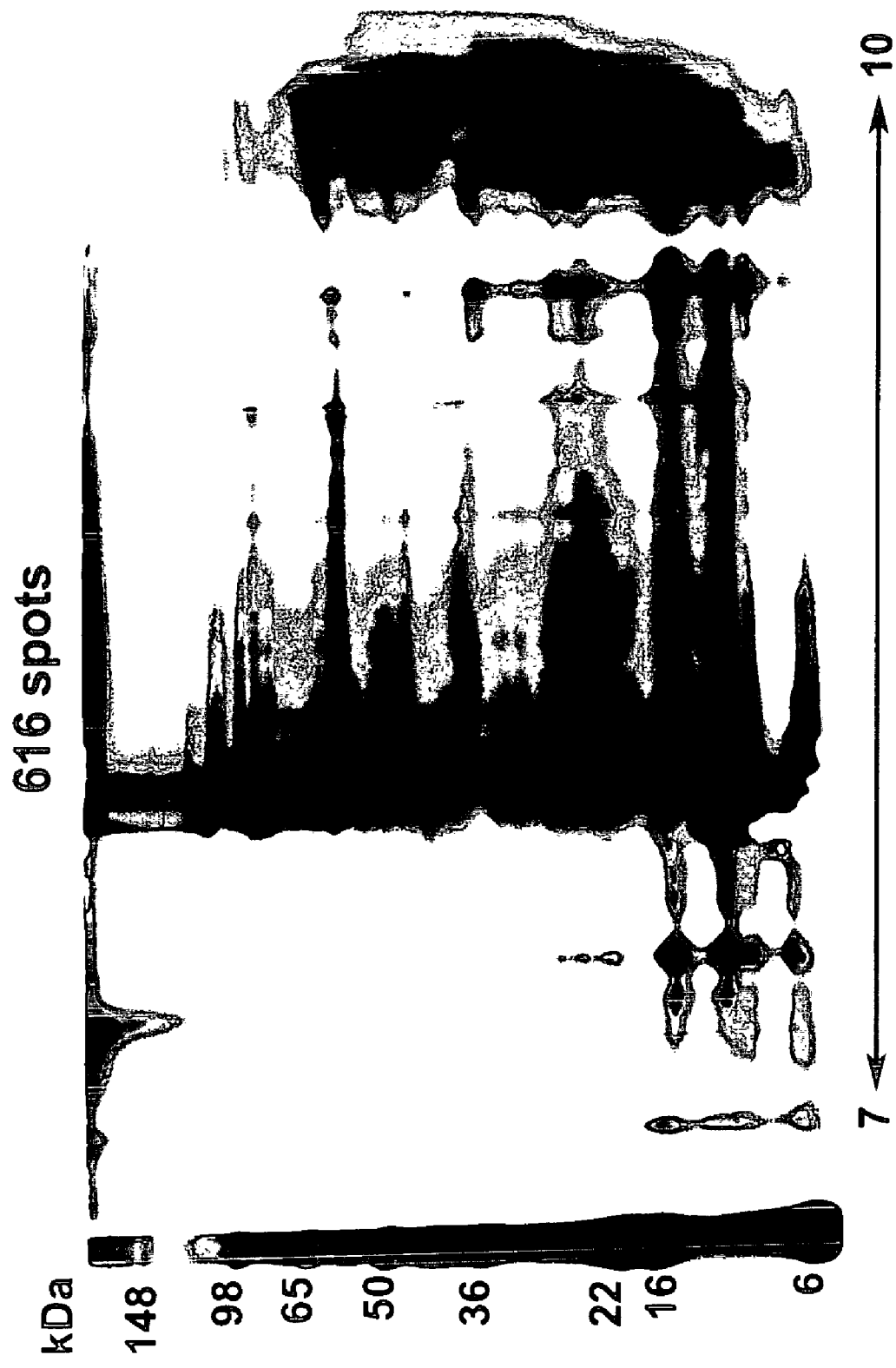

FIG. 15A and FIG. 15B depict the 2-dimensional gel electrophoresis of 100 μg whole cell lysate (from cells treated with EGCG) (FIG. 15A), and 100 μg prefractionated cell lysate (from cells treated with EGCG) (FIG. 15B), as described in Example 3. The IPG strips used were 11 cm long, pH 7 to 10. The 10% polyacrylamide gels were silver stained.

DETAILED DESCRIPTION OF THE INVENTION

In general, the present invention enables a convenient and relatively rapid separation of one or more proteins from an aqueous sample mixture by using ion exchange materials, adjusting the pH of the sample, as necessary, so that a fraction of the proteins in the mixture have an affinity for the ion exchange material whereas another fraction of the proteins in the mixture do not, and intensely mixing the sample with the ion exchange resin to promote the rapid binding of one of the two fractions to the ion exchange material. Advantageously, this process may be carried out in a matter of minutes using conventional laboratory equipment.

A protein is an amphoteric molecule, meaning that it can carry a positive, negative, or zero net charge (the net charge being the sum of all the negative and positive charges of the amino acid side chains and amino and carboxyl termini), depending upon the pH of its environment. The specific pH at which the net charge of the protein is zero is also known as the protein's isoelectric point (pI). When a protein is an aqueous environment having a pH value less than the pI value of the protein, the protein is positively charged. Conversely, when a protein is in an aqueous environment having a pH value greater than the pI value of the protein, the protein is negatively charged. Thus, by adjusting the pH of a protein's local environment, one can manipulate the protein's charge and its affinity for ion exchange resin. For example, a protein in an environment that has a pH value below the protein's pI will have a net positive charge and will bind to a cation exchange material but will have little or no affinity for an anion exchange material. Similarly, a protein in an environment that has a pH value above the protein's pI will have a net negative charge and will bind to an anion exchange material, but will have little or no affinity for a cation exchange material. A protein in an environment that has a pH value equal to its pI will have a net zero charge and will have little or no affinity to either anionic or cationic exchange resin.

Many proteins, including albumin, a protein that may be found in a variety of biological samples but is particularly abundant in plasma (constituting more than 50% of total plasma proteins), are relatively insoluble at pH values near the protein's pI value; unless a protein has a relatively high solubility, it will typically precipitate from aqueous solutions having a pH within 0.5 pH units of the protein's pI value. Thus, for example, albumin and similarly behaving proteins tend to precipitate from aqueous solutions having a pH value approximately equal to their respective isoelectric points.

Figure 9:
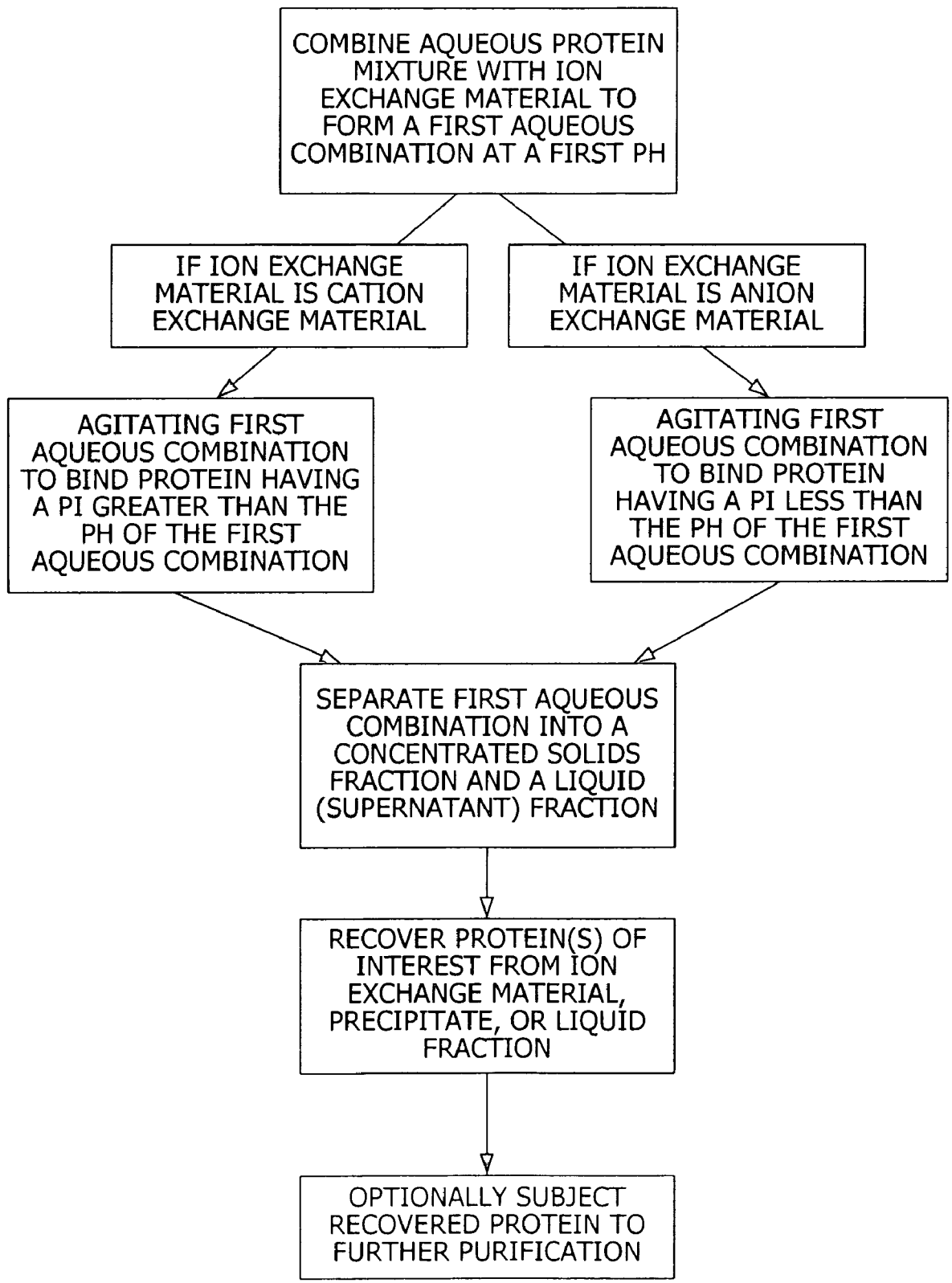
FIG. 9 is a schematic series of steps comprising one embodiment of the present invention.

Referring now to FIG. 9, these principles are employed in the process of the present invention to facilitate the separation of a protein from an aqueous sample containing a mixture of proteins. In a first step (Step 1), the aqueous sample is combined with an ion exchange material to form an (a first) aqueous combination at a (first) pH. Optionally, a buffer or buffer system is added to control the pH. Advantageously, depending upon whether it is desired to have the protein of interest (i.e., the protein to be separated from the mixture) bound to the ion exchange material, or in solution, anion or cation exchange material may be used. If cation exchange material is used in a second step (Step 2), intense mixing of the combination causes (i) protein(s) having a pI greater than the pH of the combination to bind to the cation exchange resin, (ii) protein(s) having a pI value approximately equal to the pH of the combination to precipitate, and (iii) protein(s) having a pI less than the pH of the combination to remain dissolved in the aqueous solution. Alternatively, if anion exchange material is used in a second step (Step 2), intense mixing of the combination causes (i) protein(s) having a pI less than the pH of the combination to bind to the anion exchange resin, (ii) protein(s) having a pI value approximately equal to the pH of the combination to precipitate, and (iii) protein(s) having a pI greater than the pH of the combination to remain dissolved in the aqueous solution. After mixing is complete and protein(s) is/are bound to the ion exchange material, the combination is separated in a third step (Step 3) into a concentrated solids fraction (containing the ion exchange material and any precipitate) and an aqueous (supernatant) fraction; for example, the ion exchange material may simply be filtered or centrifuged from the combination. In a fourth step (Step 4), the protein(s) of interest (whether in the concentrated solids fraction or liquid fraction) is/are recovered and optionally, used as-is or subjected to further purification in a fifth step (Step 5). If the protein(s) of interest are in the solids fraction (as a precipitate or a species bound to the ion exchange resin), the recovery step (Step 4) preferably includes re-dissolving the protein(s) of interest after the solids fraction has been separated from the liquid fraction. Thus, for example, in the recovery step the solids fraction may be combined with an aqueous solution, preferably a buffered solution, having (i) a pH up to about 1 pH unit greater than the pI of the protein of interest when the ion exchange resin is cation exchange resin or (ii) a pH up to about 1 pH unit less than the pI of the protein of interest when the ion exchange resin is anion exchange resin.

In a preferred embodiment, the pH of the aqueous combination and the type of ion exchange material (anion or cation) are selected to cause a fraction of the protein(s) of interest to bind to the ion exchange material and another fraction of the protein(s) to form a precipitate during the intense mixing step (Step 2). This may be achieved, for example, by selecting a pH for the aqueous combination which is (i) no more than about 0.5 pH units less than the pI of the protein of interest when the ion exchange material is anion exchange material and (ii) no more than 0.5 pH units greater than the pI of the protein of interest when the ion exchange material is cation exchange material. In addition, to enhance selectivity, the pH selected for the aqueous combination is preferably within 5 pH units, more preferably within 0.5 pH units, and still more preferably within 0.2 pH units of the pI of the protein; that is, when the ion exchange material is anion exchange material, the pH of the aqueous combination is preferably no more than 0.5 pH units less than and no more than 5 pH units greater than the pI of the protein of interest, and when the ion exchange material is cation exchange material, the pH of the aqueous combination is preferably no more than 0.5 pH units greater than and no more than 5 pH units less than the pI of the protein of interest.

When the ion exchange material is anion exchange material the pH of the aqueous solution is preferably between about 0.5 pH units less than the pI of the protein of interest and about 5 pH units greater than the pI of the protein of interest, more preferably, the pH is between about 0.2 pH units less than the pI of the protein of interest and about 1 pH unit greater than the pI of the protein of interest.

When the ion exchange material is cation exchange material the pH of the aqueous solution is preferably between about 5 pH units less than the pI of the protein of interest and about 0.5 pH units greater than the pI of the protein of interest, more preferably, the pH is between about 1 pH unit less than the pI of the protein of interest and about 0.2 pH units greater than the pI of the protein of interest.

Although a range of conventional ion exchange materials are commercially available and compatible with the process of the present invention, it is generally preferred that the ion exchange material be in the form a particulate ion exchange resin. In this embodiment, the aqueous combination may alternatively be referred to as an aqueous dispersion (e.g., a dispersion of resin particles in an aqueous solution) and, this terminology is used elsewhere herein to describe this preferred embodiment. Having the ion exchange material in particulate form readily facilitates intense mixing. That is, the intense mixing step (Step 2) may be carried out using a vortex, magnetic stirrer or other intense mixing device operated at a sufficient speed (revolutions per minute, "rpm") to cause a vortex to form in the liquid. Preferably, the cavity in the center of the swirling liquid extends at least 40%, preferably 50%, preferably at least 75%, still more preferably at least 90%, and still more preferably at least 99% of the distance from the surface of the liquid to the bottom of the container. Stated differently, the depth of the "v" of the vortex is at least 40%, preferably 50%, preferably at least 75%, still more preferably at least 90%, and still more preferably at least 99% of the depth of the column of liquid at the perimeter of the container.

If further purification is desired, Steps 1-4 for may be repeated, but in the second iteration of these steps, a (second) aqueous combination is prepared by combining the concentrated solids fraction or the liquid fraction derived from the prior (first) iteration of the steps with an ion exchange material (which may be the same or different, even a different type than that used in the previous iteration) at a (second) pH in Step 1 wherein the second pH differs from the first pH by at least 0.2 pH units. In this manner, the protein(s) obtained in the concentrated solids fraction or the liquid fraction from the first iteration of Steps 1-4 may be further fractionated based upon the pI of the protein(s) in the fraction. Extending this approach, if further purification is desired, Steps 1-4 for may be repeated, but in the third and each successive iteration of these steps, a (third and successive) aqueous combination is prepared by combining the concentrated solids fraction or the liquid fraction derived from the prior iteration of the steps with an ion exchange material (which may be the same or different, even a different type than that used in the previous iteration) at a (third and successive) pH in Step 1 wherein each successive pH differs from the previous pH by at least 0.2 pH units. For example, in one preferred embodiment, Steps 1-4 are carried out three times, each time under different conditions to yield three different liquid or concentrated solids fractions: one containing proteins with pI's greater than 7, another with proteins having pI's between 4 and 7, and a third with proteins having pI's less than 4. This example is further described in Example 3 and illustrated in FIGS. 10B and 10C.

In one alternative embodiment, the sequence of steps (Steps 1-4) are carried out using both cation and anion exchange material. Because the two have an affinity for each other, it is preferred that contact between the two be minimized. Thus, for example, the aqueous combination is at a pH which induces (i) protein(s) having a pI greater than the pH of the combination to bind to the cation exchange material, (ii) protein(s) having a pI value approximately equal to the pH of the combination to precipitate, and (iii) protein(s) having a pI less than the pH of the combination to bind to the anion exchange material. By selecting a buffer having a desired pH, therefore, proteins whether in the form of a precipitate or bound to the cation or anion exchange material may be selectively re-dissolved into an aqueous solution and thus separated from the other proteins. By selecting multiple buffers (or pH's), a series of proteins may be selectively re-dissolved, thus effectively fractionating the original protein mixture into a plurality of products. To minimize contact between the anion and cation exchange materials, the two may be in different formats (e.g., one in the form of a particulate resin and the other in the form of a membrane or other non-particulate form) or the two may be in the same form (e.g., each in particulate form) but some measure (e.g., a membrane or other physical barrier) is used to minimize contact between the anion and cation exchange materials.

The process of the present invention provides several advantages. For example, the intense mixing and separation steps require no expensive, specialized instrumentation and can be quickly performed using, for example, a vortex mixer and a centrifuge, respectively. Additionally, the process of the present invention can be carried out in non-denaturing conditions, allowing for the separated proteins to be further studied. More specifically, separating proteins into fractions based on the pI's of the proteins allows for increased sample loading (in the first dimension) on two-dimensional gels that utilize narrow immobilized pH gradient (IPG) strips in the first dimension of the separation, because proteins having pI's outside the pH range of a particular strip are excluded. Increased sample loading results in the enhanced resolution and visualization of proteins. In the same vein, increased sample loading allows for the visualization of less abundant proteins, like biomarkers for cancer and other diseases, as a result of greater detection sensitivity.

To improve the yield of protein in the liquid fraction the ion exchange resin may be washed with aqueous solution. Preferably, the washing solution is at about the same pH as first (or previous) aqueous combination. The washing step includes adding an aqueous washing solution to the ion exchange resin from step 4, intensely mixing the combination, separating the aqueous fraction and solids fraction, and recovering the liquid fraction from the ion exchange material. The washing step may be repeated as desired. In one embodiment the washing step was repeated three to four times.

Sample

The processes described herein may be used to separate a protein from any sample. In general, the sample may be any biological sample that contains proteins, peptides, amino acids, and/or charged molecules. For example, the biological sample may be tissue lysate, cell lysate, bacteria lysate, serum, plasma, any bodily fluid, whether secreted (saliva) or non-secreted (cerebral spinal fluid), protein extracts from bio-organisms, or a purified derivative thereof. For example, the biological sample may be a cell lysate that has undergone differential centrifugation or filtration in order to remove subcellular fragments produced during lysis of the cell or, in the case of plasma, the protein source may be plasma proteins that have been separated into one of five fractions, Fraction I, Fraction II+III, Fraction IV1, Fraction IV4, and Fraction V, using the Cohn, cold ethanol precipitation, method.

In one example the biological sample comprises cell lysate from a human prostate cancer cell line, LNCaP cell lysate.

Separation Using an Anion Exchange Resin

In certain embodiments, the separation is performed using an anion exchange material in the form of a particulate anion exchange resin. An anion exchange resin may be used to perform a variety of separations, including (i) separating a fraction of proteins with a pI that is greater than the pI of a different fraction of proteins from the sample; (ii) separating a fraction of proteins with a pI that is less than the pI of a different fraction of proteins from the sample; and/or (iii) separating a fraction of proteins with a pI that is greater than the pI of a fraction of proteins and less than the pI of a different fraction of proteins from the sample.

To separate one or more proteins of a protein mixture in an aqueous sample, the sample and anion exchange material are combined to form a first aqueous combination; preferably, the ion exchange material is in the form of a resin and the aqueous combination is an aqueous dispersion of the particulate resin in the sample. In this embodiment, the first aqueous dispersion is formed at a pH which is less than the pI of a fraction of the proteins in the first aqueous dispersion but greater than the pI of a different fraction of the proteins in the first aqueous dispersion. Preferably the anion exchange resin is capable of free-flowing movement relative to the rest of the dispersion, as discussed below, and may advantageously first be equilibrated to the pH of the first aqueous dispersion prior to performing the separation.

The pH at which the first aqueous dispersion is formed may vary depending on the desired separation. For instance, if a fraction of proteins with a pI greater than the pI of a different fraction of proteins in the sample is to be separated from the sample, it may be advantageous to form the first aqueous dispersion at a pH at which the proteins to be separated from the sample will have a positive charge and will thus not bind to the anion exchange resin, as discussed below. For example, in one embodiment, proteins with pI's greater than about 7.0 may be separated from the sample. For this separation, the first aqueous dispersion may advantageously be formed at a pH of about 6.0 to about 7.0. Under these conditions, proteins with pI's greater than about 7.0 are positively charged and do not bind to the anion exchange resin, while proteins with pI's less than about the first pH (e.g. 7.0) are negatively charged and bind to the anion exchange resin. Proteins with pI's of about the first pH (e.g. 7.0) would have a zero net charge. In some instances, such proteins may precipitate from solution. In other instances, e.g., in the case of highly soluble proteins, such proteins may be found in solution.

In yet another alternative, it may be desirable to separate a fraction of proteins with a pI greater than the pI of one fraction of proteins in the sample and less than the pI of a different fraction of proteins in the sample from the sample. In this instance, the pH at which the first aqueous dispersion is formed is preferably such that proteins with pI's greater than the pI of the protein fraction to be separated are positively charged and thus do not bind to the anion exchange resin. For example, if a fraction of proteins with a pI in the range of about 4.0 to about 7.0 is to be separated from a sample, the first aqueous dispersion may advantageously be formed at a pH of about 6.0 to about 8.0. (See Example 3 and FIGS. 10B and 10C.)

Mixing an aqueous dispersion increases the probability of contact between ion exchange materials, i.e., ion exchange resin, and the proteins and allows for a more uniform distribution of any buffer or agent used to adjust the pH, which therefore may result in a more uniform pH throughout the dispersion. Preferably, the aqueous dispersion is mixed to result in turbulent flow of the sample throughout or relative to the ion exchange material. This is particularly preferred when the ion exchange material is in a format other than a free-flowing particulate resin, as discussed below. The intense mixing induces or at least better facilitates one of the protein fractions to bind to the ion exchange material. For example, if an anion exchange resin is used, proteins having pI's less than the pH of the aqueous dispersion (i.e., negatively charged proteins) will bind to the anion exchange resin.

It will be recognized that the degree of separation is a function of the intensity of mixing as well as time. For example, if an aqueous dispersion is only gently mixed, longer mixing times will be required to obtain the same degree of separation that a more intense mixing would provide in less time. Thus, intense mixing can substantially decrease the amount of time required to obtain the desired degree of separation. Suitable methods known in the art may be used to intensely mix the aqueous dispersion: for example, the aqueous dispersion may be vigorously shaken by hand, shaken using a shaker, including a vertical, horizontal, or orbital shaker, or vortexed in that speeds of at least about 100 cycles or rpm are used. Preferably the speed of shaking is greater than 100 cycles or rpm, more preferably 200 cycles or rpm, more preferably 300 cycles or rpm up to the limits of the equipment used. Preferably, the aqueous dispersion is vortexed. The vortexing may be performed at any suitable speed and preferably is done at a speed of at least 200 rpm, more preferably at a speed of at least 500 rpm, still more preferably at a speed of at least about 1000 rpm. Typically, speeds in excess of about 5,000 rpm will not be employed with speeds in the range of about 800 rpm to about 1200 rpm being typical. Although there is generally no upper time limit on the length of time an aqueous dispersion is intensely mixed, it is preferable that an aqueous dispersion is intensely mixed for between about 10 seconds and several hundred seconds (e.g., about 300 seconds); typically, the aqueous dispersion will be vortexed for a period of about 20 to 50 seconds. In one embodiment, for example, the aqueous dispersion is vortexed at a speed of about 1000 rpm for about 30 seconds.

After an aqueous dispersion is intensely mixed, the aqueous dispersion may also be centrifuged and the supernatant recovered. Centrifugation separates mixed samples into homogenous component layers by spinning them at a high speed. In the present case, centrifugation causes an intensely mixed aqueous dispersion to stratify into a concentrated solids fraction and a supernatant, the supernatant comprising the fraction of the proteins which did not bind to the ion exchange material and the concentrated solids fraction comprising precipitate. When the ion exchange material is in the form of free-flowing ion exchange resin, the concentrated solids fraction also contains ion exchange resin. For example, when the ion exchange resin is an anion exchange resin, the supernatant will comprise positively charged proteins that have pI's greater than the pH of the aqueous dispersion, and proteins with pI's less than the pH of the aqueous dispersion will be negatively charged and will therefore be bound to the anion exchange resin.

The length of time an aqueous dispersion is centrifuged is dependent on the speed of the centrifugation. For example, an aqueous dispersion that is centrifuged at a low speed is typically centrifuged for a longer period of time in order to obtain a comparable degree of separation as would be obtained were the aqueous dispersion centrifuged at a greater speed for a shorter period of time. In general, as the centrifugation speed increases, the time required to obtain a desired degree of separation decreases. Preferably, the intensely mixed aqueous dispersion is centrifuged at a force of at least 500×g, more preferably at a force of at least 1000×g, and still more preferably at a force of about 2000 to about 8000×g; typically, the material will be centrifuged at a force of about 4000 to about 6000×g, and even more typically at a force of about 5000×g. In general, the material may be centrifuged for any length of time which does not degrade the protein; typically, centrifuge times will be in the range of about 10 to about 300 seconds. For example, in one embodiment, the aqueous dispersion is centrifuged at a force of about 4000-6000×g for about 30 seconds.

The supernatant may then be separated from the concentrated solids fraction by a suitable means known in the art. For example, in one embodiment, the supernatant is separated from the concentrated solids fraction by decanting the supernatant. In another embodiment, the supernatant is separated from the concentrated solids fraction by filtration.

If desired, several separations may be performed to recover a particular protein fraction with a particular pI from the sample. Generally, when more than one separation is performed, a second aqueous dispersion comprising the anion exchange resin (to which are bound proteins with pI's less than the pH of the first aqueous dispersion) is formed at a pH at which at least a fraction of the proteins bound to the anion exchange resin is released from the resin. This step is followed by mixing, preferably intense mixing, of the second aqueous dispersion, as described above; centrifuging of the intensely mixed second aqueous dispersion, as described above, to cause the second aqueous dispersion to stratify into a second concentrated solids fraction and a second supernatant, the second supernatant comprising the fraction of the proteins that was released from the resin; and separating the second supernatant from the second concentrated solids fraction.

The pH at which the second aqueous dispersion is formed may vary depending on the desired separation. Preferably, the second aqueous dispersion is formed at a pH that is less than the pH at which the first aqueous dispersion was formed. As the pH is decreased, proteins bound to the anion exchange resin are released from the resin. It is generally advantageous to form the second aqueous dispersion at a pH only as low as necessary to release only proteins with pI's above a selected target pI from the resin (i.e., positively charged proteins), while proteins with pI's below the target pI remain bound to the anion exchange resin. For example, if a fraction of proteins with a pI in the range of about 4 to about 7 is to be separated from a sample, the first aqueous dispersion is preferably formed at a pH of about 6 to about 8, followed by the intense mixing, centrifugation, and separation steps, as described above. The second aqueous dispersion (comprising the anion exchange resin to which are bound proteins with pI's less than about the pH of the first aqueous dispersion (i.e. 7)) may then be formed at a pH of about 2 to about 4, followed by the intense mixing, centrifugation, and separation steps. The resulting second supernatant comprises proteins with pI's greater than about the pH of the second aqueous dispersion (i.e. 4), while proteins with pI's less than about 4 are negatively charged and bound to the anion exchange resin. This process may be repeated, by further decreasing the pH at which the aqueous dispersion is formed, to further fractionate the sample.

If the proteins are to be further analyzed or processed, it may also be desirable to release bound proteins from anion exchange resin under non-denaturing conditions so that the released proteins retain their functionality. Accordingly, it is preferable that the second aqueous dispersion is formed at a pH at which (i) at least a fraction of the proteins bound to the anion exchange resin is released from the anion exchange resin, and (ii) the proteins are not denatured. Therefore, in certain embodiments, the second aqueous dispersion is formed at a pH that is less than the pH of the first aqueous dispersion, as low as about 1. For example, to isolate a fraction of proteins with a pI in the range of about 4 to about 7, the second aqueous dispersion is formed at a pH of about 2 to about 4. The resulting second supernatant comprises positively charged proteins (i.e., proteins with pI's greater than the pH of the second aqueous dispersion), while negatively charged proteins (i.e., proteins with pI's less than the pH of the second aqueous dispersion) are bound to the anion exchange resin.

When no further separation is required, the resin may optionally be cleaned for future use by separating the resin from any accumulated precipitate and releasing bound proteins from the resin. The resin is generally cleaned after the last fractionation, namely after the last supernatant is recovered. For example, if the resin is cleaned after one fractionation, a second aqueous dispersion is formed comprising the anion exchange resin at a pH at which (i) all proteins are released from the anion exchange resin, and (ii) any precipitated proteins dissolve into the second aqueous dispersion. The second aqueous dispersion may then be intensely mixed, centrifuged, and the resulting supernatant separated from the anion exchange resin, as previously described. This resulting supernatant comprises the proteins that remained after the first fractionation, namely after the first supernatant was recovered, and the anion exchange resin is free of bound proteins and ready for future use. When cleaning the resin, the pH of the second aqueous dispersion is not greater than about 1.0, and preferably is about 1.0. The pH may be adjusted by a variety of agents known in the art, including acids such as 0.1 M HCl. If desired, this procedure may be performed after any fractionation, i.e., the very same steps as described above with regards to the second aqueous dispersion may be carried out with respect to a third aqueous dispersion.

Separation Using a Cation Exchange Resin

In some embodiments, the separation may be performed using a particulate cation exchange resin or other cation exchange material. A particulate cation exchange resin may be preferred for use in a variety of separations, including (i) separating a fraction of proteins with a pI that is less than the pI of a different fraction of proteins from the sample; (ii) separating a fraction of proteins with a pI that is greater than the pI of a different fraction of proteins from the sample; and/or (iii) separating a fraction of proteins with a pI that is greater than the pI of a fraction of proteins and less than the pI of a different fraction of proteins from the sample. Separation (i) is especially efficient when a cation exchange resin is used.

In one embodiment, therefore, the present invention is directed to a process for separating a protein from an aqueous sample containing a mixture of proteins using a cation exchange material. The process comprises combining the aqueous sample with the cation exchange material to form an aqueous combination; preferably the ion exchange material is a particulate cation exchange resin and the aqueous combination is an aqueous dispersion of the particulate resin in the sample. The aqueous dispersion is preferably formed at a pH which is less than the pI of a fraction of the proteins in the aqueous dispersion but greater than the pI of a different fraction of the proteins in the dispersion. Preferably the cation exchange resin is capable of free-flowing movement relative to the rest of the dispersion, as discussed below, and may advantageously first be equilibrated to the pH of the aqueous dispersion prior to performing the separation.

The pH at which the first aqueous dispersion is formed may vary depending on the desired separation. For instance, if a fraction of proteins with a pI less than the pI of a different fraction of proteins in the sample is to be separated from the sample, it may be advantageous to form the first aqueous dispersion at a pH at which the proteins to be separated from the sample have a negative charge and thus do not bind to the cation exchange resin, as discussed below. For example, in one embodiment, proteins with pI's less than about 4.0 may be separated from the sample. For this separation, the first aqueous dispersion may advantageously be formed at a pH of about 4.0 to about 5.0. Under these conditions, proteins with pI's less than about 4.0 are negatively charged and do not bind to the cation exchange resin, while proteins with pI's greater than about the first pH (e.g. 4.0) are positively charged and do bind to the cation exchange resin. Proteins with pI's of about the first pH (e.g. 4.0) would have a zero net charge. In some instances, such proteins may precipitate from solution. In other instances, i.e., in the case of highly soluble proteins, such proteins may be found in solution.

In yet another alternative, it may be desirable to separate a fraction of proteins with a pI greater than the pI of one fraction of proteins in the sample and less than the pI of a different fraction of proteins in the sample from the sample. In this instance, the pH at which the first aqueous dispersion is formed is preferably such that proteins with pI's less than the pI of the protein fraction to be separated are negatively charged and thus do not bind to the cation exchange resin. For example, if a fraction of proteins with a pI in the range of about 4 to about 7 is to be separated from a sample, the first aqueous dispersion may advantageously be formed at a pH of about 4 to about 5. (See Example 3 and FIGS. 10B and 10C)

An aqueous dispersion comprising a cation exchange resin is intensely mixed and centrifuged, as previously described above with regards to an aqueous dispersion comprising an anion exchange resin (the same speed, force, and time ranges are applicable). For example, a first aqueous dispersion may be intensely mixed and centrifuged, as described above. Intense mixing causes the fraction of proteins having a pI greater than the pH at which the first aqueous dispersion is formed to bind to the cation exchange resin. After the first aqueous dispersion is intensely mixed, the intensely mixed first aqueous dispersion may also be centrifuged to cause the aqueous dispersion to stratify into a first concentrated solids fraction and a first supernatant, the first supernatant comprising the fraction of the proteins which did not bind to the resin (i.e., the negatively charged proteins with pI's less than the pH of the first aqueous dispersion) and the first concentrated solids fraction comprising protein-bound cation exchange resin (with positively charged proteins having pI's greater than the pH of the first aqueous dispersion bound to the resin) and any precipitate. The first supernatant may then be separated from the first concentrated solids fraction by any suitable means, just as described above with regards to separating a supernatant from a concentrated solids fraction comprising an anion exchange resin.

If desired, several separations may be performed to recover a particular protein fraction with a particular pI from the sample. Generally, when more than one separation is performed, a second aqueous dispersion comprising the cation exchange resin (to which are bound proteins with pI's greater than the pH of the first aqueous dispersion) is formed at a pH at which at least a fraction of the proteins bound to the cation exchange resin is released from the resin. This step is followed by intense mixing of the second aqueous dispersion, as described above; centrifuging of the intensely mixed second aqueous dispersion, as described above, to cause the second aqueous dispersion to stratify into a second concentrated solids fraction and a second supernatant, the second supernatant comprising the fraction of the proteins that was released from the resin; and separating the second supernatant from the second concentrated solids fraction.

The pH at which the second aqueous dispersion is formed may vary depending on the desired separation. Preferably, the second aqueous dispersion is formed at a pH that is greater than the pH at which the first aqueous dispersion was formed. As the pH is increased, proteins bound to the cation exchange resin may be released from the resin. It is generally advantageous to form the second aqueous dispersion at a pH only as high as necessary to release only proteins with pI's below a selected target pI from the resin (i.e., negatively charged proteins), while proteins with pI's above the target pI remain bound to the cation exchange resin. For example, if a fraction of proteins with a pI in the range of about 4 to about 7 is to be separated from a sample, the first aqueous dispersion is preferably formed at a pH of about 3 to about 5, followed by the intense mixing, centrifugation, and separation steps, as described above. The second aqueous dispersion (comprising the cation exchange resin to which are bound proteins with pI's greater than about the first pH (e.g. 4)) may then be formed at a pH of about 7 to about 8, followed by the intense mixing, centrifugation, and separation steps. The resulting second supernatant will comprise proteins with pI's less than about the second pH (e.g. 7), while proteins with pI's greater than about the second pH (e.g. 7.0) are positively charged and bound to the cation exchange resin. This process may be repeated, by further raising the pH at which the aqueous dispersion is formed, to further fractionate the sample. This example is further described in Example 3 and illustrated in FIGS. 10B and 10C.

If the proteins are to be further analyzed or processed, it may also be desirable to release bound proteins from cation exchange resin under non-denaturing conditions so that the released proteins retain their functionality. Accordingly, it is preferable that the second aqueous dispersion is formed at a pH at which (i) at least a fraction of the proteins bound to the cation exchange resin is released from the cation exchange resin, and (ii) the proteins are not denatured. Therefore, in certain embodiments, the second aqueous dispersion is formed at a pH that is greater than the pH of the first aqueous dispersion, as high as about 12. For example, to isolate a fraction of proteins with a pI in the range of about 4.0 to about 7.0, the second aqueous dispersion is formed at a pH of about 7 to about 8 (the first aqueous dispersion having been preferably formed at a pH of about 3 to about 5). The resulting second supernatant comprises negatively charged proteins (i.e., proteins with pI's less than the pH of the second aqueous dispersion), while positively charged proteins (i.e., proteins with pI's greater than the pH of the second aqueous dispersion) are bound to the cation exchange resin.

When no further separation is required, the resin may optionally be cleaned for future use by separating the resin from any accumulated precipitate and releasing bound proteins from the resin. The resin is generally cleaned after the last fractionation, namely after the last supernatant is recovered. For example, if the resin is cleaned after one fractionation, a second aqueous dispersion is formed comprising the cation exchange resin at a pH at which (i) all proteins are released from the cation exchange resin, and (ii) any precipitated proteins dissolve into the second aqueous dispersion. The second aqueous dispersion may then be intensely mixed, centrifuged, and the resulting supernatant separated from the cation exchange resin, as previously described. This resulting supernatant comprises the proteins that remained after the first fractionation, namely after the first supernatant was recovered, and the cation exchange resin is free of bound proteins and ready for future use. In one embodiment, the pH of the second aqueous dispersion is about 14.0. The pH may be adjusted by a variety of agents known in the art, including bases such as 0.1 M NaOH and 0.1 M KOH. If desired, this procedure may be performed after any fractionation, i.e., the very same steps as described above with regards to the second aqueous dispersion may be carried out with respect to a third aqueous dispersion.

Ion Exchange Materials

Charged molecules found in samples, such as proteins, peptides, amino acids, and other solutes, may be separated from samples by means of ion exchange, e.g., ion exchange resins. Ion exchange resins typically comprise two kinds of ions: an ion bound to the resin and an oppositely charged counterion bound to this ion. When a resin is contacted with a sample, charged molecules in the sample displace the counterions and bind to the ions which are bound to the resin. During a separation process, such bound charged molecules may be competitively and sequentially displaced or eluted from the resin in an order that is inversely related to the binding affinity of the charged molecules by raising the concentration of counterions in the sample. For a more detailed discussion of ion exchange, see "Chromatography of Amino Acids on Sulfonated Polystyrene Resins," Moore, et al., *Analytical Chemistry*, 30:1185-1190 (1958).

In general, there are four major types of ion exchange resins or media. Strong cation exchange resins/media are strongly acidic and generally contain fully ionized acidic groups, such as sulfonic acid groups, or their corresponding salts. These exchangers are negatively charged and bind cations very strongly. In contrast, strong anion exchange resins/media are strongly basic and generally contain highly ionized basic groups, such as quaternary ammonium groups. Strong anion exchange materials are positively charged and bind anions very strongly. Strong anion exchange resins are typically further classified into two types, type I resins, which contain trialkyl ammonium chloride or hydroxide (e.g., Dowex-1 (trimethylbenzyl ammonium)), and type 11 resins, which contain dialkyl 2-hydroxyethyl ammonium chloride or hydrochloride (e.g., Dowex-2 (dimethyl-2-hydroxyethylbenzyl ammonium). The exchange capacity of strong acid or base resins is typically independent of the pH of the sample contacting the resin.

Weak cation exchange resins/media contain weak acids, such as carboxylic acid groups, or their corresponding salts; weak cation exchange media include carboxymethyl (CM) cellulose resin and Chelex-100 resin. Since the degree of dissociation of a weak acid resin is influenced by pH, resin capacity depends in part on solution pH. For example, a typical weak acid resin has very limited capacity below a pH of 6.0. Thus, "weak cation exchange resin" refers to a resin, comprising a weak acid exchanger, which will be negatively charged when the pH of the solution contacting it is above the $pK_a$ of the exchanger. In contrast, weak anion exchange resins/media contain weak bases, such as ammonium chloride or hydroxide; weak anion exchange media include diethylaminoethyl (DEAE) resin and Dowex® (polyamine) resin. Since the degree of ionization of a weak base resin is influenced by pH, resin capacity depends in part on solution pH. For example, weak base resins typically exhibit minimum exchange capacity above a pH of 7.0. Thus, "weak anion exchange resin" refers to a resin, comprising a weak base exchanger, which will be positively charged when the pH of the solution contacting it is below the $pK_a$ of the exchanger.

Ion exchange resins may comprise a variety of charged groups. For example, an anion exchange resin may comprise charged groups such as diethylaminoethyl (DEAE), quaternary aminoethyl (QAE), quaternary ammonium (O), and/or other primary, secondary, tertiary ($pK_a$ 9.8), or quaternary amines. A cation exchange resin may comprise charged groups such as carboxymethyl (CM), sulfopropyl (SP), and/or methyl sulfonate (S). These charged groups may be attached to a variety of core materials including those that are agarose-based (e.g., SEPHAROSE CL-6B, SEPHAROSE FAST FLOW, and SEPHAROSE HIGH PERFORMANCE), cellulose-based (e.g., DEAE SEPHACEL), dextran-based (e.g., SEPHADEX), silica-based, and synthetic polymer based.

Although any of a variety of ion exchange materials may be used in accordance with the methods described herein to bind soluble, charged proteins, peptides, amino acids, and/or other charged molecules, the ion exchange materials are preferably weak anion exchange materials or weak cation exchange materials. In one embodiment, the ion exchange material used herein comprises an anion exchange resin. Preferably, the anion exchange resin used herein comprises polybuffer exchanger 94 (PBE 94) resin (GE Healthcare Co.). PBE 94 is a weak anion exchange resin comprising mixed quaternary and tertiary amines. In another embodiment, the ion exchange material used herein comprises a cation exchange resin. The cation exchange resin used herein preferably comprises carboxymethyl ($pK_a$ 4.5) with a sepharose core material.

Because the aqueous dispersions described herein (e.g., aqueous dispersions comprising a sample, which contains various proteins, ion exchange resin, and, optionally, a buffer or other pH adjusting agent) may be mixed, preferably intensely mixed, to better facilitate the separation of proteins, in certain embodiments, the resin used herein is capable of free-flowing movement relative to the rest of the dispersion. Specifically, in such embodiments, the resin particles are preferably capable of independent movement relative both to other resin particles and to other dispersion components. Aqueous dispersions comprising free-flowing resin may therefore be amenable to mixing, especially intense mixing, in contrast to the relatively immobile state of resin that is packed in a column.

Although primarily discussed herein in terms of free-flowing resin, it is to be understood that the ion exchange material used in the methods of the present invention may be in various formats. For example, the ion exchange material may be in the form of beads coated with exchangers, in the form of a membrane ion exchange resin, in the form of exchangers coated on the interior surface or a portion of the interior surface of a container in which the separation is being performed, and/or generally in the form of an object coated with exchangers, i.e.,

a magnetic stir bar or rod (which can then be placed in the container where the separation is being performed). Other suitable formats for the ion exchange materials will be apparent to those skilled in the art.

Buffers

Any agent or buffer capable of adjusting the sample or aqueous dispersion to the desired pH may be used in the methods described herein. A buffer is a solution that is resistant to changes in pH, such as those changes that result from the addition of an acid or a base to the buffer solution. Because a buffer guards against the effects of an added acid or an added base, it generally contains a component that neutralizes an acid as well as a component that neutralizes a base. Thus, a buffer typically comprises a weak acid and its conjugate base or a weak base and its conjugate acid. In the case of a weak acid, the weak acid can neutralize added base and its conjugate base can neutralize added acid. A buffer cannot comprise a strong acid or a strong base alone, as a strong acid alone or a strong base alone does not have the capacity to resist changes in pH, as discussed below.

A buffer generally comprises at least one buffer component, i.e., a weak base, a weak acid, or combinations thereof. A weak acid or a weak base can be described by a dissociation constant ($K_d$), which is a measure of the extent to which a dissociation reaction, $AB \leftrightarrow A+B$, proceeds at equilibrium. In the case of a strong acid or a strong base, the above reaction would typically be written with a regular forward arrow, because the equilibrium lies very far to the right, i.e. favoring the products (the dissociated ions). Because this equilibrium lies so far to the right, strong acids and bases do not have the capacity to resist changes in pH. A dissociation constant is expressed by the following equation, where [A], [B], and [AB] indicate the concentrations of A, B, and AB, respectively:

$$K_d = [A][B]/[AB].$$

A strong acid or a strong base generally cannot be described by a dissociation constant, because the equilibrium lies so far to the right, as described above, and the products of the reaction are so favored (the denominator in the above reaction would approach zero). For a weak acid, this dissociation constant is generally referred to as the acid dissociation constant ($K_a$) and is a measure of how likely an acid is to release a proton in the dissociation reaction $HA = H^+ + A^-$, proceeding at equilibrium. An acid dissociation constant is expressed by the following equation:

$$K_a = [H^+][A^-]/[HA].$$

The $pK_a$ of a weak acid (or a protonated base) is expressed by the following equation:

$$pK_a = -\log(K_a).$$

The $pK_a$(s) of a buffer's component(s) is closely related to the buffer's buffering range. Generally, a buffer can be described by both its buffer capacity, including acid buffer capacity and base buffer capacity, and its buffer range. Acid buffer capacity is defined as the number of moles of strong acid per liter of buffer that is required to decrease the pH of the buffer by 1 unit. Base buffer capacity is defined as the number of moles of strong base per liter of buffer that is required to increase the pH of the buffer by 1 unit. Buffer range is the pH range over which a buffer neutralizes added acids or bases and maintains a fairly constant pH (+/−1 pH unit). A buffer's range typically spans one pH unit above or below the $pK_a$ of a buffer component. For example, alloxanic acid has a $pK_a$ of about 6.64 and a buffer range of about pH 5.64 to about pH 7.64. One skilled in the art would thus select a buffer comprising a component with a $pK_a$ that is close to a desired pH, as discussed below. For buffers comprising more than one component, the buffer range would be computed in the same way with respect to each component's $pK_a$. For example, a buffer comprising acetic acid ($pK_a$ of about 4.7) and ethanolamine ($pK_a$ of about 9.6) would have a split buffer range of about pH 3.7 to about pH 5.7 and about pH 8.6 to about pH 10.6. The gaps in such a split buffer range, i.e., about pH 5.7 to about pH 8.6, indicate pH ranges where the buffer has substantially no buffer capacity.

If, when the $pK_a$'s of buffer components are ordered from lowest to highest, there is not a difference of approximately greater than 2 units between any two consecutive $pK_a$'s, then the buffer range will span from one pH unit below the lowest $pK_a$ to one pH unit above the highest $pK_a$, without any gaps where changes in pH are not resisted. Certain buffer components are polyprotic, meaning they contain more than one proton (hydrogen) per molecule. Polyprotic buffer components release protons in a stepwise manner, releasing a proton at each step, and the total number of steps depends on the total number of protons per molecule. For each step, there is a different dissociation constant, i.e. $pK_{a1}$, $pK_{a2}$, $pK_{a3}$, etc. A buffer comprising a polyprotic weak acid is thus described by more than one $pK_a$ value. When calculating the buffer range of a buffer comprising a polyprotic acid, the procedure described above is followed and all of the $pK_a$'s are ordered from lowest to highest. Again, if there is not a difference of approximately greater than 2 units between any two consecutive $pK_a$'s, then the buffer range will span from one pH unit below the lowest $pK_a$ to one pH unit above the highest $pK_a$, without any gaps where changes in pH are not resisted. If there is a difference of approximately greater than 2 units between any two consecutive $pK_a$'s, then the buffer will have a split buffer range, as described above. For example, for a buffer comprising several polyprotic acids, such as a buffer comprising bis-tris propane ($pK_{a1}$ of about 9; $pK_{a2}$ of about 6.8) and piperazine ($pK_{a1}$ of about 9.8; $pK_{a2}$ of about 5.6), the buffer range is about pH 4.6 to about pH 10.8.

In addition to having the ability to resist pH changes in a buffer range that typically spans one pH unit above or below the $pK_a$ of a buffer component, buffers themselves are also characterized by a pH. This pH varies with the concentrations of weak acid and conjugate base or weak base and conjugate acid. The pH of a buffer is generally described by the Henderson-Hasselbalch equation:

$$pH = pK_a + \log([A^-]/[HA]).$$

Derivatives of this basic equation exist which allow one to calculate the pH of a buffer comprising multiple components. Thus, buffers are not only capable of resisting pH changes within a certain pH range, they are also capable of adjusting a particular solution, including a biological sample or an aqueous dispersion, to a desired pH. And, by further using a buffer to modify the pH of such a buffered solution, as opposed to using a strong acid alone or a strong base alone, one is able to make very slight modifications to the pH and change the pH in a very controlled fashion. This is true because the buffer that is added to the buffered solution changes the concentrations of both the weak acid and its conjugate base or both the weak base and its conjugate acid. In contrast, if, for example, a strong base, such as sodium hydroxide (NaOH), is added to adjust (increase) the pH of a buffered solution comprising a weak acid, the added hydroxide ions ($OH^-$) consume the protons ($H^+$) in solution, causing HA to dissociate in order to replenish the supply of $H^+$ and maintain $K_a$. Eventually, the concentration of HA is depleted to such an extent that the loss of $H^+$ can no longer be counteracted and the pH begins to increase more rapidly, i.e. the solution loses its capacity to buffer. As described above, if a buffer was used to increase the pH of the buffered solution, rather than a strong base, the buffer would replenish the supply of HA to some extent, thereby avoiding a rapid increase in pH.

Because of all the above-described characteristics of a buffer, a buffer is a preferred agent for adjusting an aqueous dispersion to a desired pH. Preferably, a buffer is selected wherein the target pH(s) of the aqueous dispersion falls within the buffer range of the buffer. For example, if the desired pH of a sample is 3.3, a buffer with a buffer range that includes 3.3 is preferably selected. Preferably, the pH of 3.3 is not at the lower or higher end of this range, so that the pH can be modified in further separation steps without the loss of buffer capacity. For example, a buffer component with a $pK_a$ of 3.3 may be selected, in order to give a buffer range of about pH 2.3 to about pH 4.3. It is generally more preferable to select a buffer characterized by a broader buffer range, such as about pH 2 to about pH 9, is selected.

Using the principles described herein, one skilled in the art may readily choose a buffer appropriate for the desired separation. A buffer may comprise one or more buffer components. If the buffer comprises multiple buffer components (or a single buffer component with multiple $pK_a$'s, i.e., a polyprotic acid), it is generally preferable that the buffer does not have a split buffer range, as described above.

In general, an agent with a $pK_a$ may be used as a buffer component, i.e., a weak acid or a weak base. Examples of suitable buffer components, which may be used alone or combined with other buffer components, include, but are not limited to, bis-tris propane, with a $pK_{a1}$ equal to about 9.00 and a $pK_{a2}$ equal to about 6.80; piperazine, with a $pK_{a1}$ equal to about 9.80 and a $pK_{a2}$ equal to about 5.60; alloxanic acid, with a $pK_a$ equal to about 6.64; 1,2-propanediamine, with a $pK_{a1}$ equal to about 9.80 and a $pK_{a2}$ equal to about 6.60; histamine, with a $pK_{a1}$ equal to about 9.80 and a $pK_{a2}$ equal to about 6.00; benzimidazole, with a $pK_a$ equal to about 5.50; isoquinoline, with a $pK_a$ equal to about 5.40; 7-isoquinolinol, with a $pK_{a1}$ equal to about 8.90 and a $pK_{a2}$ equal to about 5.70; 2-methylquinoline, with a $pK_a$ equal to about 5.80; 4-methylquinoline, with a $pK_a$ equal to about 5.70; acridine, with a $pK_a$ equal to about 5.60; ethanolamine, with a $pK_a$ equal to about 9.60; trimethylamine, with a $pK_a$ equal to about 9.80; N,N-dimethylglycine, with a $pK_a$ equal to about 9.90; noradrenaline, with a $pK_{a1}$ equal to about 9.70 and a $pK_{a2}$ equal to about 8.60; pyridine, with a $pK_a$ equal to about 5.20; acetic acid, with a $pK_a$ equal to about 4.70; lactic acid, with a $pK_a$ equal to about 3.80; chloroacetic acid, with a $pK_a$ equal to about 2.80; glycocyamine, with a $pK_a$ equal to about 2.80; chloroaniline, with a $pK_a$ equal to about 2.80; dinicotinic acid, with a $pK_a$ equal to about 2.80; 4-aminoazobenzene, with a $pK_a$ equal to about 2.82; formic acid, with a $pK_a$ equal to about 3.75; 3-chloropropanoic acid, with a $pK_a$ equal to about 3.98; acetoacetic acid, with a $pK_a$ equal to about 3.60; N-acetylglycine, with a $pK_a$ equal to about 3.70; uric acid, with a $pK_a$ equal to about 3.90; 6-chloropteridine, with a $pK_a$ equal to about 3.70; thiazolamine, with a $pK_a$ equal to about 5.30; melamine, with a $pK_a$ equal to about 5.00; benzimidazole, with a $pK_a$ equal to about 5.40; N,N-dimethylaniline, with a $pK_a$ equal to about 5.20; N-ethylaniline, with a $pK_a$ equal to about 5.10; 5-methylquinoline, with a $pK_a$ equal to about 5.20; itaconic acid, with a $pK_{a1}$ equal to about 5.45 and a $pK_{a2}$ equal to about 3.85; m-phthalic acid, with a $pK_{a1}$ equal to about 4.60 and a $pK_{a2}$ equal to about 3.60; malonic acid, with a $pK_{a1}$ equal to about 5.70 and a $pK_{a2}$ equal to about 2.80; adipic acid, with a $pK_{a1}$ equal to about 5.40 and a $pK_{a2}$ equal to about 4.40; and heptanedioic acid, with a $pK_{a1}$ equal to about 5.60 and a $pK_{a2}$ equal to about 4.70. Other examples of suitable buffer components are known in the art and are described in, for example, "Chromatofocusing Using Micropellicular Column Packings with Computer-Aided Design of the Elution Buffer Composition," Kang X. Z. and Frey D. D., *Analytical Chemistry* 74 (5): 1038-1045 (2002).

In addition to using a single buffer, a buffer system comprising two or more buffers may also be used. In one embodiment, the buffer used herein is a buffer system comprising a combination of a first buffer and a second buffer. Preferably, the first buffer is slightly basic, with a pH in the range of about 7.0 to about 9.0, more preferably 8.0, and has a buffer range of about pH 4.6 to about pH 10.8. The second buffer is preferably acidic, with a pH in the range of about 2.3 to about 4.3, more preferably 3.3, and has a buffer range of about pH 1.8 to about pH 6.2. Buffer systems comprising more than two component buffers may also be employed.

One example of a suitable buffer system contains a first buffer comprising bis-tris propane and piperazine and a second buffer comprising pyridine, acetic acid, lactic acid, and chloroacetic acid. As will be apparent to one skilled in the art, the pH of such a buffer system may be varied by altering the ratios of the first and second buffer in the buffer system. One example of altering the percentage of component buffers in a buffer system to change the pH of the buffer system is shown in Table 2. In Table 2, a first buffer, buffer A, comprises bis-tris propane and piperazine and a second buffer, buffer B, comprises pyridine, acetic acid, lactic acid, and chloroacetic acid.

One skilled in the art can readily design other appropriate buffer systems, using the information provided herein.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Fractionation of Plasma Protein Sample

In this example albumin was fractionated by column chromatography and prefractionation using PBE 94. The efficiency of these methods was measured by one-dimensional electrophoresis, two-dimensional electrophoresis, and western blot.

Chromatofocusing of Human Plasma Protein Samples

In this example, chromatofocusing was performed on a plasma protein sample containing 15 human plasma proteins. The plasma proteins contained in the sample are listed in Table 1. 66% of the sample total mass constituted albumin.

The system used for this analysis is an Äkta purifier (Amersham Pharmacia Corporation, Uppsala, Sweden). Chromatofocusing is an ion-exchange chromatography technique in which the proteins are bound to an anion exchanger, Polybuffer Exchanger 94 (PBE 94), then eluted by a continuous decrease of the buffer pH so that proteins elute in order of their isoelectric points. PBE 94 is a weak anion exchange resin. The matrix is polystyrene/divinyl benzene. The ion exchanger type is mixed quaternary and tertiary amines. The working range of this resin is pH 4 to 9. PBE 94 was packed in a 250 mm×5 mm column according to the manufacturer's instructions.

The column was first equilibrated with buffer A (12.5 mM bis-tris propane and 12.5 mM piperazine, pH 7.8) at a flow rate of 1 mL/min until the solution eluted had a stable pH of 7.8. A volume of 22.5 µL of the plasma protein sample containing 1.355 mg of proteins was dissolved in 500 µL of buffer A, injected in the column, and the concentration of buffer B (12.5 mM pyridine, 12.5 mM acetic acid, 12.5 mM lactic acid and 12.5 mM chloroacetic acid, pH 3.3) is set from 0 to 100% in 60 minutes, held on 100% for 30 minutes, then a 0.1 M HCl solution was pumped to elute the acidic proteins. The column was quickly reequilibrated with buffer A to avoid any damage secondary to the low pH. Fractions were collected every 2 minutes. A UV detector at 215 nm and a pH meter were used respectively for the detection of eluting proteins and to monitor the pH change of the eluting solution.

Figure 1:
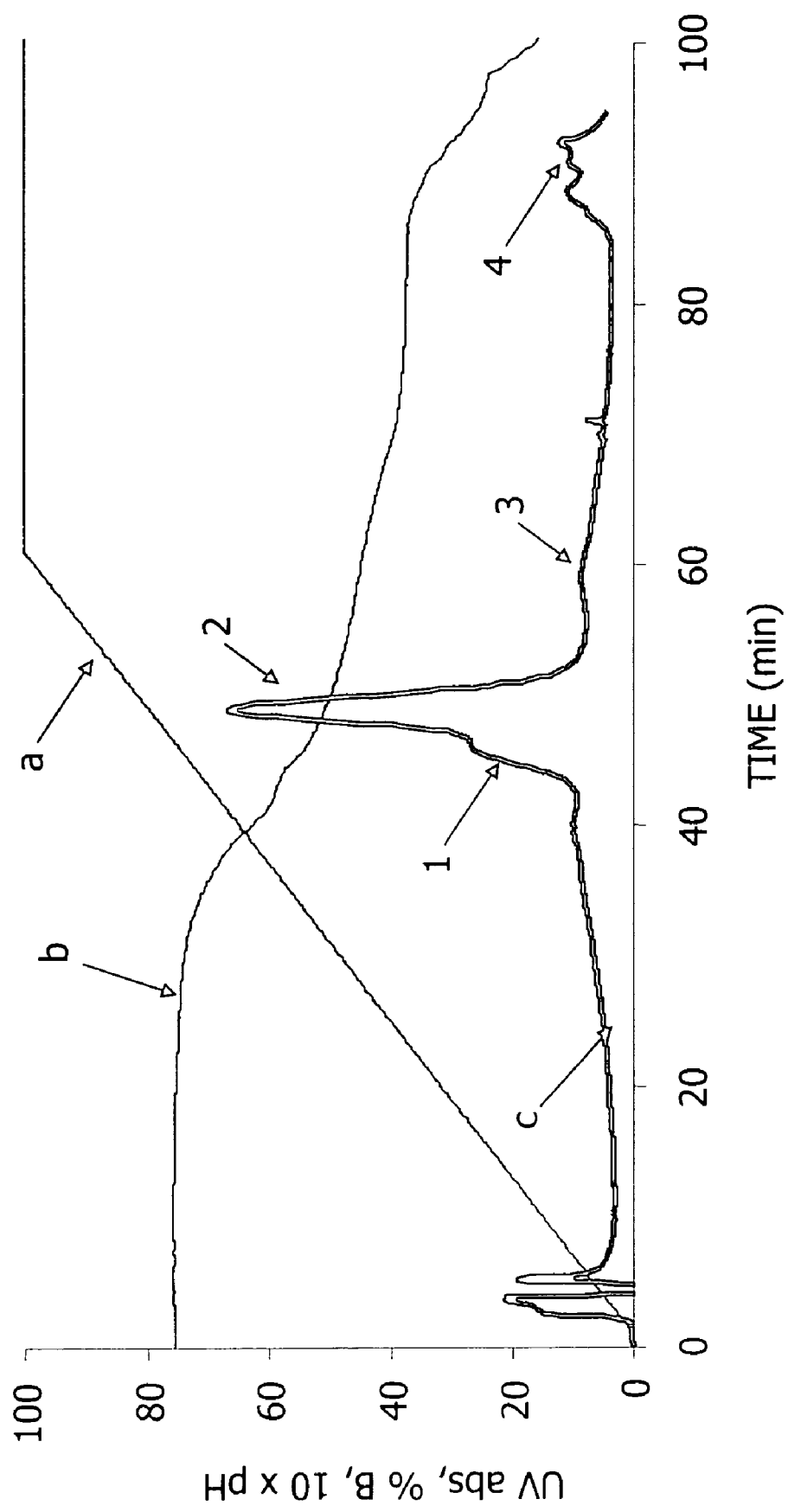
FIG. 1 depicts a chromatogram of the chromatofocusing separation of 1.355 mg contained in 22.5 μL of a human plasma protein sample, as described in Example 1. (a) is the concentration of the elution buffer (i.e., buffer B) set from 0 to 100% in 60 minutes; (b) is the pH gradient generated by the mixing of buffer A (pH=8) and buffer B (pH=3.3); and (c) is 215 nm absorption of the eluting plasma proteins for fractions 1 to 4. Fractions 1 to 4 represent the different fractions that were collected and analyzed by liquid chromatography mass spectrometry and SDS-polyacrylamide gel.

The chromatogram of separation of the human plasma proteins based upon pI generated several peaks (FIG. 1). The peak with the largest area (FIG. 1) is thought to represent albumin, as albumin constitutes 66% of this sample, and this peak is formed at a pH of eluant close to the pI of albumin (pI 5.92).

TABLE 1

Composition of 15 Human Plasma Protein Sample

| Protein | Mass (µg) |
|---|---|
| transthyretin | 0.099 |
| albumin | 179.6 |
| α1-glycoprotein | 3 |
| antitrypsin | 5.45 |
| ceruloplasmin | 1 |
| macroglobulin | 7.4 |
| haptoglobulin | 4 |
| transferrin | 11 |
| complement C3C | 5 |
| complement C4 | 0.7 |
| C-reactive protein | 0.2 |
| IgG | 44 |
| IgA | 8.8 |
| IgM | 3.6 |
| α1-antichymotrypsin | 1.1 |

Nonporous Silica-Reversed-Phase-High Performance Liquid Chromatography-Electrospray Ionization-Time of Flight-Mass Spectrometry (NPS-RP-HPIC-ESI-TOF-MS)

To test the efficiency of the separation of the sample that occurred in Example 5, liquid chromatography electrospray ionization mass spectrometry was carried out for the fractions labeled 1 to 4 in FIG. 1.

A nonporous silica column allows for the rapid separation of a large number of proteins with high recovery compared to porous columns. A System Gold 125 S solvent module (Beckman Coulter Inc., Fullerton, Calif., USA) pump and a 4.6 mm×33 mm nonporous column (Eprogen Inc., Darien, Ill., USA) were used for the RP-HPIC separation. 10 µL of the 2 mL fractions (fractions 1 and 2) were injected, solvent A was water-0.1% trifluoroacetic acid (TFA) and solvent B was acetonitrile-0.1% TFA. The gradient was run from 0 to 40% B in 5 minutes, 40% to 70% in 20 minutes, 70% to 100% in 2 minutes, and was held on 100% for 5 minutes at a flow rate of 200 µL/min. The temperature of the column was held constant at 60° C. to improve the resolution and reduce the pressure. The detector used was a Beckman gold UV detector; proteins were detected at 215 nm. The outlet of the detector was connected to the inlet of a T100LC (Jeol, Dearborn, Mass., USA), electrospray ionization time of flight mass spectrometer. The mass spectrometer parameters were: Source capillary 3000 V, sample cone 20 V, RF lens 100 V, Extraction cone 5 V, Desolvation temperature 250° C., and source temperature 80° C. Deconvolution was carried out using the Jeol ESI Deconvolution V2 program.

Figure 2A:
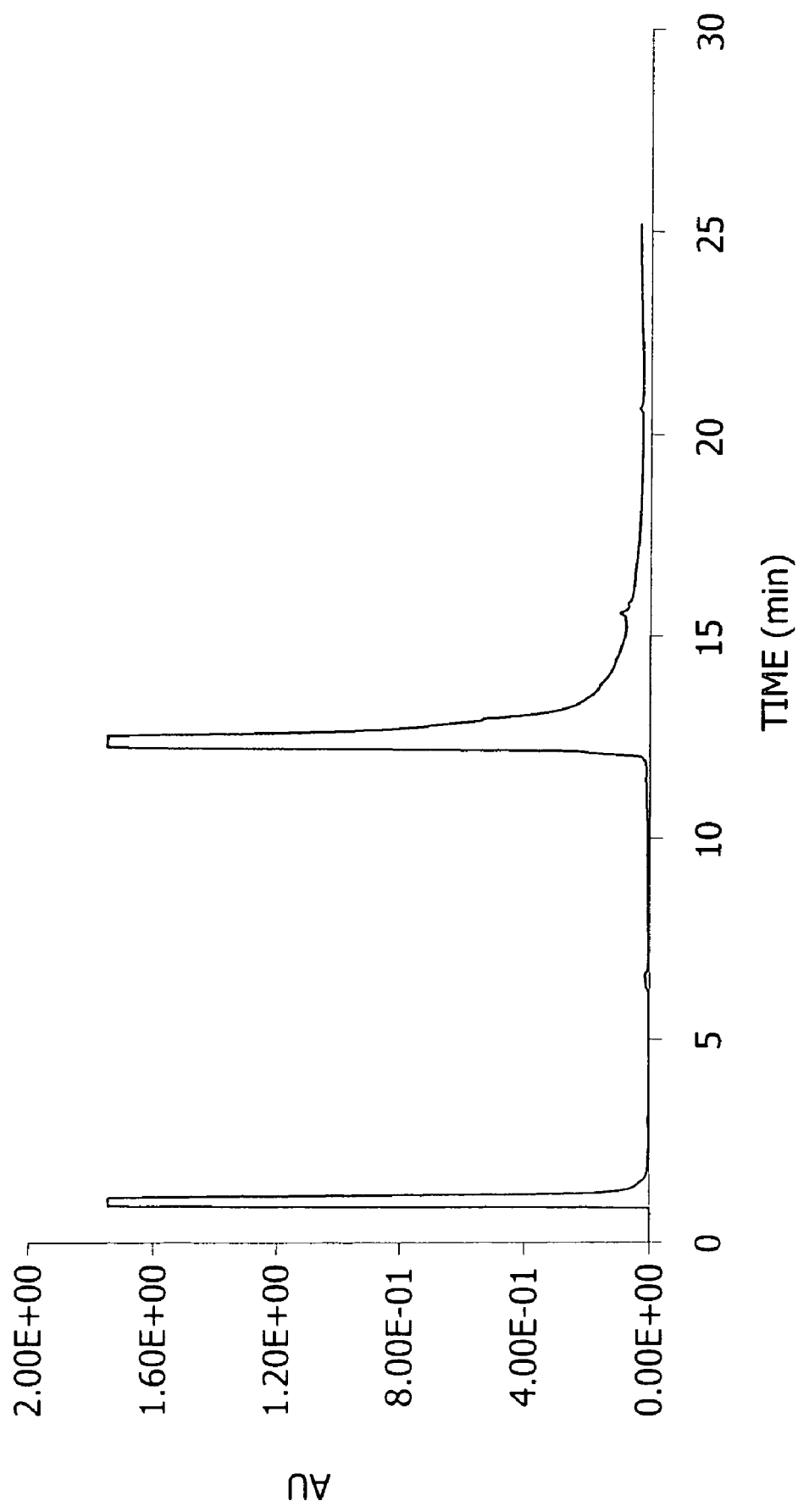
FIG. 2A is the NPS-RP-HPIC chromatogram of fractions 1 and 2 from FIG. 1. 10 μL of each fraction was injected. The first peak (i.e., at approximately 1 minute) is the salt ions, and the second peak (i.e., at approximately 12.5 minutes) is albumin.
Figure 2B:
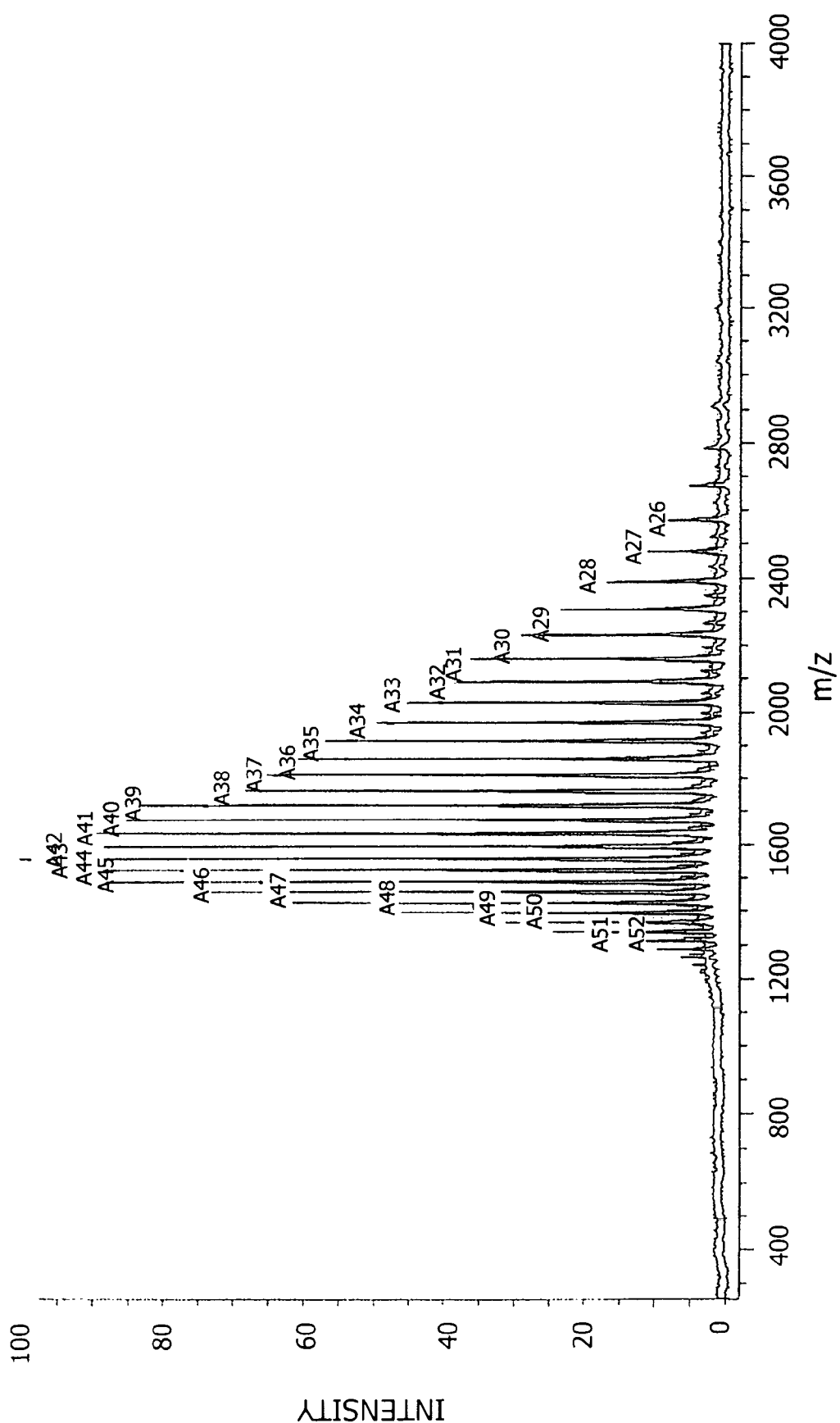
FIG. 2B is the ESI-TOF-MS measured spectrum for the peak shown at 12.5 minutes in the chromatogram of FIG. 2A. The number at the top of each peak represents the ionization state of the 66,804.84 Da albumin.

This separation yielded two peaks (FIG. 2A): a peak at 1 min. representing the salts and ions from the buffers used for the chromatofocusing, and a peak at 12.5 min. The deconvolution of the measured spectrum (FIG. 2B) of this peak showed a molecular mass ranging from 65 to 70 kDa (FIG. 2C), corresponding to the molecular masses of the different glycation states of albumin. This was taken as proof that the peak in question represents albumin. Other low-intensity peaks were present as well. For the liquid chromatography electrospray ionization mass spectrometry of the other fractions, deconvolution was made impossible by the presence of several peaks (data not shown).

Sodium Dodecyl Sulfate-Polyacrylamide Gel Electrophoresis (SDS-PAGE) of The Fractions Collected from the Chromatofocusing separation The 2 mL fractions (fractions 1 to 4) from the chromatofocusing separation of Example 5 were vacuum dried and reconstituted with 150 µL of 50 mM Tris-HCl (pH 6.8), 2% SDS, 0.1% bromophenol blue, and 10% glycerol. 30 µL of this mixture was then applied on a 12% polyacrylamide SDS gel. Gels were electrophoresed at 30 V for 30 minutes, then at 50 mA per gel for 45 minutes.

SDS-PAGE analysis of this fraction reveals several proteins other than albumin (FIG. 3). Therefore, albumin cannot be separated from the other plasma proteins using chromatofocusing.

The results (see FIG. 3) show that each fraction contained several proteins other than albumin, with similar pI values. It can be concluded that albumin cannot be isolated from the other proteins using chromatofocusing, and that the elution of albumin from the column occurred between the 75% and 90% concentrations of buffer B (see FIG. 1). The idea of isolating albumin between these two concentrations emerged, and instead of packing PBE 94 resin in a column, 1 mL of this resin was pipetted into an eppendorf tube, where the isoelectric elimination of albumin was accomplished according to the procedure of Example 1.5.

pH Calibration for the Batch Chromatography

In this example, albumin was gradually resolubilized by decreasing the pH of the buffer used in a stepwise manner. The percent of buffer A (12.5 mM bis-tris propane and 12.5 mM piperazine; pH 8) and buffer B (12.5 mM pyridine, 12.5 mM acetic acid, 12.5 mM lactic acid, and 12.5 mM chloroacetic acid; pH 3.3) useful for isolating albumin was determined.

1 mL of the PBE 94 resin was pipetted into a 1.5 mL centrifuge tube. The resin was then washed twice with buffer A. The tube was vortexed for 30 seconds, centrifuged at 5000×g for 1 minute, and the supernatant was aspirated after each wash. 4.5 µL of 15 human plasma protein sample (as described in Example 1 and Table 1) containing 275 µg of plasma proteins was diluted with buffer A to a volume of 350 µL and added to the resin. The resin was vortexed for 30 seconds, centrifuged at 5000×g for 1 minute, and the supernatant was pipetted out. Then, 350 µL of a series of different buffer compositions with increasing percentages of buffer B were sequentially added to gradually decrease the pH of the solution as described in Table 2. Following each buffer addition, the tube was vortexed for 30 seconds, centrifuged at 5000×g for 1 minute, and the supernatant was removed. Fifteen fractions were collected, vacuum dried, reconstituted with 30 µL of 50 mM Tris-HCl (pH 6.8), 2% SDS, 0.1% bromophenol blue and 10% glycerol, and applied to a 10% polyacrylamide SDS gel. Supernatant collected after addition of each buffer composition was added to the gel twice (see FIGS. 4A-4D). Gels were electrophoresed at 30 V 30 minutes, then at 50 mA per gel for 45 minutes.

Figure 4A:
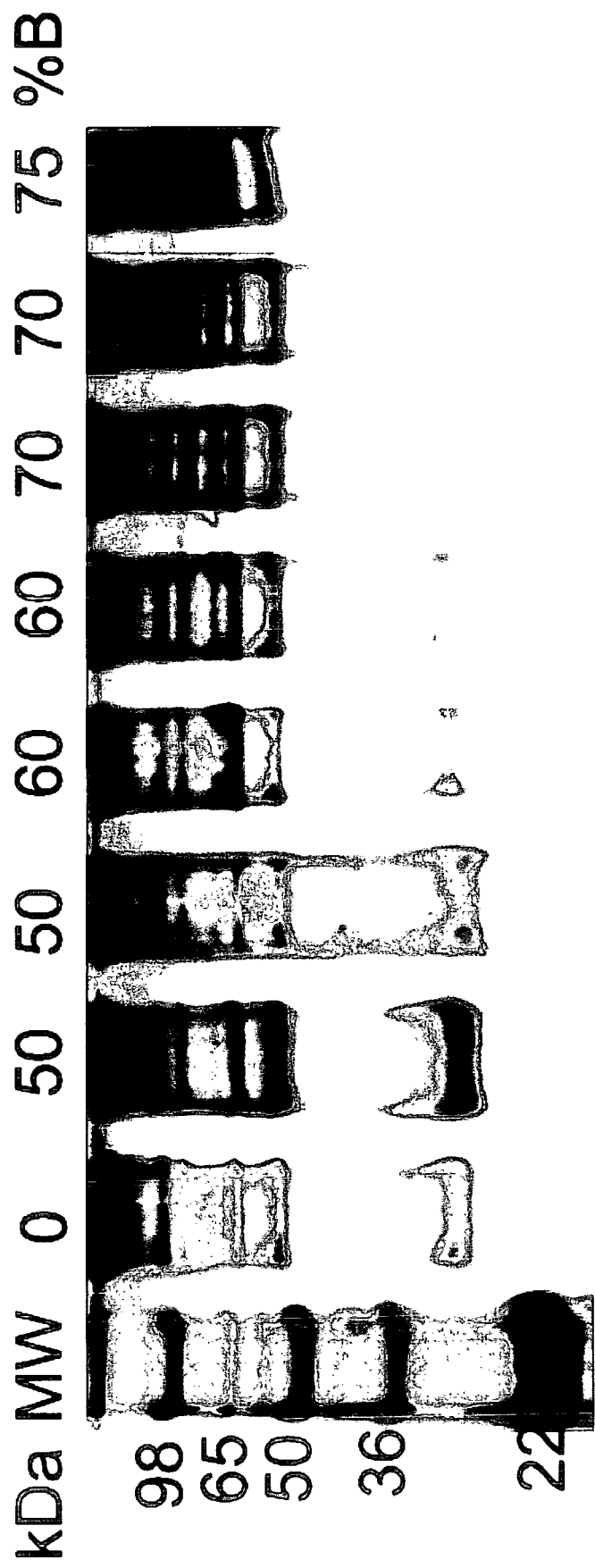
FIGS. 4A and 4B depict a 1-dimensional gel electrophoresis of the supernatant recovered after the addition of buffers consisting of buffer A and buffer B to a plasma protein sample comprising 275 μg of proteins, as described in Example 1. The percent of buffer B (v/v) is marked on the horizontal axis. The molecular weight (kDa) standards are marked on the vertical axis.
Figure 4B:
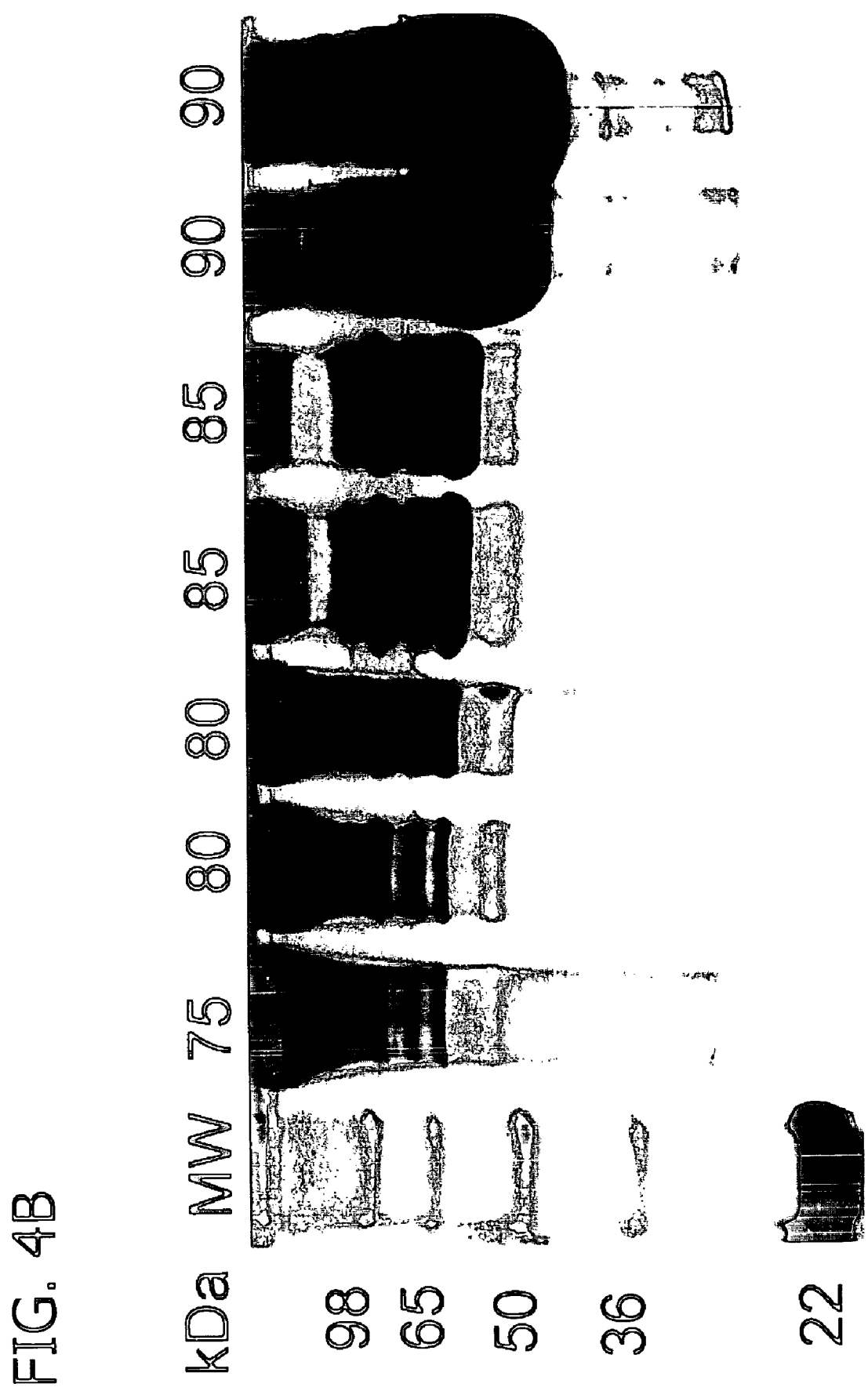
Figure 4C:
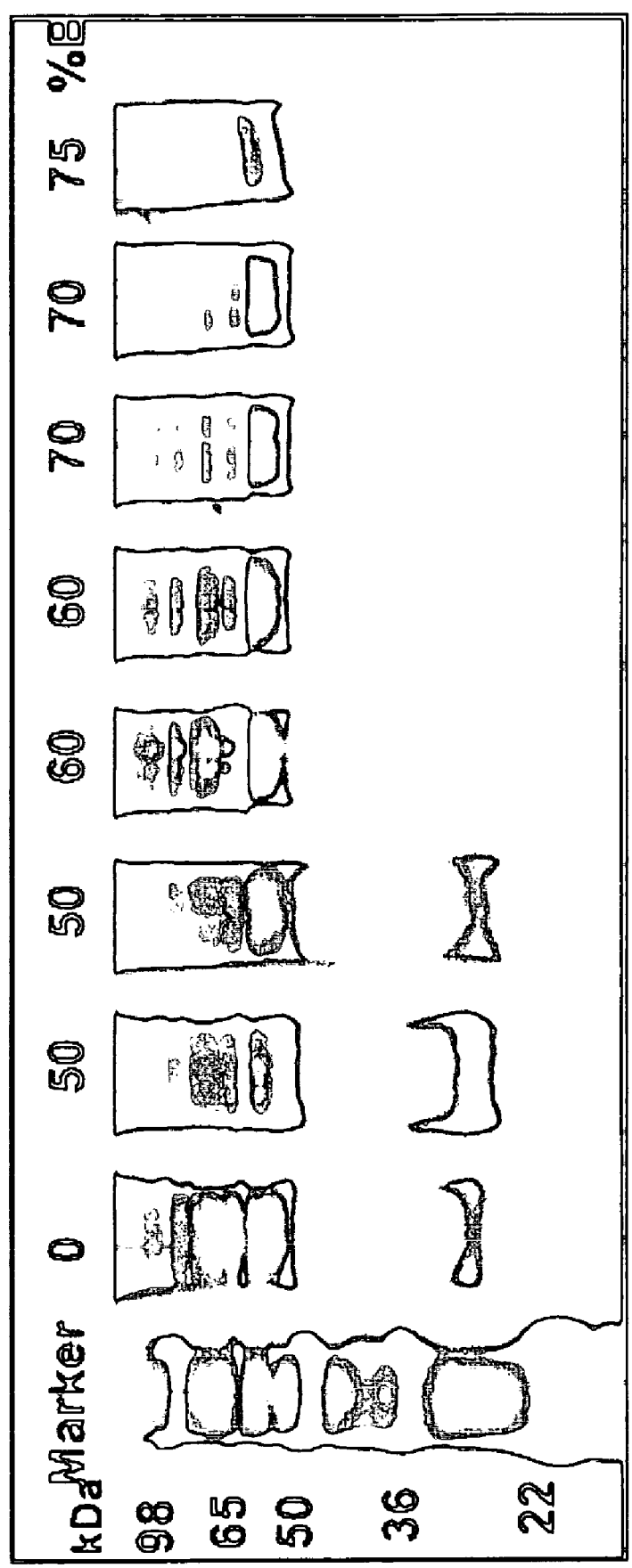
FIG. 4C and FIG. 4D depict the same gels as FIGS. 4A and 4B however.
Figure 4D:
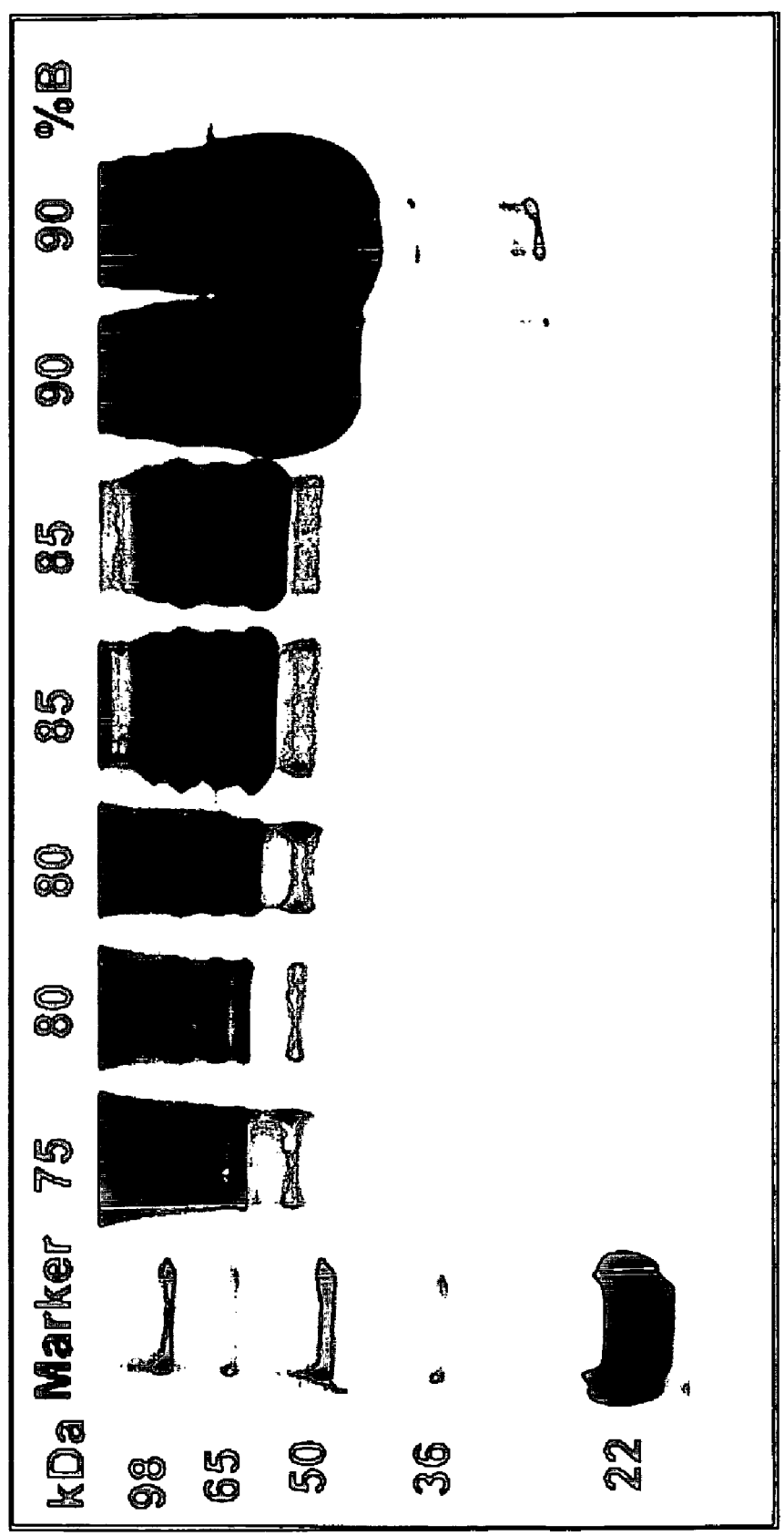

The gels show that for pHs above 5.4, corresponding to a percentage of buffer B lower than 75%, no major 65 kDa bands were shown on a silver-stained gel (FIGS. 4A and 4C). An increasing 65 kDa band appears when the pH is adjusted to values lower than 5, corresponding to a percentage of buffer B higher than 80% (FIGS. 4B and 4D), and this band becomes the dominant feature when the pH is adjusted to a value of 4.7 (90% B). The resolubilization of albumin in the aqueous phase occurred between the 75 and 90% concentrations of buffer B.

TABLE 2

The different compositions of Buffer A and Buffer B added to the resin and the resulting gradually decreasing pH.

| buffer A | % buffer B | pH |
|---|---|---|
| 100 | 0 | 7.8 |
| 50 | 50 | 7 |
| 40 | 60 | 6.8 |
| 30 | 70 | 6.4 |
| 25 | 75 | 5.9 |
| 20 | 80 | 5.6 |
| 15 | 85 | 5.2 |
| 10 | 90 | 4.9 |

Albumin Elimination from Plasma Protein Samples

Additional experiments were done to determine at what percent of buffer B the cut-off should be taken in order to isolate albumin. One mL of the PBE 94 resin was pipetted into a 1.5 mL centrifuge tube. Then, 350 µL of a solution composed of 25% Buffer A and 75% Buffer B was added to the resin, the tube was vortexed for 30 seconds, and this was followed by centrifugation at 5000×g for 1 minute. The supernatant was discarded. This equilibration step was repeated twice. Following equilibration, 275 µg of plasma proteins was added to 350 µL of a solution composed of 25% Buffer A and 75% Buffer B. This mixture was then added to the resin, followed by vortexing for 30 seconds The tube was then centrifuged at 5000×g for 1 minute and the supernatant was recovered. The resin was washed three times with the same buffer (25% Buffer A, 75% Buffer B), with each iteration followed by vortexing for 30 seconds, centrifugation at 5000×g for 1 minute, and supernatant recovery. The supernatant from this phase contained proteins with a pI higher than that of albumin. The resin was then washed with 350 µL of a solution composed of 10% Buffer A and 90% Buffer B, vortexed for 30 seconds, and centrifuged at 5000×g for 1 minute. The supernatant from this phase, containing albumin, was also recovered. This step was repeated three times. Finally, four washes of 350 µL of a 0.1 M HCl solution were performed, and the same procedures were followed to recover the supernatant. The supernatant from this phase contained the acidic proteins. This separation yields 12 fractions.

SDS-PAGE Analysis of the Collected Fractions

For this analysis, the fractions were vacuum dried, reconstituted with 30 µL of 50 mM Tris-HCl (pH 6.8), 2% SDS, 0.1% bromophenol blue, and 10% glycerol, and applied to a 10% polyacrylamide SDS gel. Gels were electrophoresed at 30 V for 30 minutes, then at 50 mA per gel for 45 minutes.

Figure 5A:
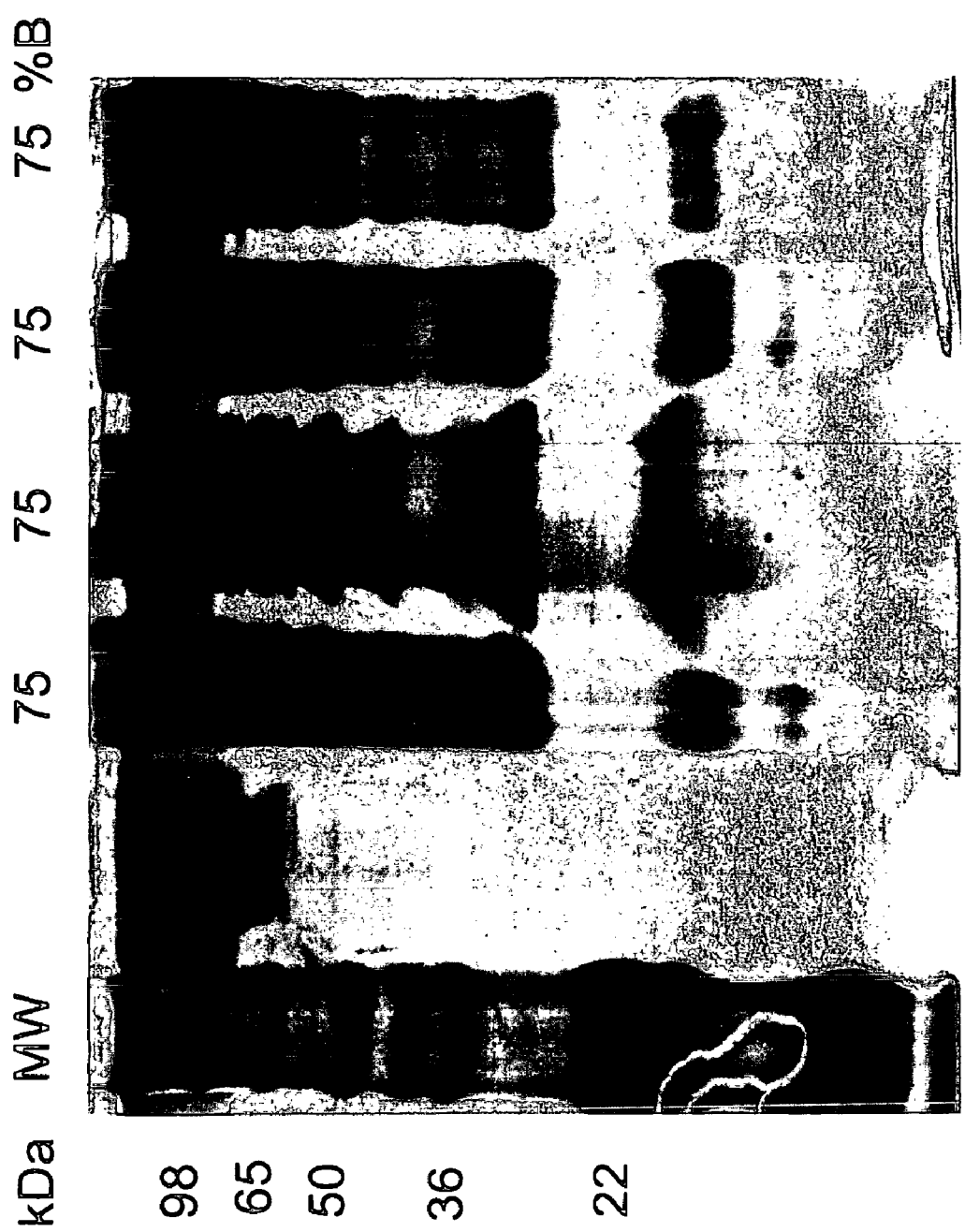
FIGS. 5A and 5B depict a 1 dimensional gel electrophoresis of the supernatant recovered after adding three different buffers (i.e., 75% buffer B, 90% buffer B, and 0.1 M HCl solution (pH 1)) to a plasma protein sample on PBE 94 resin, as described in Example 1. The proteins visualized on the gel are those that were solubilized. The percent of buffer B (v/v) is marked on the horizontal axis. The molecular weight (kDa) standards are marked on the vertical axis.
Figure 5B:
Figure 5C:
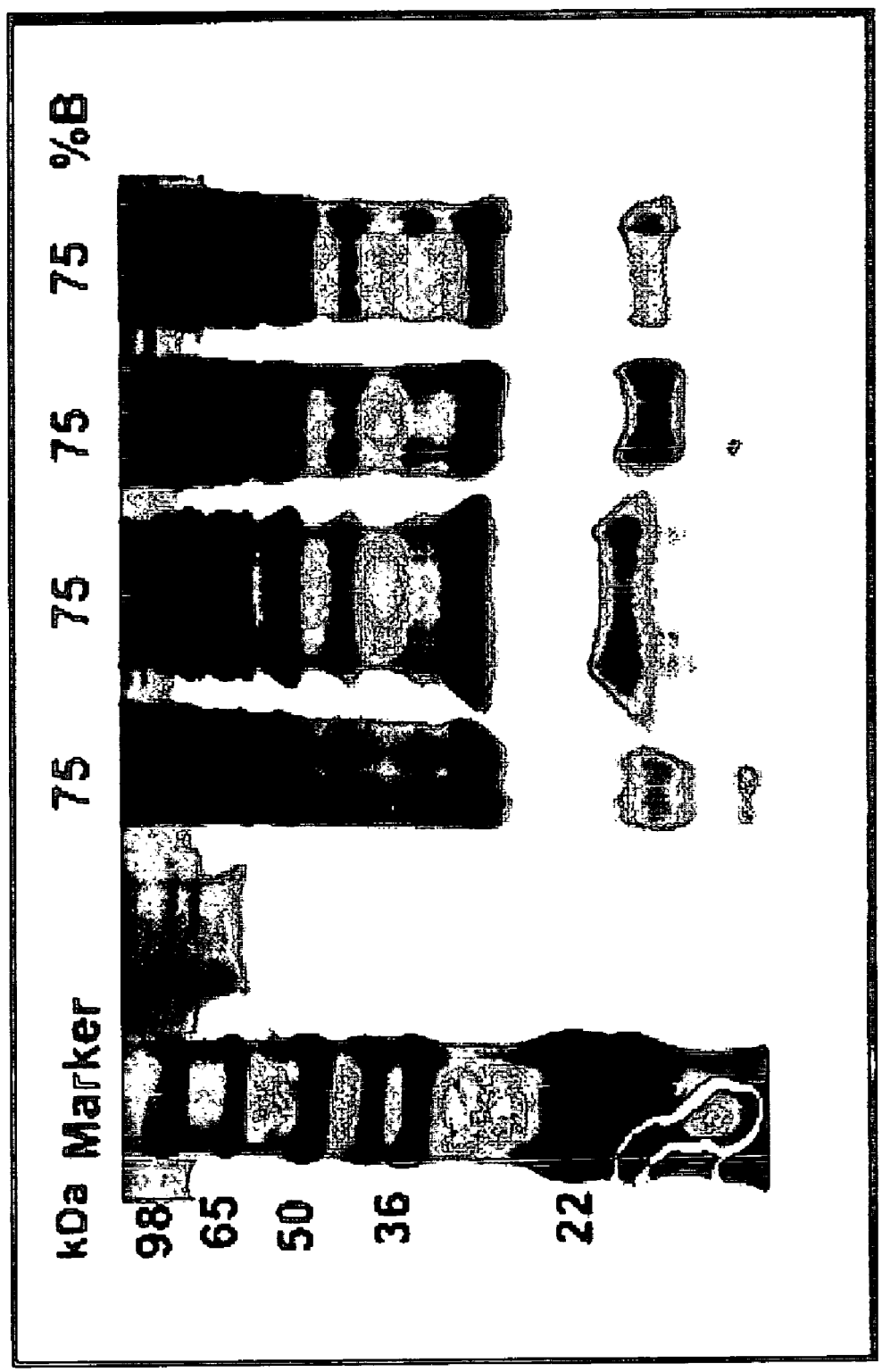
FIG. 5C and FIG. 5D depict the same gels as FIGS. 5A and 5B however.
Figure 5D:
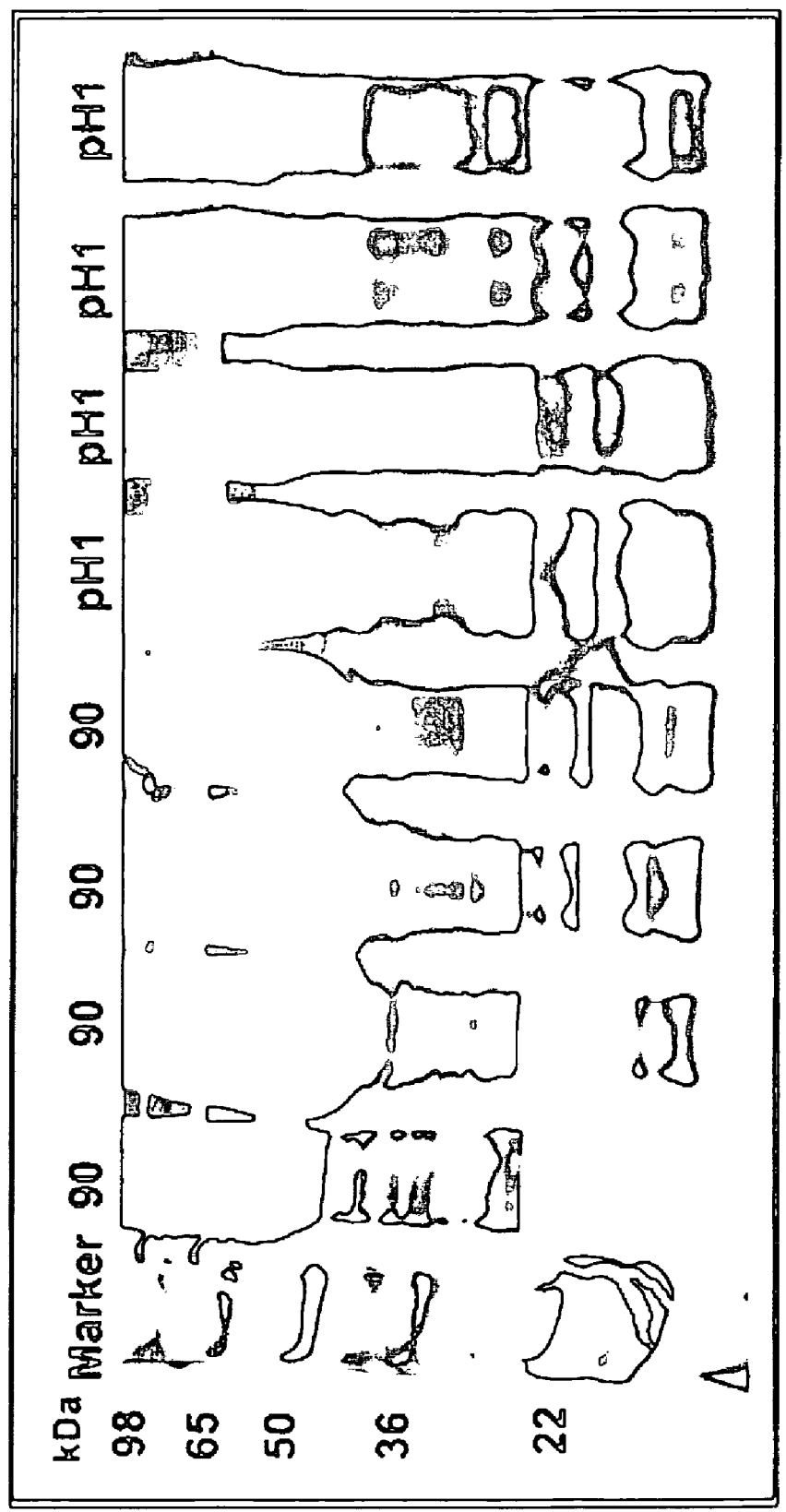

At 75% buffer B, no major 65 kDa bands appeared on the gel (FIGS. 5A and 5C). At 90% buffer B, dominant bands appear at 65 kDa (FIGS. 5B and 5D). At pH 1, a large band appeared at 65 kDa (FIGS. 5B and 5D). This band is thought to represent albumin or other proteins that have molecular masses comparable to that of albumin such as α1-antitrypsin and α1-antichymotrypsin.

Two-Dimensional Gel Electrophoresis

For this analysis, fractions 1 to 4 and 9 to 12 were combined in one tube, while the four albumin-containing fractions (5 to 8) were combined in another. The two solutions were dried using a vacuum centrifuge and were then reconstituted in 185 µL of rehydration buffer consisting of 8 M urea, 50 mM dithiothreitol, 2% CHAPS, 0.2% Bio-lyte 3/10 Ampholyte, and 0.001% bromophenol blue. In addition to these two solutions 100 µg of the original human plasma protein sample was diluted with 185 µL of the same rehydration buffer. Protein concentrations in this example were determined using bicinchoninic acid assay (BCA®) (Pierce, Rockford, Ill.) with bovine serum albumin (BSA) standards according to the manufacturer's instructions. The concentration of proteins in human plasma and different fractions was determined using the standard curve generated by the absorbance at 562 nm.

Two runs of 2-DE were performed. The first run loaded 275 µg of protein and analyzed the untreated sample and treated sample (fractions 1 to 4 combined with fractions 9 to 12). The second run loaded 100 µg of protein and analyzed the untreated sample, treated sample (fractions 1 to 4 combined with fractions 9 to 12), and albumin fractions (5-8).

The IPG strips were rehydrated at 50 V for 16 hours at 20° C. using an Immobilized pH Gradient (IPG) strip 11 cm long, pH 4 to 7. The proteins were focused at 250 V for 15 minutes; an 8000 V was then maintained for a total of 42,000 Vh per gel. The strips were then equilibrated for 10 minutes in 2.5 mL of a solution composed of 375 mM Tris-HCl pH 8.8, 6 M urea, 2% SDS and 2% dithiothreitol. After this first equilibration, the strip was equilibrated for another 10 minutes in 2.5 mL of a second equilibration buffer composed of 375 mM Tris-HCl pH 8.8, 6 M urea, and 2% SDS. The equilibrated IPG strips were washed with cathode buffer (0.1 M Tricine, 0.1 M Tris-HCl pH 8.2 and 0.1% SDS) and placed onto a 10% Tris-HCl Criterion® gel (Bio-Rad). The anode buffer consisted of 0.2 M Tris-HCl pH 8.9. Gels were electrophoresed at 20 mA/gel for 1 hour, then 100 mA/gel until the end of the separation.

All the gels were silver stained according to the following protocol: Gels were fixed in 50% methanol (v/v) and 12% acetic acid (v/v) for 2 hours, then washed 3 times in 50% ethanol (v/v). The duration of each wash was 20 minutes. Gels were then incubated in a 0.02% sodium thiosulfate solution (w/v) for 1 minute, followed by 4 one-minute washes in water. Gels were then placed in a solution composed of 0.2% silver nitrate (w/v) and 0.075% (v/v) formaldehyde for a period of 20 minutes, followed by 3 one-minute washes in water. Gels were then developed in a 6% sodium carbonate (w/v), 0.005% formaldehyde (v/v), and 0.004% sodium thiosulfate (w/v) solution until the protein bands were visualized. A 1% acetic acid solution was added to stop development of the gel.

Figure 6A:
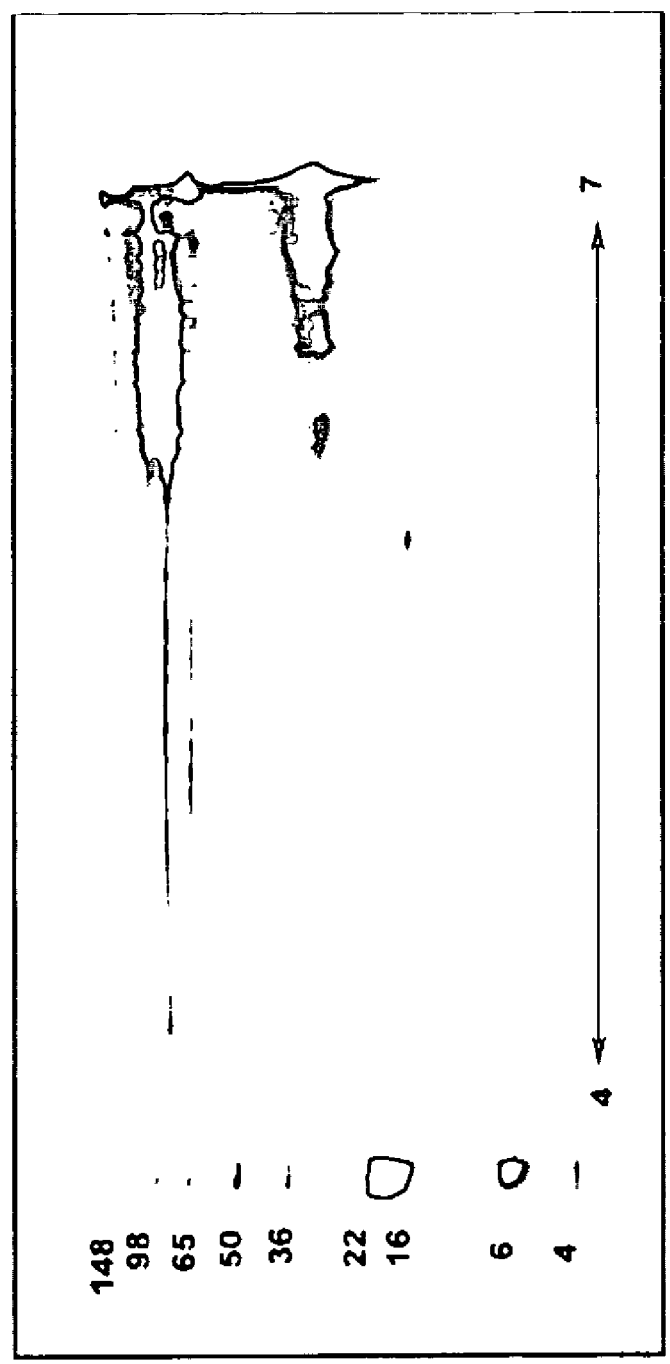
FIG. 6A-FIG. 6E depict the 2-DE of the original sample and samples fractionated in Example 1.
Figure 6B:
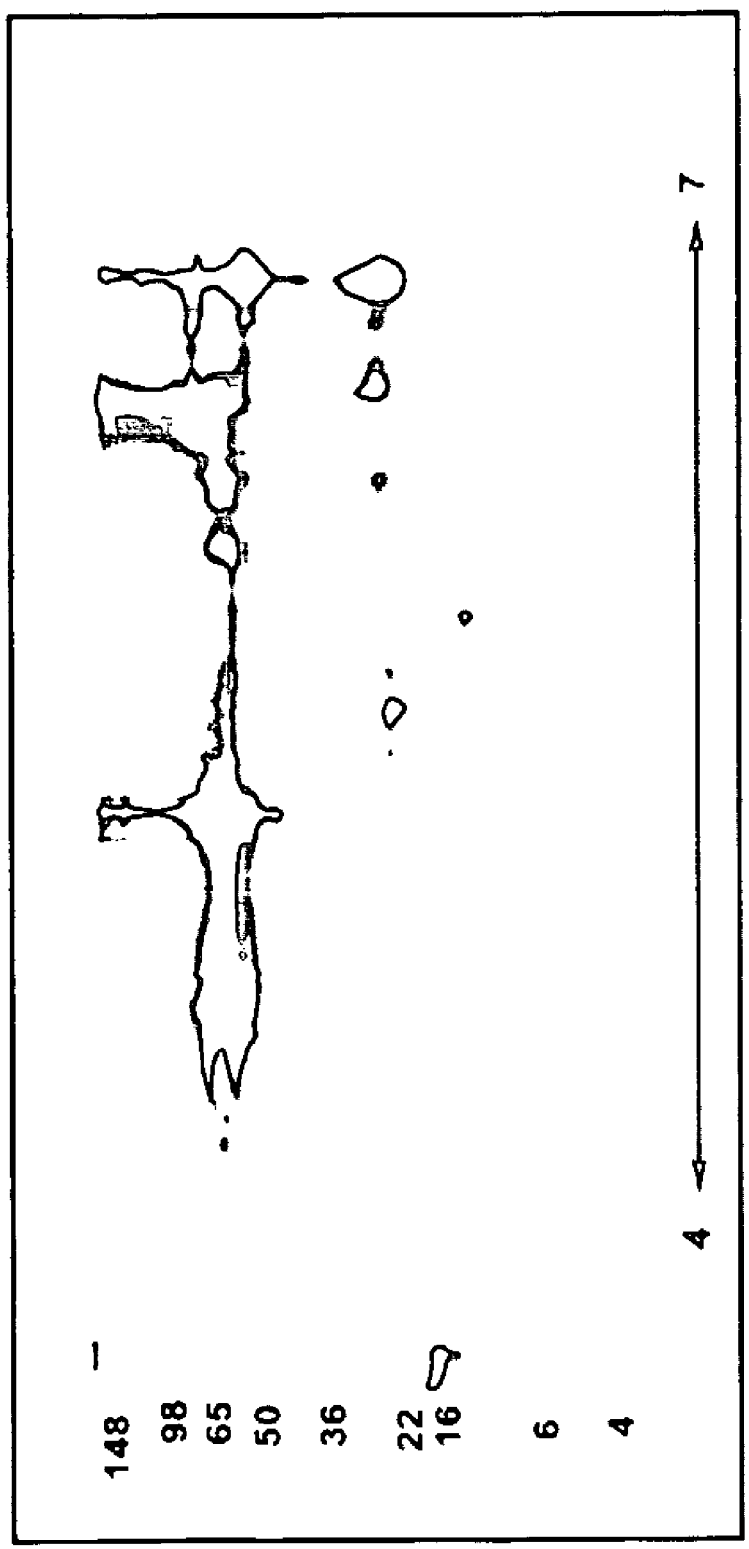

The 2-DE of the original plasma protein sample shows the presence of albumin and all the other proteins (FIGS. 6A and 6D), and served as control for 2-DE of the remaining fractions. The 2-DE of the combined 8 fractions collected after the 75% B and pH1 washes shows little albumin presence (FIGS. 6B and 6E). Large spots at acidic pI values close to 65 kDa represents α1-acid glycoprotein, α1-antitrypsin, and α1-antichymotrypsin. The presence of proteins that have a pI similar to that of albumin was noticed as well. 2-DE of the combined 4 fractions collected after the 90% B washes shows mainly albumin (FIG. 6C), with traces of bands corresponding to other proteins in the original sample. The identification of the proteins was done by comparing their position on the gel to that of the Swiss2-DPAGE database (http://us.expasy.org/tools/).

Proteins with a pI value similar to albumin, such as antitrypsin (pI 5.37), antichymotrypsin (pI 5.33), transthyretin (pI 5.52), and α1-acid glycoprotein (pI 5.65), were recovered after the separation procedure described here, in which Polybuffer Exchanger 94 resin was used to eliminate albumin from the human plasma protein sample. By adjusting the pH of the buffer-resin-human plasma sample mixture to a pH near the theoretical pI of albumin (5.92), by adding a 350 µL mixture consisting of 25% Buffer A and 75% Buffer B, all of the proteins that have a pI higher than that of albumin will be positively charged, and therefore, will remain in solution. Proteins that have a pI equal or close to that of albumin will be zero-charged, and will therefore precipitate. Some albumin molecules will be zero-charged, others with different glycation states will be slightly positively or negatively charged, depending on their pI, and will possibly precipitate during centrifugation due to their high molecular mass and low charge density. Proteins that have a pI lower than that of albumin will be negatively charged, and will therefore bind to the resin. The centrifugation allows for the formation of 2 layers: the bottom layer is the resin with the proteins bound to it, in addition to the precipitated albumin, and the top layer is the solution containing free proteins. This supernatant is recovered.

After this first step, the pH of the buffer-resin-human plasma sample is adjusted to a value that is approximately one unit lower than the pI of albumin (pH=4.7) by adding 350 µL of a mixture composed of 10% Buffer A and 90% Buffer B. Albumin, as well as proteins that share the same pI, will be positively charged and will therefore be soluble in the solution. Centrifugation then allows for the isolation of the supernatant solution containing primarily albumin. The last step is the addition of 350 µL of 0.1 M HCL solution. All acidic proteins bound to the resin will then be released and recovered by centrifugation. The recovery of several proteins or fragments that are in the same pI range as albumin is thought to be due to their higher solubility in the solution than albumin when their net charge is close to zero. When the pH is adjusted to a pI that is approximately equal to the theoretical pI of albumin, the net charge of some albumin molecules of certain glycation states, in addition to these recovered proteins and fragments, will be close to zero, and are therefore theoretically insoluble. The centrifugation at 5000×g results in the precipitation of albumin, but not of some smaller proteins and fragments, because these molecules have smaller sizes and may be soluble in the relatively high ionic strength of the buffers (approximately 50 mM).

Figure 6C:
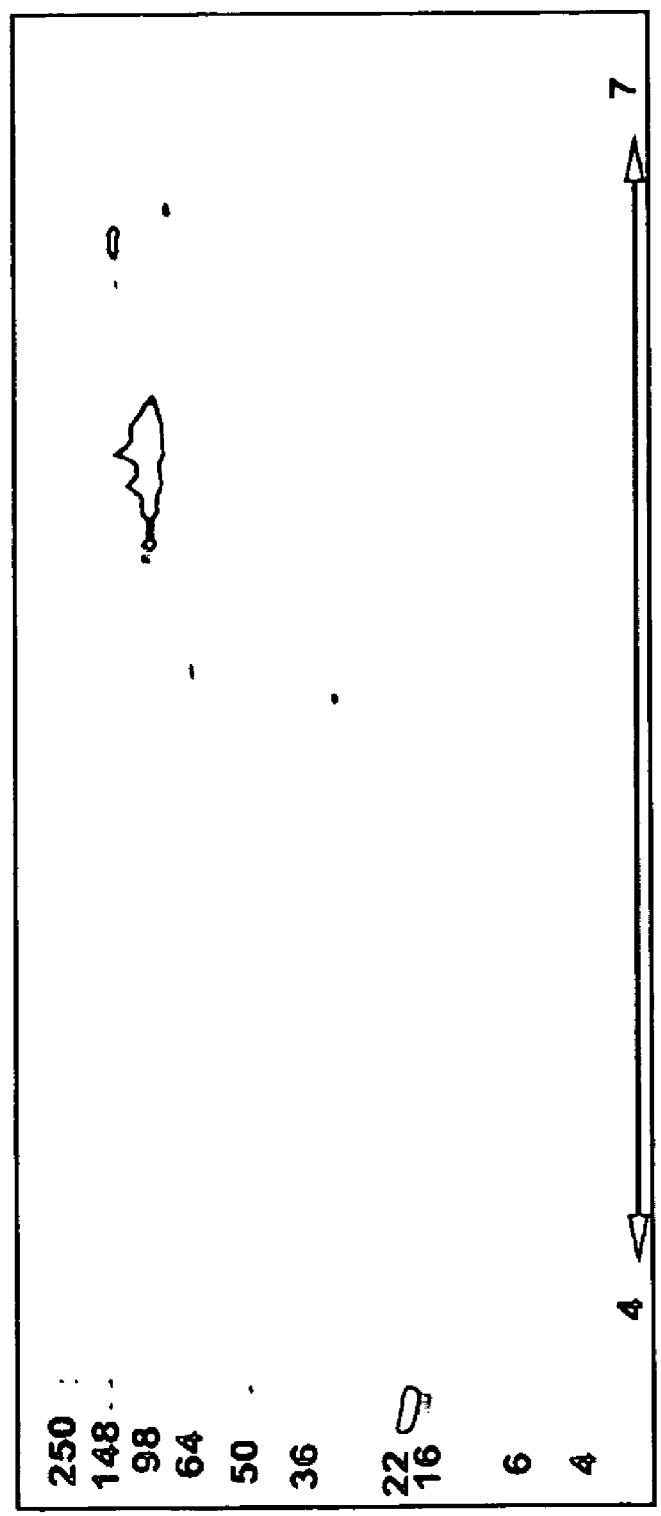
Figure 6D:
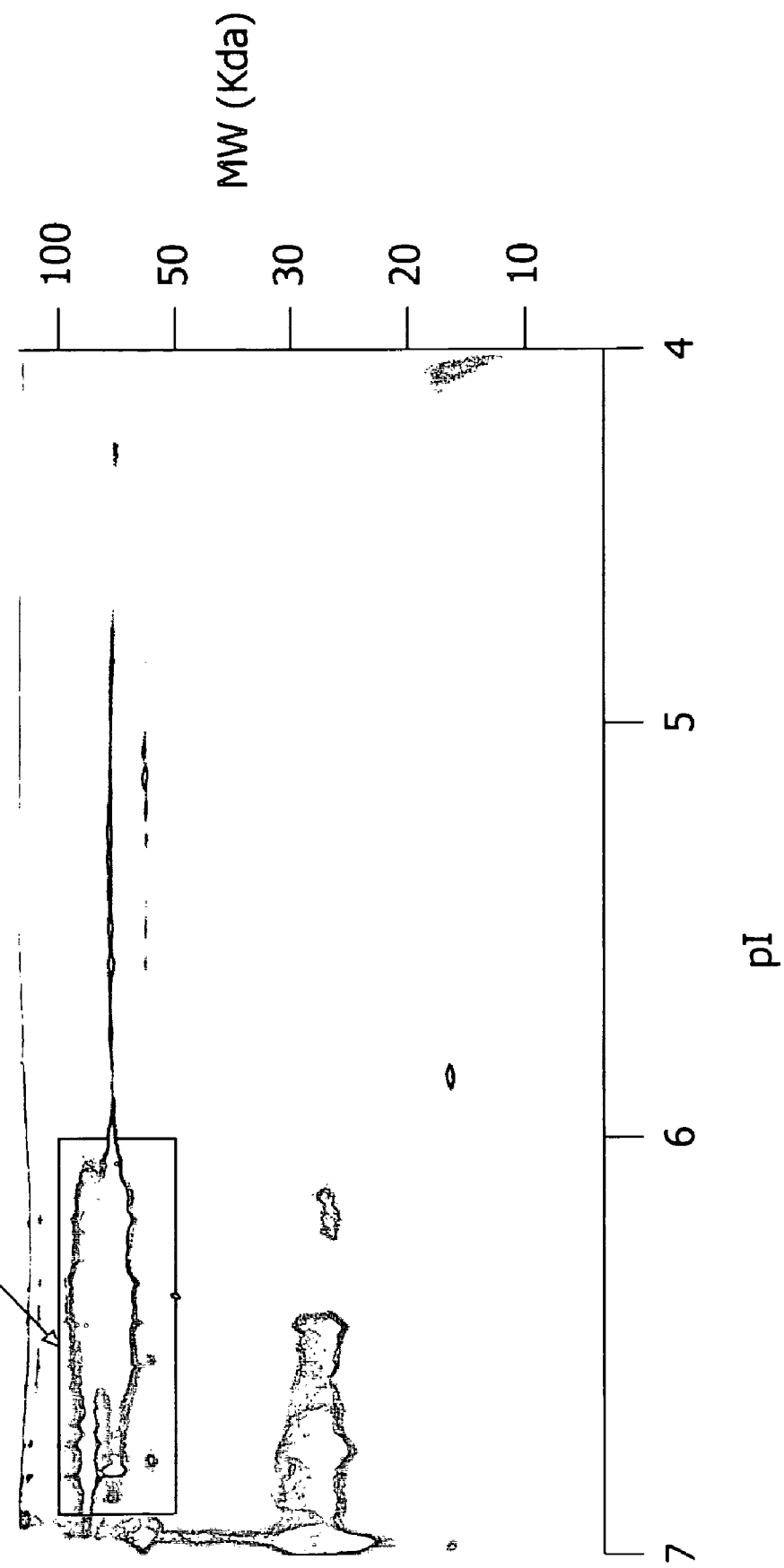
Figure 6E:
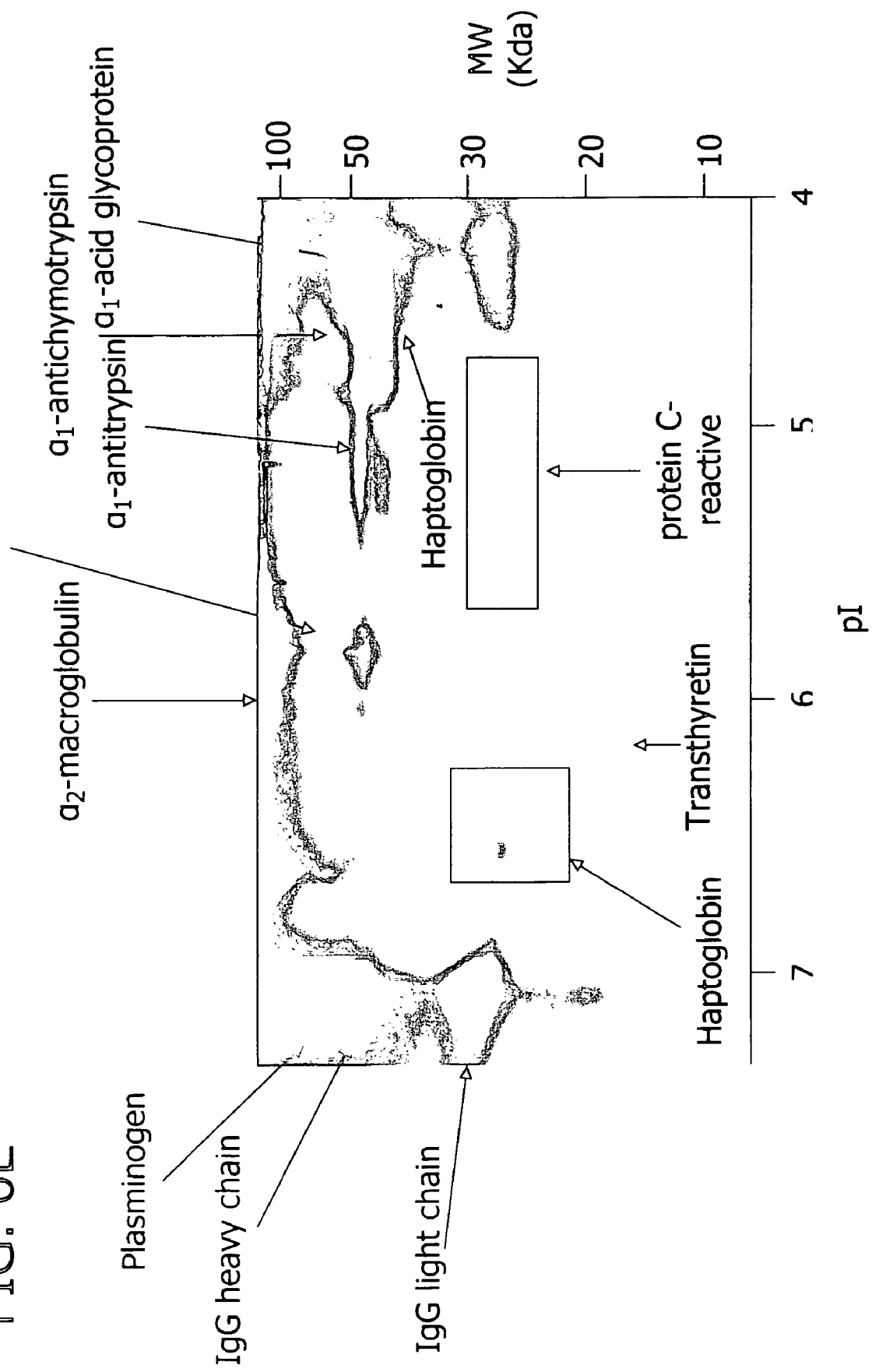

A quantitative analysis of protein concentration showed that 27.63 µg of proteins were present in the mixture containing fractions 1 to 4 and 9 to 12 (FIG. 6B), and 68.36 µg in the mixture containing fractions 5 to 8 (FIG. 6C). This represents a protein recovery of 96%.

Imaging Analysis

The number of individual spots on the gels was determined using ImageMaster 2D Platinum (Amersham Biosciences Corporation, Uppsala, Sweden). The parameters used were: Smooth 5, Min. Area 5, Saliency 1.0000.

ImageMaster 2D Platinum detected 62 spots in the 2-DE of total plasma protein versus 215 spots for the 2-DE of albumin-depleted plasma which represents a 3.4-fold increase in the number of spots detected.

Western Blotting

Matrix metalloproteinases (MMPs) are a group of zinc-containing enzymes that can collectively degrade all components of extracellular matrices (ECM) and some cell surface proteins. MMPs participate in tumor invasion and metastasis by hydrolyzing the basement membrane and other proteins, allowing the cancer cells to gain access to blood and lymph vessels. The detection of MMPs in the serum samples is important since studies on MMP-2 and MMP-9 showed that increased expression of these enzymes in the serum of prostate cancer patients detected using enzyme-linked immunosorbent assay (ELISA) is associated with advanced tumor stages. MMP-26, is the smallest member of the MMP family and is also known as endometase/matrilysin-2.

The ability of batch anion exchange prefractionation to remove albumin and increase detection of MMP-26 in human plasma samples was analyzed. Human plasma sample was diluted with a buffer composed of 25% buffer A and 75% buffer B to a volume of 400 µL and was added to 1 mL of the PBE94 resin that was previously washed with the same buffer composition. The mixture was then vortex mixed and centrifuged. The supernatant was collected. The resin was then washed three times with 350 µL of the same buffer compositions vortex mixed and centrifuged as described above. After performing BCA assay on this fraction, 10 µg of proteins were reconstituted with 15 µL of SDS-PAGE buffer and loaded on a 10% polyacrylamide gel against 10 µg of total plasma proteins as control. The gel was electrophoresed at 30 V for 30 minutes, then 50 mA until the end of the separation. Proteins contained within the gel were then electroblotted onto a nitrocellulose membrane (50 V for 50 minutes). Western blot analysis for MMP-26 was accomplished utilizing a 1 µg/mL dilution of rabbit anti-MMP-26 followed by incubation with horse radish peroxidase-conjugated anti-rabbit antibody. Visualization of the bands was then accomplished by the addition of a 1 to 1 ratio of Super Signal West Pico-Stable Peroxidase Solution and Luminol/Enhancer Solution (Pierce, Rockford, Ill.) and by developing the chemiluminescent signal on a Kodak film in the dark using Kodak Scientific Imaging Film (Kodak cat. 1651496), Fixer and Replenisher/Developer and Replenisher (Kodak cat. 1901859) according to the manufacturer's instructions.

Figure 7:
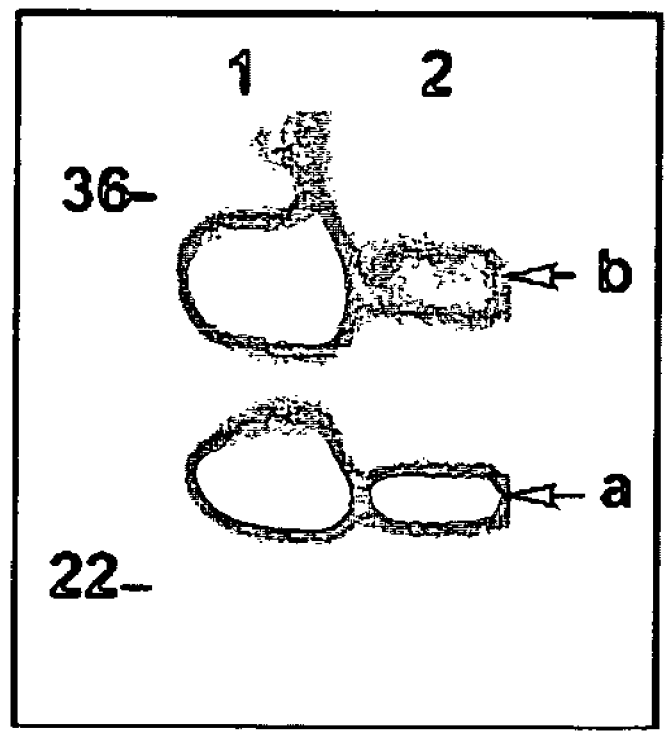
FIG. 7 depicts the Western blot of MMP-26 as described in Example 1. Western blotting of MMP-26 in human patient sera contained in 10 μg of an albumin-depleted human plasma sample (lane 1) and 10 μg of total human plasma (lane 2). Numbers on the left indicate molecular masses in kDa. Band a represents the glycosylated active form of MMP-26; band b represents the glycosylated latent form of MMP-26.

MMP-26 has a theoretical pI of 6.2, a molecular weight of 19 kDa for the active form and 26 kDa for the latent form, and has 3 potential glycosylation sites. Two bands were visualized between 22 and 36 kDa (FIG. 7) in the albumin-depleted sample corresponding to the glycosylated latent and active forms of MMP-26. The elimination of not only albumin but also all the other proteins that have pI values below 6 allowed increased loading of human plasma proteins that is crucial for enhancing the detection of low-abundance proteins like MMP-26.

Example 2

Fractionation of Cancer Serum Sample

Prostate-specific antigen (PSA) is an established serum marker for the diagnosis and management of prostate cancer. The proteolytic activity of PSA is inhibited by antichymotrypsin (ACT). PSA binds covalently to ACT and forms a complex (PSA-ACT). PSA-ACT is the major form of PSA present in human serum. The ratio of free PSA (FPSA) to PSA-ACT is of major clinical significance as it allows for the best clinical performance for prostate cancer detection.

The ability of batch anion exchange prefractionation to remove albumin and increase sensitivity of serum (PSA) analysis was compared to commercially available albumin purification methods based on, Cibacron Blue F3GA and albumin antibodies. Prostate cancer serum samples were provided by Dr. Kenneth A. Iczkowski, University of Florida, College of Medicine, Department of Pathology, Immunology and Laboratory Medicine, Gainesville, Fla.

2.1 Determination of Protein Concentrations

Protein concentrations in serum samples and fractions collected was determined using bicinchoninic acid assay (BCA®) (Pierce, Rockford, Ill.) with bovine serum albumin (BSA) standards according to the manufacturer's instructions. The concentration of proteins in human serum and different fractions was determined using the standard curve generated by the absorbance at 562 nm.

2.2 Albumin Elimination Using Commercially-Available Kits

SwellGel® Blue Albumin Removal Kit (Pierce, Rockford, Ill.) and ProteoSeek™ Antibody-Based Albumin/IgG Removal Kit (Pierce, Rockford, Ill.) were used according to the manufacturer's instructions. The albumin bound fraction was eluted by washing the SwellGel® resin with 0.25 M sodium thiocyanate 0.02M sodium phosphate and the ProteoSeek™ resin with boiling deionized water.

2.3 Serum Prefractionation

One mL of the PBE 94 resin was pipetted into a 1.5 mL centrifuge tube. Then, 350 μL of a solution composed of 25% Buffer A (from example 1) and 75% Buffer B (from example 1) was added to the resin, the tube was vortexed for 30 seconds, and this was followed by centrifugation at 5000×g for 30 seconds The supernatant was discarded. This equilibration step was repeated twice. Following equilibration, 275 μg of serum proteins were diluted with 350 μL of a buffer composed of 5 M urea, 2 M thiourea, 1% octylglucopyranoside (OG), 0.25% w/v Biolyte 3-10 ampholyte, 12.5% water saturated isobutanol, 10% isopropanol, 5% glycerol, and 50 mM dithiothreitol (DTT) and added to the resin followed by vortexing for 30 seconds The tube was then centrifuged at 5000×g for 30 seconds and the supernatant was recovered. The resin was washed three times with the same buffer (25% Buffer A, 75% Buffer B), with each iteration followed by vortexing for 30 seconds, centrifugation at 5000×g for 30 seconds, and supernatant recovery. The supernatant from this phase contained proteins with a pI higher than that of albumin. The resin was then washed with 350 μL of a solution composed of 10% Buffer A and 90% Buffer B, vortexed for 30 seconds, and centrifuged at 5000×g for 30 seconds The supernatant from this phase, containing albumin, was also recovered. This step was repeated three times. Finally, four washes of 350 μL of a 0.1 M HCl solution were performed, and the same procedures were followed to recover the supernatant. The supernatant from this phase contained the acidic proteins. This separation yields 12 fractions.

2.4 Western Blotting

After performing BCA assay, 10 μg of proteins from each fraction collected were reconstituted with 15 μL of SDS-PAGE buffer and loaded on a 10% polyacrylamide gel. The gel was electrophoresed at 30 V for 30 minutes, then 50 mA until the end of the separation. Proteins contained within the gel were then electroblotted onto a nitrocellulose membrane (50 V for 50 minutes). Western blot analysis for PSA was accomplished utilizing a 1 μg/mL dilution of monoclonal mouse anti-PSA (Santa Cruz Biotechnology, Santa Cruz, Calif.) followed by incubation with horse radish peroxidase-conjugated anti-mouse antibody. Visualization of the bands was then accomplished by the addition of a 1 to 1 ratio of Super Signal West Pico-Stable Peroxidase Solution and Luminol/Enhancer Solution (Pierce, Rockford, Ill.) and by developing the chemiluminescent signal on a Kodak film in the dark using Kodak Scientific Imaging Film (Kodak cat. 1651496), Fixer and Replenisher/Developer and Replenisher (Kodak cat. 1901859) according to the manufacturer's instructions.

Figure 8:
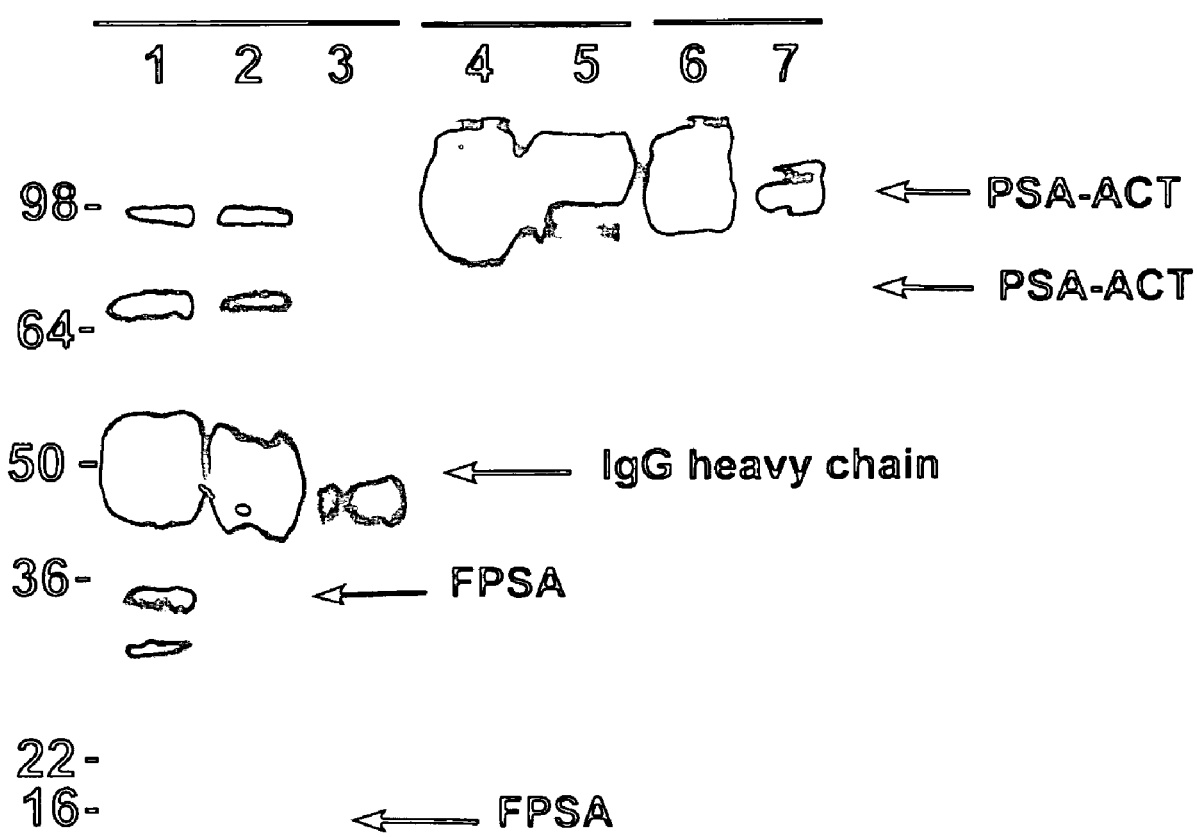
FIG. 8 depicts the Western blot of prostate-specific antigen (PSA) described in Example 2. Western blotting of PSA in a prostate cancer human patient serum is shown. Lane 1, 10 μg of proteins with pIs higher than that of albumin; lane 2, 10 μg of proteins with pIs similar to that of albumin; lane 3, 10 μg of proteins with pIs lower than that of albumin; lane 4, 10 μg of albumin-depleted serum using Cibacron blue F3GA; lane 5, 10 μg of the albumin fraction recovered after Cibacron blue F3GA treatment; lane 6, 10 μg of albumin and IgG-depleted serum sample using albumin antibody-conjugated resin; and lane 7, 10 μg of the albumin and IgG fraction recovered from the antibody-conjugated resin. Numbers on the left indicate molecular masses in kDa.

PSA bands are usually detected at a molecular mass of 13 to 34 kDa and have a pI of 8-8.8 44, 45. PSA-ACT complex is detected at a molecular mass of 96 kDa and have a pI of 6.5 to 7 46. PSA-ACT doublet which is the major form of PSA in the serum 37-42 was detected around 96 kDa in the first 2 fractions collected after batch anion exchange chromatography as well as in the albumin-depleted serum and the albumin fractions collected after using the 2 albumin elimination kits (FIG. 8). FPSA (14-34 kDa) which is the low-abundant form of PSA was detected in the first 2 fractions collected after batch anion exchange chromatography but not in the fractions collected after albumin elimination. The large band at 50 kDa represents IgG heavy chain that is immunoreactive with the secondary antibody used. Batch anion exchange prefractionation of the serum proteins resulted in a better protein denaturation and resolution since the serum sample was diluted with a buffer that contains 5 M urea, 2 M thiourea, 1% octylglucopyranoside (OG), 0.25% w/v Biolyte 3-10 ampholyte, 12.5% water saturated isobutanol, 10% isopropanol, 5% glycerol, and 50 mM dithiothreitol (DTT) prior to prefractionation.

Example 3

Prefractionation to Increase Resolution of LNCaP Proteins in 2-DE

3.1. Cell Culture, Treatment, and Lysis

Human prostate cancer cell line that was from a prostate cancer patient with lymph node metastasis, LNCaP cells (CRL-1740) was purchased from the American Type Culture Collection (ATCC, Manassas, Va.) and was maintained in Dulbecco's Modified Eagle's Media (DMEM) (Sigma, St. Louis, Mo.) without phenol red and was supplemented with 3.7 mg/mL NaHCO3, 10% fetal bovine serum (FBS) (Hyclone, Logan, Utah), 100 U/mL of Penicillin, and 100 μg/mL of Streptomycin (Cambrex, Walkersville, Md.). Cells were grown in a 100 mm×20 mm tissue culture plate with 10 mL of media at 37° C. in a humidified atmosphere consisting of 5% $CO_2$. EGCG was purchased from Sigma (St. Louis, Mo.) and dissolved in double distilled water to the final concentration of 50 mM. Cells were treated with 50 μM of EGCG for 24 hrs when they were at exponentially growing phase. The control was treated with the same volume of water. The volume of added EGCG stock solution was 0.1% of the total culture media. Cultured cells were washed three times with phosphate buffered saline (PBS), then lysed with 1 mL of lysis buffer as described 10, though modified to contain 5 M urea, 2 M thiourea, 1% octylglucopyranoside (OG), 0.25% w/v Biolyte 3-10 ampholyte, 12.5% water saturated isobutanol, 10% isopropanol, 5% glycerol, and 50 mM dithiothreitol (DTT). Cells were removed with a cell scraper and transferred to a centrifuge tube. Cells were vortexed for 5 minutes followed by centrifugation at 17000×g for 20 min. The supernatant was recovered and the precipitate was discarded.

3.2. Titration of the PBE 94 Resin with Start and Elution Buffers

PBE 94 was originally designed as a packing resin for anion exchange columns utilized as a liquid separation method for fractionating proteins according to their pI values. Chromatofocusing is an ion-exchange chromatography technique in which proteins are bound to an anion exchanger (PBE 94), then eluted by a continuous decrease of the buffer pH so that proteins elute in order of their isoelectric points 5. Polybuffer Exchanger 94 was packed in a 250 mm×5 mm column. The buffers used are described previously 16. The column was first equilibrated with Start buffer A (12.5 mM bis-tris propane and 12.5 mM piperazine in water-adjusted to pH 8 using HCl) at a flow rate of 1 mL/min until the eluted solution had a stable pH of 8. The concentration of Elution buffer B (12.5 mM pyridine, 12.5 mM acetic acid, 12.5 mM lactic acid and 12.5 mM chloroacetic acid in water, pH 3.3) was then set from 0 to 100% over 60 minutes, held on 100% for 30 minutes, and a 0.1 M HCl solution was pumped at the end to reach extremely acidic pH. The column was quickly reequilibrated with buffer A to avoid any damage secondary to the low pH. A pH meter was used to monitor the pH change of the eluting solution.

FIG. 10A shows the pH gradient generated by titration of the anion exchange resin with buffers A and B. A gradual increase in the concentration of buffer B resulted in a gradual decrease in the pH of the eluted solution.

3.3. Prefractionation of the LNCAP Cell Lysates Using PBE 94

Instead of packing PBE 94 into a column, 1 mL of this resin was pipetted in a centrifuge tube, followed by adding 350 µL of a solution composed of 50% buffer A and 50% buffer B. The tube was then vortex mixed for 30 seconds, centrifuged at 5000×g for 30 seconds, and the supernatant was discarded. This washing step was repeated twice. LNCaP cell lysate (330 µL) was then added to the resin along with 150 µL of a solution composed of 50% buffer A and 50% buffer B. The tube was vortex mixed for 30 seconds, centrifuged at 5000×g for 30 sec, and the supernatant was collected. The resin was washed three times with 350 µL of the same buffer (50% Buffer A, 50% Buffer B), with each iteration followed by vortex mixing for 30 seconds, centrifugation at 5000×g for 30 seconds, and supernatant recovery. The four supernatant fractions were then combined, vacuum-dried, and reconstituted in a sample buffer, which is the same as the lysis buffer described above. Protein concentration was determined as described below prior to the 2D-gel analysis. The resin was then washed four times with 350 µL of buffer B, followed by vortex mixing for 30 seconds and centrifugation at 5000×g for 30 seconds, and the supernatant was collected after each repeat.

By adjusting the pH of the solution containing the resin and the whole cell lysate to a value slightly below 7 using buffers A and B, all proteins with a pI higher than 7 will be net positively-charged (in cationic form), and therefore free in the solution. Those with pIs lower than 7 will either precipitate (if their pI is equal to the pH of the solution) or bind to the resin (FIG. 10B). Centrifugation then allows for the precipitation of the resin, and for the decantation of the supernatant containing proteins with pIs higher than 7. In the second step, by adjusting the pH of the solution containing the resin and remaining proteins, using buffer B to achieve a pH slightly lower than 4, all proteins with pIs between 4 and 7 will be net positively-charged, and therefore free in the solution. Those with a pI lower than 4 will either precipitate (if their pI is equal to the pH of the solution) or bind to the resin (FIG. 10C). Centrifugation then allows for the precipitation of the resin, and for the decantation of the supernatant containing proteins with pIs between 4 and 7.

3.4. Protein Assay

The protein concentration of the cell lysates and fractions collected was determined using bicinchoninic acid (BCA) Protein Assay Kit (Pierce, Rockford, Ill.) using bovine serum albumin (BSA) as standards according to the manufacturer's instruction. The concentrations of the proteins in the cell lysates and in the fractions were determined using the standard curve generated by the absorbance at 562 nm of standards in the Y axis versus the known concentration of the standards in the X axis.

3.5. Two-Dimensional Gel Electrophoresis 3.5.1. Isoelectric Focusing

Prefractionated samples were treated using Centricon-3 (Millipore, Danvers, Mass.), according to the manufacturer's instructions, to exchange their buffers with the rehydration buffer, which is the same as the lysis buffer described above. The samples were rehydrated at 50 V for 16 hours at 20° C. using 11 cm long Immobilized pH Gradient (IPG) strips, pH 4 to 7, 7 to 10, or 3 to 10. Proteins were focused at 250 V for 15 minutes, and then 8000 V was maintained for a total of 60,000 Vh per gel.

The strips were then equilibrated for 10 minutes in 2.5 mL of a solution constituted of 375 mM Tris-HCl pH 8.8, 6 M urea, 2% SDS, and 2% dithiothreitol. After this first equilibration, the strips were equilibrated for another 10 minutes in 2.5 mL of a second equilibration buffer constituted of 375 mM Tris-HCl pH 8.8, 6 M urea, 2% SDS, and 2% iodoacetamide.

3.5.2. SDS-Polyacrylamide Gel Separation

The equilibrated IPG strips were washed with cathode buffer (0.1 M Tricine, 0.1 M Tris-HCl pH 8.2, and 0.1% SDS) and placed onto a 10% Tris-HCl Criterion® gel (Bio-Rad, Hercules, Calif.). The anode buffer consisted of 0.2 M Tris-HCl pH 8.9. Gels were electrophoresed at 50 V for 30 min, then at 100 mA/gel until the end of the separation. Gels were silver stained for visualization of the proteins.

3.5.3. Silver Staining of Proteins

All the gels were silver stained according to the following protocol: Gels were fixed in 50% methanol (v/v) and 12% acetic acid (v/v) for 2 hours, then washed 3 times in 50% ethanol (v/v). The duration of each wash was 20 minutes. Gels were then incubated in a 0.02% sodium thiosulfate solution (w/v) for 1 minute, followed by 4 one-minute washes in water. Gels were then placed in a solution composed of 0.2% silver nitrate (w/v) and 0.075% (v/v) formaldehyde for a period of 20 minutes, followed by 3 one-minute washes in water. Gels were then developed in a 6% sodium carbonate (w/v), 0.005% formaldehyde (v/v), and 0.004% sodium thiosulfate (w/v) solution until the protein bands were visualized. An 1% acetic acid solution was added to stop the staining reactions.

3.6. Imaging Analysis

The numbers of individual spots on the gels were determined using ImageMaster 2D Platinum (Amersham Biosciences Corporation, Uppsala, Sweden). The parameters used were: Smooth 5, Min. Area 20, Saliency 1.0000.

RESULTS

FIG. 10A shows the pH gradient generated by titration of the anion exchange resin with buffers A and B. A gradual increase in the concentration of buffer B resulted in a gradual decrease in the pH of the eluted solution. The same resin (PBE 94) and buffers were used for the batch chromatography prefractionation. By adjusting the pH of the solution containing the resin and the whole cell lysate to a value slightly below 7 using buffers A and B, all proteins with a pI higher than 7 will be net positively-charged (in cationic form), and therefore free in the solution. Those with pIs lower than 7 will either precipitate (if their pI is equal to the pH of the solution) or bind to the resin (FIG. 10B). Centrifugation then allows for the precipitation of the resin, and for the decantation of the supernatant containing proteins with pIs higher than 7. In the second step, by adjusting the pH of the solution containing the resin and the remaining proteins, using buffer B to achieve a pH slightly lower than 4, all proteins with pIs between 4 and 7 will be net positively-charged, and therefore free in the solution. Those with a pI lower than 4 will either precipitate (if their pI is equal to the pH of the solution) or bind to the resin (FIG. 10C). Centrifugation then allows for the precipitation of the resin, and for the decantation of the supernatant containing proteins with pIs between 4 and 7.

After the adjustment of the resin pH to a value slightly below 7, 750 µg of total proteins in 330 µL LNCaP cell extracts were added to the resin and LNCaP cell lysates were prefractionated. Proteins with pIs above 7 were collected and a 100 µg (determined by the protein assay) were loaded onto a pH 7-10 IPG strip. The pH of the resin was then adjusted to a value slightly below 4 by washing the resin 4 times with 350 µL of buffer B, collecting the supernatant each time. These supernatants were then combined in one fraction and 100 µg of the proteins in that fraction (determined by the protein assay) were loaded onto a pH 4-7 IPG strip. 2-DE gels of the non-prefractionated LNCaP cell lysates using pH 4-7 or 7-10 IPG strips were compared to those of the prefractionated protein extracts (FIGS. 11 and 12). The numbers of spots detected using Image Master 2D Platinum on the non-prefractionated pH 4-7 gel were 298 spots for a loading of 250 µg, 761 spots for a loading of 100 µg of total proteins, and 1334 spots for a loading of 100 µg of prefractionated proteins. Therefore, the 2-DE obtained after loading 100 µg of prefractionated sample resulted in a 1.75-fold increase in the number of spots detected when compared to 2-DE obtained after loading 100 µg of total cell lysate (FIGS. 11B, 11C).

As for the pH 7-10 gels, the numbers of spots detected were 376 spots for a loading of 250 µg, 262 spots for a loading of 100 µg of total proteins, and 538 spots for a loading of 100 µg of prefractionated proteins. The increase in the number of spots detected was 2-fold (FIGS. 12B, 12C). In the non-prefractionated samples, many of the proteins loaded had pIs that did not fall within the narrow pH range of the IPG strip. This is particularly true when using 7-10 IPG strips as basic proteins are less abundant than acidic ones. Fractions isolated from LNCaP cell lysates containing proteins with pIs that fell primarily within the pH range of the IPG strip allowed for targeted loading, and as a result, better visualization of the less abundant proteins.

Overloading IPG strips with 250 µg of proteins resulted in poor focusing and as a result fewer proteins were detected (FIGS. 11A, 12A).

The prefractionated samples were then applied on wide pH 3-10 IPG strips to detect any cross-contamination between the fractions. The gels (FIG. 13) clearly show that proteins having the pI range being prefractionated are enriched, and very little contamination is observed for the 4-7 fraction (FIG. 13A). As for the 7-10 fraction, the gel shows some unresolved contamination (FIG. 13B) primarily at the lower pIs, but the majority of proteins separated is in the 7-10 pI range. This is mainly due to the fact that in any total cell lysate, basic proteins are less abundant than acidic ones.

After EGCG treatment, the number of spots detected on the non-prefractionated pH 4-7 gel is 811 spots versus 1458 spots for the prefractionated proteins. As for the pH 7-10 gel, the number of spots detected was 267 spots for the non-prefractionated sample versus 616 spots for the prefractionated proteins (FIGS. 14 and 15). Therefore, the prefractionation resulted in a 1.8-fold and 2.3-fold increase in the number of spots detected respectively for the acidic and basic proteome (FIGS. 14 and 15). Furthermore, comparing the EGCG-treated to non-treated samples, the differential number of spots detected after EGCG treatment increased from 55 spots for non-prefractionated samples to 202 spots for prefractionated ones, a 3.7-fold increase.

What is claimed is:

1. A process for separating a protein from a sample containing a mixture of proteins, the process comprising:
    combining the aqueous sample with a particulate cation exchange material or anion exchange material to form a first aqueous dispersion in which the particulate ion exchange material is capable of free-flowing movement relative to the remainder of the first aqueous dispersion, the pH of the first aqueous combination being (i) between about 0.5 pH units greater than the pI of the protein and about 5 pH units less than the pI of the protein when the ion exchange material is cation exchange material, and (ii) between about 0.5 pH units less than the pI of the protein and 5 pH units greater than the pI of the protein when the ion exchange material is anion exchange material,
    intensely mixing the first aqueous dispersion to cause the protein to bind to the ion exchange material and turbulent flow of the sample throughout the ion exchange material;
    separating the mixed first aqueous dispersion into (i) a concentrated solids fraction containing the ion exchange material and a precipitate of the protein and (ii) an aqueous fraction, and,
    recovering the protein from the concentrated solids fraction.

2. The method of claim 1, further comprising:
    forming a second aqueous dispersion, the second aqueous dispersion comprising the separated first concentrated solids fraction at a pH at which all proteins are released from the ion exchange resin;
    agitating the second aqueous dispersion;
    centrifuging the agitated second aqueous dispersion to form a second supernatant fraction and a second concentrated solids fraction, the second concentrated solids fraction comprising the ion exchange resin; and
    separating the second supernatant from the second concentrated solids fraction.

3. The method of claim 1, the method further comprising:
forming a second aqueous dispersion wherein the second aqueous dispersion comprises the separated first concentrated solids fraction and has a pH at which (i) a portion of the protein in the second aqueous dispersion remains bound to the ion exchange resin and (ii) at least a fraction of protein in the second aqueous dispersion dissolves into the second aqueous dispersion;
intensely mixing the second aqueous dispersion;
centrifuging the agitated second aqueous dispersion to form a second supernatant fraction and a second concentrated solids fraction, the second concentrated solids fraction comprising the ion exchange resin; and
separating the second supernatant from the second concentrated solids fraction.

4. The method of claim 1, the method further comprising:
forming a second aqueous dispersion wherein the second aqueous dispersion comprises the separated first concentrated solids fraction and has a pH at which (i) a portion of the protein in the second aqueous dispersion remains bound to the ion exchange resin and (ii) the proteins are not denatured;
intensely mixing the second aqueous dispersion;
centrifuging the agitated second aqueous dispersion to form a second supernatant fraction and a second concentrated solids fraction, the second concentrated solids fraction comprising the ion exchange resin; and
separating the second supernatant from the second concentrated solids fraction.

5. The process of claim 1 wherein the pH of the first aqueous dispersion is between about 0.2 pH units greater than the pI of the protein and about 1 pH unit less than the pI of the protein when the ion exchange material is cation exchange material, and (ii) between about 0.2 pH units less than the pI of the protein and 1 pH unit greater than the pI of the protein when the ion exchange material is anion exchange material.

* * * * *